US010174384B2

(12) United States Patent
Mathios et al.

(10) Patent No.: US 10,174,384 B2
(45) Date of Patent: Jan. 8, 2019

(54) USE OF THE ZMIZ1 MARKER IN DIRECTING TREATMENT AND PREDICTING SURVIVAL IN CANCER

(71) Applicant: THE JOHNS HOPKINS UNIVERSITY, Baltimore, MD (US)

(72) Inventors: Dimitrios Mathios, Baltimore, MD (US); Michael Lim, Reisterstown, MD (US); Patrick Ha, Sparks Glencoe, MD (US); Chetan Bettegowda, Perry Hall, MD (US); Taeyoung Hwang, Baltimore, MD (US); Chul-Kee Park, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/071,800

(22) Filed: Mar. 16, 2016

(65) Prior Publication Data

US 2016/0273050 A1 Sep. 22, 2016

Related U.S. Application Data

(60) Provisional application No. 62/133,714, filed on Mar. 16, 2015.

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS

2007/0054295 A1* 3/2007 Spivack ................ C12Q 1/686 435/6.12

OTHER PUBLICATIONS

Shames et al. PloS Medicine. 2006. 3(12):e486. (Year: 2006).*
Walter et al. Clin Cancer Res. 2012. 18(8):2360-2373. (Year: 2012).*
Tan et al. Carcinogenesis. 2002. 23(2):231-236. (Year: 2002).*
Brennan et al (2013) the somatic genomic landscape of glioblastoma. Cell. Oct. 10, 2013; 155(2):462-77.
Esteller et al (2001) p14ARF silencing by promoter hypermethylation mediates abnormal intracellular localization of MDM2. Cancer Res. Apr. 1, 2001;61(7):2816-21.
Jones et al (2002) The fundamental role of epigenetic events in cancer. Nat Rev Genet. Jun. 2002;3(6):415-28.

(Continued)

*Primary Examiner* — Joseph G. Dauner
(74) *Attorney, Agent, or Firm* — Johns Hopkins Technology Ventures

(57) ABSTRACT

The present invention relates to the field of cancer. More specifically, the present invention provides methods and compositions for treating cancer and predicting patient survival. In one embodiment, a method comprises (a) obtaining a biological sample from the patient; and (b) detecting hypermethylation of ZMIZ1 using primers that specifically bind to CpG island 139 at the alternative promoter of the ZMIZ1 gene.

1 Claim, 15 Drawing Sheets

Specification includes a Sequence Listing.

200 kb
80,850,000 80,900,000 80,950,000 81,000,000 81,050,000 hg19 81
Ref Seq Genes
ZMIZ1 FULL
UCSC GENES (REFSEQ, GENBANK, CCDS, RFAM, TRNAS & COMPACTIVE GENOMICS) ZMIZ1 TRUNCATED
ZMIZ1 BC126552 ZMIZ1 ZMIZ1
CPG ISLANDS (ISLANDS < 300 BASES ARE BOXED) ZMIZ1
CPG: 139
CPG METHYLATION BY METHY 1 450K BEAD ARRAYS FROM ENCODE/HAIB
PROBES CG26654807
SNP SIMPLE NUCLEOTIDE POLYMORPHISMS (DBSNP 141) FOUND IN > = 1% OF SAMPLES
TRANSCRIPT FACTOR CHIP-SEQ (161 FACTORS) FROM ENCODE WITH FACTORBOOK MOTIFS
CHIP-SEQ POLR2A

(56) References Cited

OTHER PUBLICATIONS

Stupp et al (2009) Effects of radiotherapy with concomitant and adjuvant temozolomide versus radiotherapy alone on survival in glioblastoma in a randomised phase III study: 5-year analysis of the EORTC-NCIC trial. Lancet Oncol. May 2009;10(5):459-66. doi: 10.1016/S1470-2045(09)70025-7. Epub Mar. 9, 2009.
Noushmehr et al (2010) Identification of a CpG island methylator phenotype that defines a distinct subgroup of glioma. Cancer Cell. May 18, 2010;17(5):510-22. doi: 10.1016/j.ccr.2010.03.017. Epub Apr. 15, 2010.
Parsons et al (2008) An integrated genomic analysis of human glioblastoma multiforme. Science. Sep. 26, 2008;321 (5897):1807-12. doi: 10.1126/science.1164382. Epub Sep. 4, 2008.
Maunakea et al (2010) Conserved role of intragenic DNA methylation in regulating alternative promoters. Nature. Jul. 8, 2010;466(7303):253-7. doi: 10.1038/nature09165.
Maunakea et al (2013) Intragenic DNA methylation modulates alternative splicing by recruiting MeCP2 to promote exon recognition. Cell Res. Nov. 2013;23(11):1256-69. doi: 10.1038/cr.2013.110. Epub Aug. 13, 2013.
Du et al (2010) Comparison of Beta-value and M-value methods for quantifying methylation levels by microarray analysis. BMC Bioinformatics. Nov. 30, 2010;11:587. doi: 10.1186/1471-2105-11-587.
Bady et al (2012) MGMT methylation analysis of glioblastoma on the Infinium methylation BeadChip identifies two distinct CpG regions associated with gene silencing and outcome, yielding a prediction model for comparisons across datasets, tumor grades, and CIMP-status. Acta Neuropathol. Oct. 2012;124(4):547-60. doi: 10.1007/s00401-012-1016-2. Epub Jul. 19, 2012.
Illingworth et al (2010) Orphan CpG islands identify numerous conserved promoters in the mammalian genome. PLoS Genet. Sep. 23, 2010;6(9):e1001134. doi: 10.1371/journal.pgen.1001134.
Verhaak et al (2010) Integrated genomic analysis identifies clinically relevant subtypes of glioblastoma characterized py abnormalities in PDGFRA, IDH1, EGFR, and NF1. Cancer Cell. Jan. 19, 2010;17(1):98-110. doi: 10.1016/j.ccr.2009.12.020.
Rogers et al (2013) Ectopic expression of Zmiz1 induces cutaneous squamous cell malignancies in a mouse model of cancer. J Invest Dermatol. Jul. 2013;133(7):1863-9. doi: 10.1038/jid.2013.77. Epub Feb. 20, 2013.
Li et al (2006) The novel PIAS-like protein hZimp10 enhances Smad transcriptional activity. J Biol Chem. Aug. 18, 2006;281(33):23748-56. Epub Jun. 15, 2006.
Lee et al (2007) The novel PIAS-like protein hZimp10 is a transcriptional co-activator of the p53 tumor suppressor. Nucleic Acids Res. 2007;35(13):4523-34. Epub Jun. 21, 2007.
Sharma et al (2003) hZimp10 is an androgen receptor co-activator and forms a complex with SUMO-1 at replication foci. EMBO J. Nov. 17, 2003;22(22):6101-14.
Li et al (2011) ZMIZ1 preferably enhances the transcriptional activity of androgen receptor with short polyglutamine tract. PLoS One. 2011;6(9):e25040. doi: 10.1371/journal.pone.0025040. Epub Sep. 20, 2011.
Beliakoff et al (2008) The PIAS-like protein Zimp10 is essential for embryonic viability and proper vascular development. Mol Cell Biol. Jan. 2008;28(1):282-92. Epub Oct. 29, 2007.

* cited by examiner

USE OF THE ZMIZ1 MARKER IN DIRECTING TREATMENT AND PREDICTING SURVIVAL IN CANCER

CROSS-REFERENCE TO RELATED APPLICATIONS

This application claims the benefit of U.S. Provisional Application No. 62/133,714, filed Mar. 16, 2015, which is incorporated herein by reference in its entirety.

FIELD OF THE INVENTION

The present invention relates to the field of cancer. More specifically, the present invention provides methods and compositions for treating cancer and predicting patient survival.

INCORPORATION-BY-REFERENCE OF MATERIAL SUBMITTED ELECTRONICALLY

This application contains a sequence listing. It has been submitted electronically via EFS-Web as an ASCII text file entitled "P13155-02_ST25.txt." The sequence listing is 173,914 bytes in size, and was created on Mar. 16, 2016. It is hereby incorporated by reference in its entirety.

BACKGROUND OF THE INVENTION

The role of DNA methylation in cancer pathogenesis has been investigated to a great extent in multiple cancer types. In particular, the methylation of CpG islands (CGIs) in the 5' promoter gene region has been known to suppress the transcription of tumor suppressor genes leading to tumorigeneisis. The retinoblastoma family gene p14INK4a is a well-known example [1]. More specifically, methylation of the CGIs in the gene promoter region has been shown to silence RNA expression leading to upstream effects that can change the activation status of several cancer related pathways [2]. Because of the extended effect methylation can have on cancer, it has been successfully used as a biomarker of treatment response and prognosis in some cancer types. For example, MGMT methylation has been identified as a biomarker of positive response to temozolamide and radiation in patients with glioblastoma [3]. Recent work in gliomas has identified a set of patients that exhibit hypermethylation in multiple loci, termed Glioma CpG Island Hypermethylator Phenotype (G-CIMP) [4, 5]. These patients have been found to harbor IDH1 mutations that cause the hypermethylator phenotype, a well-known genetic abnormality in gliomas [6]. However, most studies attempting to identify methylation markers of tumor prognosis have been limiting their interest in methylation signatures identified within CGI in the 5' promoter region of known genes. This is mainly because the biological relation between methylation and transcription is best understood in the 5' gene region while their true biological relation in other genomic regions such as the gene body is not well studied and thus so far unappreciated.

DETAILED DESCRIPTION OF THE INVENTION

Figure 1:
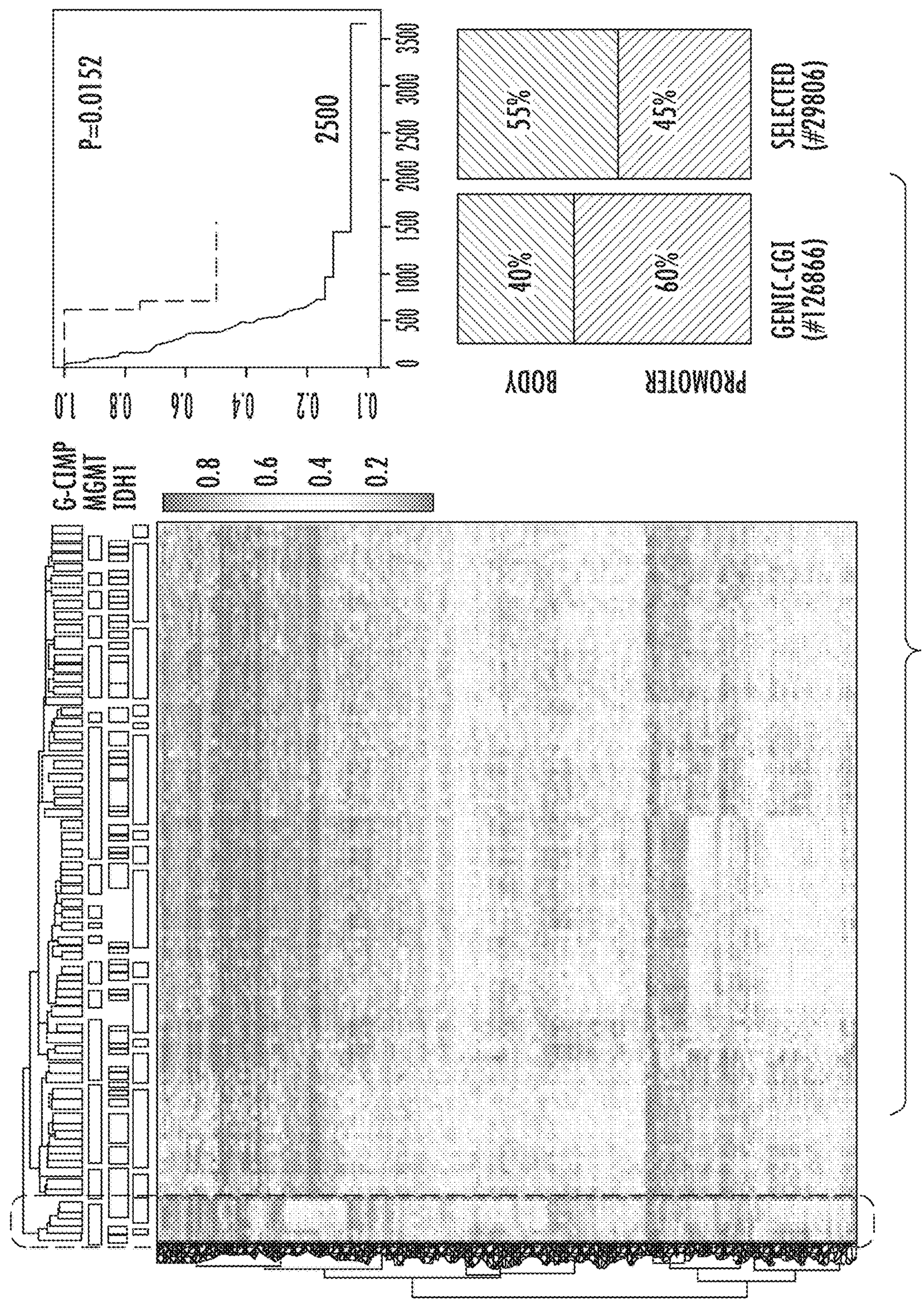
FIG. 1. Hierarchical clustering analysis identified a subgroup of 7 patients, mainly with IDH1 mutation or G-CIMP positive signature. Probes exhibiting the highest variability of beta values are enriched in the intragenic rather than the 5' promoter region.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

As described herein, the present inventors have identified ZMIZ1 expression as a marker of survival in several types of cancer including Advanced Ovarian CystadenoCa, Cervical Ca, Advanced Breast Ca, Lung Adenocarcinoma and Gliomas. Additionally, ZMIZ1 methylation can accurately predict long term survivors in Glioblastoma in an independent manner from the already known prognostic factors of MGMT methylation, GCIMP status and IDH1 mutation status.

Currently MGMT methylation status, IDH1 mutation status as well as GCIMP (Glioma CpG Island Methylation Phenotype) are used as prognostic markers of long term survivorship but none are specific and sensitive enough to differentiate those patients that live for more than 3 years. ZMIZ1 methylation status constitutes a gene that in our analyses has proven to be more sensitive and specific in the detection of long term survivors in glioblastoma. Furthermore ZMIZ1 can be useful in the prognosis of additional tumors including but not restricted to Advanced Ovarian CystadenoCa, Advanced Breast Ca, Lung Adenocarcinoma.

Recent genome-wide studies of DNA methylation show that tissue- and cell type-specific methylation manifests in gene body at a much greater proportion than the 5' promoter gene region [7]. Also, it is revealed that intragenic DNA methylation affects transcription through various mechanisms modulating alternative transcription or transcription elongation efficiency. Maunakea et al. have shown that intragenic methylation regulates exon recruitment and alternative splicing through the methyl-CpG-binding protein MeCP2 [8]. However, the significance of these processes, both intragenic methylation as well as alternative transcription are not well studied in the context of cancer.

Using methylation data of glioblastoma patients from The Cancer Genome Atlas (TCGA) as our discovery set, we show that gene body methylation can be used as a predictor of patient survival. Furthermore, we identify an alternative transcript of ZMIZ1 (UCSC ID: uc001kag.2) (originally named Zimp10 (zinc finger-containing, Miz1, PIAS-like protein on chromosome 10) whose methylation we identify as a novel biomarker of patient survival in glioblastoma. Highly methylated glioblastoma cases have a significantly increased survival compared to the hypo-methylated cases. To distinguish the predictive power of intragenic methylation of ZMIZ1 in glioblastoma from currently known biomarkers, we show that its predictive significance is independent from IDH1 mutation or MGMT methylation. Additionally, we confirm the significance of the alternative transcript of ZMIZ1, in multiple other tumors including lower grade gliomas as well as other non-central nervous system tumors on a DNA methylation or RNA expression level. The methylation status of the alternative promoter of ZMIZ1 was predictive of patient survival in lower grade gliomas, bladder cancer and renal cell carcinoma. The high RNA expression of the truncated ZMIZ1 transcript correlated with worse survival in patients with breast cancer, bladder cancer and colorectal cancer. Loss of function and gain of function studies showed that ZMIZ1 contributes significantly in the migration/invasion of cancer cells rather than on their proliferative capacity.

Accordingly, in one aspect, the present invention provides compositions and methods for predicting long-term survival of a cancer patient. In one embodiment, a method comprises detecting hypermethylation of ZMIZ1 using primers that specifically bind to CpG island 139 at the alternative promoter of the ZMIZ1 gene. In particular embodiments, CpG island 139 at the alternative promoter of the ZMIZ1 gene comprises the genomic location chr10:81002218-81002269. In certain embodiments, the primers comprise TATTTAGGGTTAGGGAAGTAAGATGT (SEQ ID NO:21). In other embodiments, the primers comprise AAACTAAACATCCAAATTAAATCTC (SEQ ID NO:22). In particular embodiments, the primers comprise SEQ ID NO:21 and SEQ ID NO:22. The cancer can be one of glioblastoma, lower grade glioma, renal cell carcinoma, or bladder cancer.

The present invention is also useful for predicting poor long-term survival of a breast or bladder cancer patient comprises the steps of detecting hyperexpression of the alternative transcript of ZMIZ1 (UCSC ID: uc001kag.2) in a biological sample obtained from the patient, as compared to a control.

In another aspect, the present invention also provides methods of treatment. In one embodiment, a method comprises administering a course of treatment appropriate for aggressive breast or bladder cancer to a patient exhibiting hyperexpression of the alternative transcript of ZMIZ1 (UCSC ID: uc001kag.2). In another embodiments, a method comprises administering a less intensive course of treatment to a cancer patient exhibiting hypermethylation of the alternative promoter of ZMIZ1. In particular embodiments, the hypermethylation of ZMIZ1 is detected using primers that specifically bind to CpG island 139 at the alternative promoter of the ZMIZ1 gene. In a specific embodiment, CpG island 139 at the alternative promoter of the ZMIZ1 gene comprises the genomic location chr10:81002218-81002269. In certain embodiments, the primers comprise SEQ ID NO:21 and SEQ ID NO:22. The cancer can be glioblastoma, lower grade glioma, renal cell carcinoma, or bladder cancer. The present invention also provides a method for predicting long-term survival of a cancer patient comprising the step of detecting expression of the alternative transcript of ZMIZ1 (UCSC ID: uc001kag.2). The transcript can be detected using a microarray or a PCR amplification reaction. In particular embodiments, Exon chr10: 81003425-81003495: + can be used as a surrogate marker to assess expression of alternative transcript of ZMIZ1 (UCSC ID: uc001kag.2). The method of claim 1, wherein the cancer is glioblastoma, lower grade glioma, renal cell carcinoma, or bladder cancer.

In particular embodiments, the present invention provides siRNA useful for the treatment of cancer. In certain embodiments, the siRNA comprises one or more of SEQ ID NOS:23-26. The present invention also provides methods for treating glioblastoma comprising the steps of administering (i) RNA interference molecules to knock down expression of ZMIZ1; and (ii) temozolamide. In particular embodiments, the RNA interference molecules are siRNA. In a specific embodiment, the siRNA knocks down expression of ZMI1. In another embodiment, the siRNA knocks down expression of the full length transcript of ZMIZ1 (uc001kaf.2). In yet another embodiment the siRNA knocks down expression of the alternative transcript of ZMIZ1 (uc001kag.2). In specific embodiments, the siRNA comprises one or more of SEQ ID NOS. 23-26. In other specific embodiments, the siRNA comprises s32836 (Life Technologies (Grand Island, N.Y., USA). In still further embodiments, a ZMIZ1 transcript comprises one of SEQ ID NO:3 or SEQ ID NO:5. In other embodiments, a ZMIZ1 transcript comprises SEQ ID NO:13, SEQ ID NO:15, SEQ ID NO:17 or SEQ ID NO:19.

Without further elaboration, it is believed that one skilled in the art, using the preceding description, can utilize the present invention to the fullest extent. The following examples are illustrative only, and not limiting of the remainder of the disclosure in any way whatsoever.

Examples

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Genome-Wide CGI Methylation Measurements.

Genome-wide methylation data for GBM samples, measured by Illumina Infinium HumanMethylation450 BeadChip (henceforth 'Infinium 450K array') were obtained from TCGA. The dataset provides the methylation status of 485,577 loci at a single nucleotide level for 120 GBM samples. Quantile-normalization was performed separately for the methylated ('M') and unmethylated ('UM') probes targeting 470,870 CpG sites in autosomes across the samples. The methylation level for a given genomic locus, "beta 03)", was estimated by the rate of M intensity relative to the total intensity which is the sum of M and UM intensities [9]. After normalization, we focused on 126,866 genomic sites associated with CGIs for NCBI reference genes.

The methylation status of MGMT used as a covariate in univariate and multivariate survival analysis was calculated based on the well-established method explained in detail in Bady et al [10].

Identification of Intragenic Molecular Markers.

Figure 11:
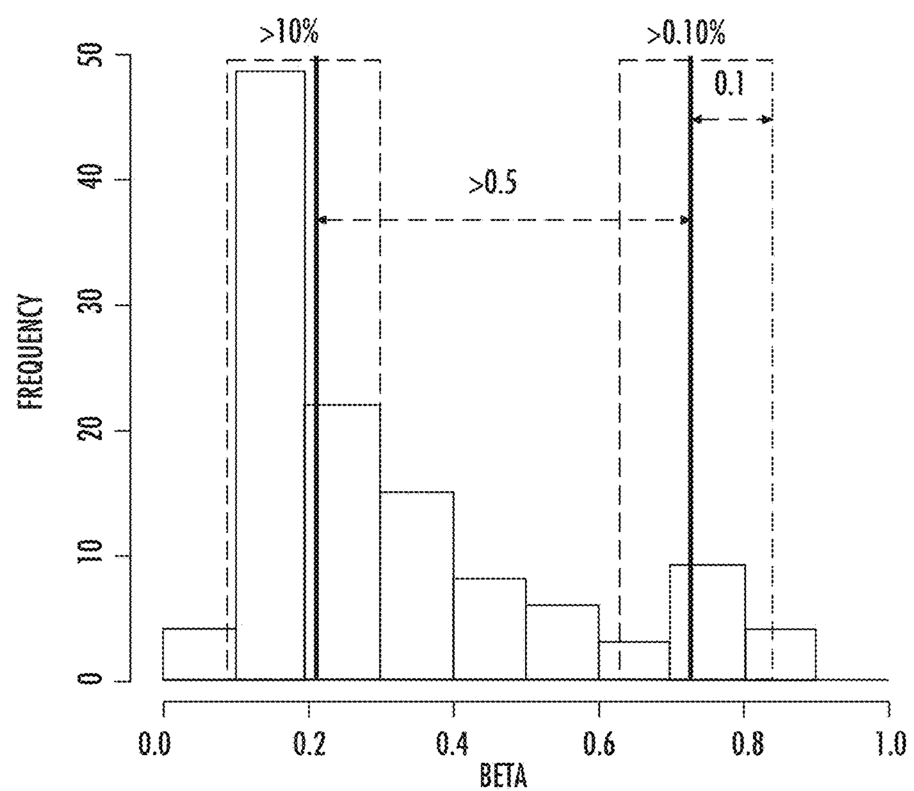
FIG. 11. Sites showing a strong bimodal distribution of beta values were identified in the following way; first, sites with standard deviation greater than 0.1 were selected. Second, for every site associated with gene body region, samples were classified into two groups labeled as "L" and "H" through hierarchical clustering with complete linkage of Euclidean distance. The median of beta values for every group-mode of the bimodal distribution ($\tilde{\beta}_L$ and $\tilde{\beta}_H$) was calculated, for any given site i.

Sites showing a strong bimodal distribution of beta values were identified in the following way; first, sites with standard deviation greater than 0.1 were selected. Second, for every site associated with gene body region, samples were classified into two groups labeled as "L" and "H" through hierarchical clustering with complete linkage of Euclidean distance. The median of beta values for every group-mode of the bimodal distribution ($\tilde{\beta}_L$ and $\tilde{\beta}_H$) was calculated, for any given site i. The bimodality of the distribution was assured by three criteria (FIG. 11): (1) $|\tilde{\beta}_H-\tilde{\beta}_L|>0.5$, (2) At least 10% of samples are within $\tilde{\beta}_H\pm0.1$ and at least 10% of samples are within $\tilde{\beta}_L\pm0.1$, (3) the average deviance defined by $$\frac{1}{J}\sum_{j=1}^{J}\min\{|\beta_{ij}-\tilde{\beta}_H|,\ |\beta_{ij}-\tilde{\beta}_L|\}$$

is less than 0.1. Finally, sites within a CGI associated with a promoter of a reference transcript were excluded to remove possible promoter-associated sites.

Classification of Samples into Hypo- or Hyper-Methylated Groups.

Figure 12:
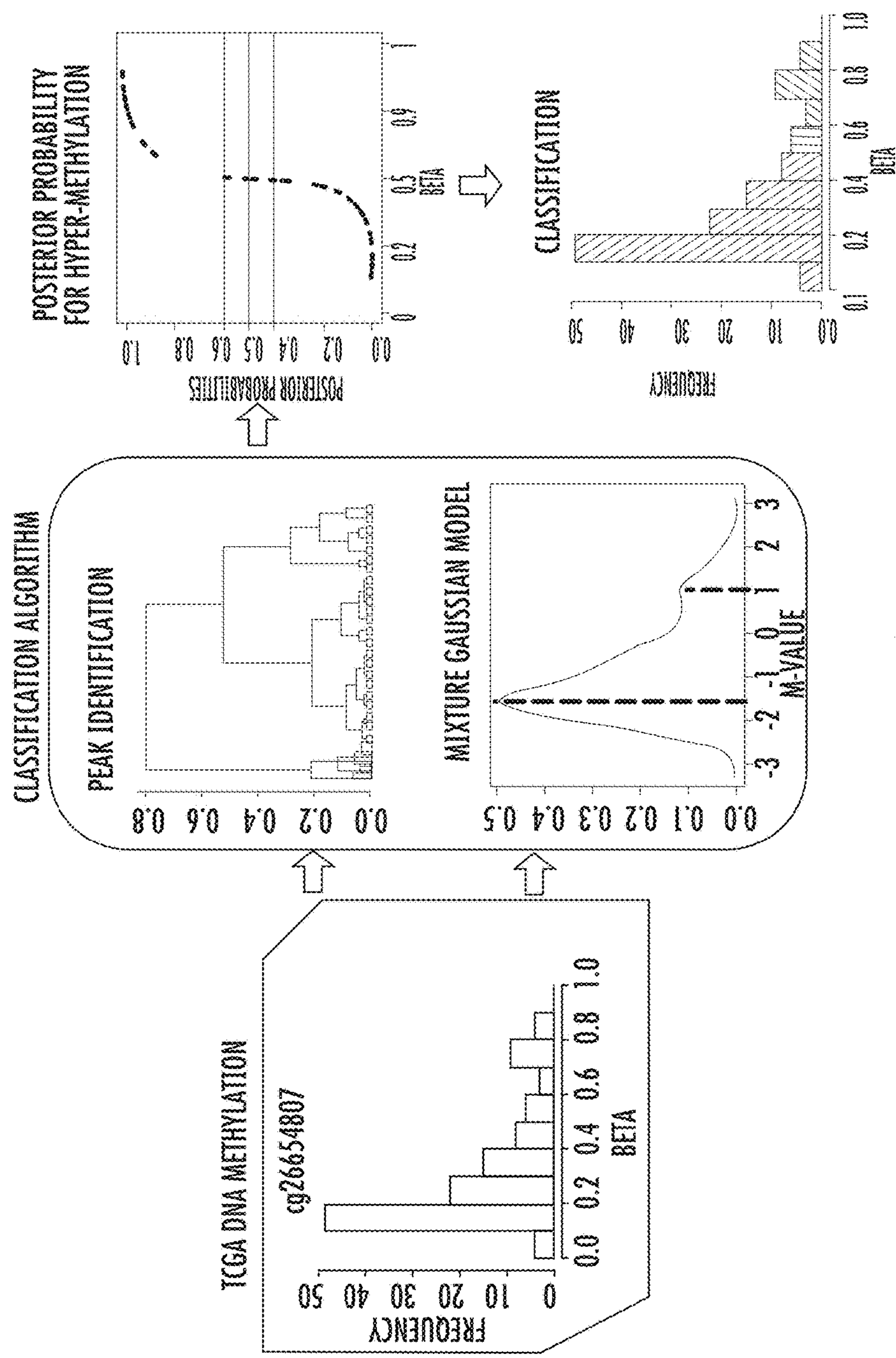
FIG. 12. Classification of samples into hypo- or hyper-methylated groups.
Figure 13:
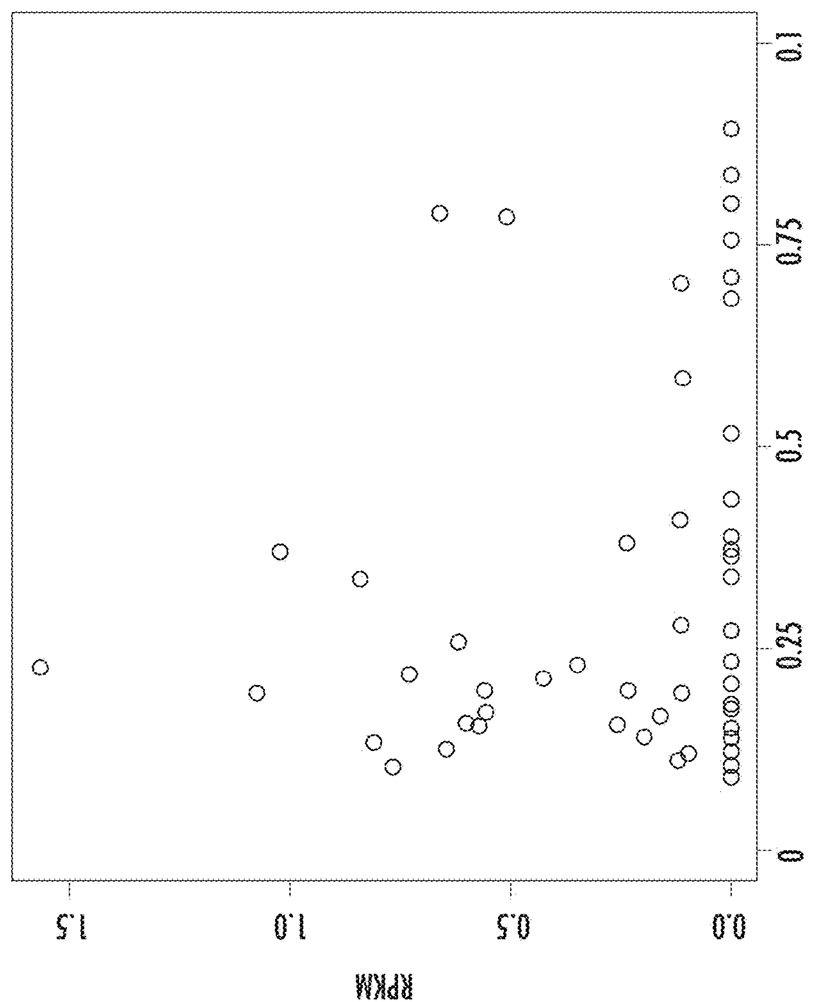
FIG. 13. The methylation status of this site is inversely correlated with the expression of the truncated ZMIZ1 transcript in GPM sample measured with RNA-sequencing in RPKM.
Figure 14:
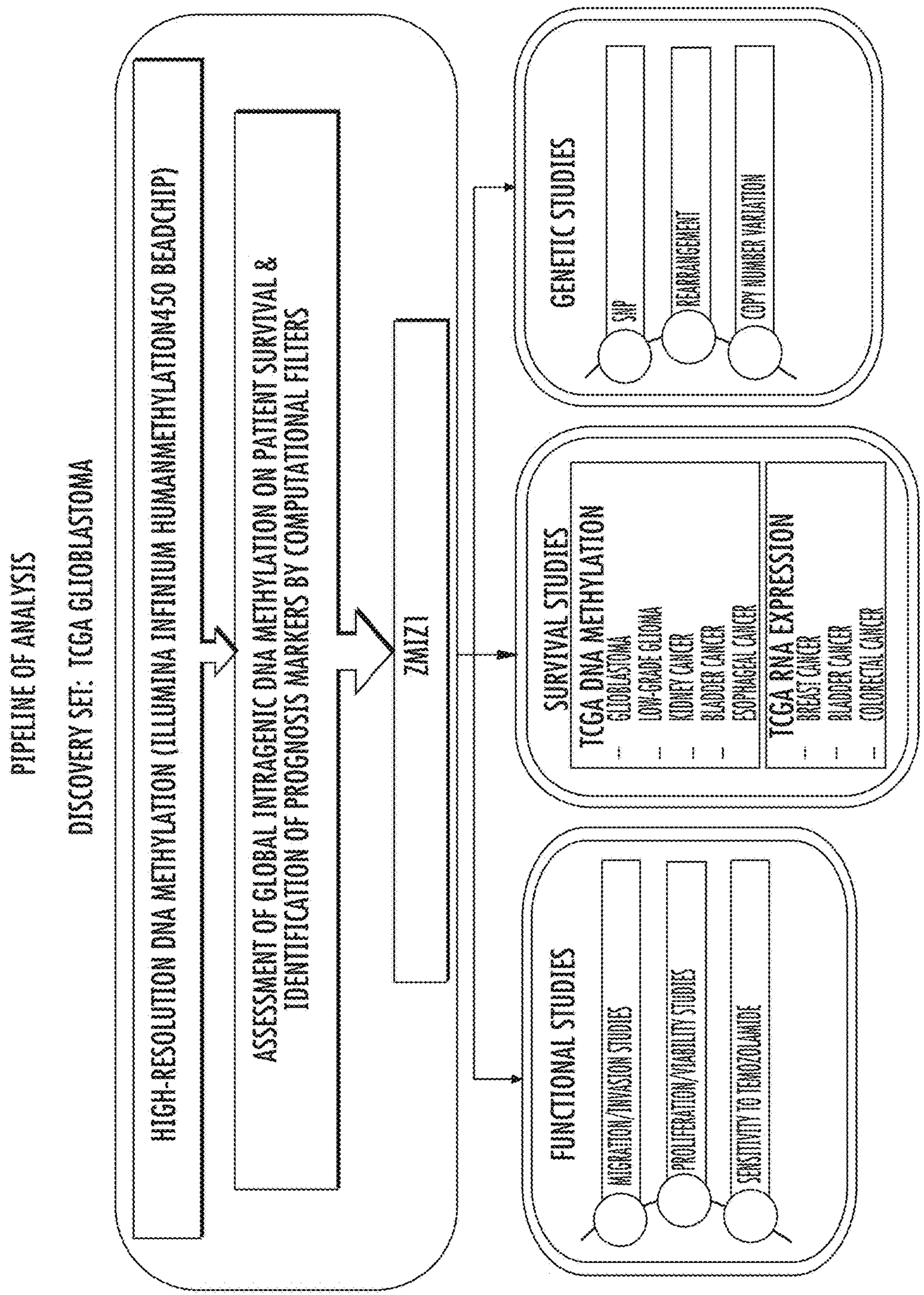
FIG. 14. Pipeline analysis.

In order to classify samples as hyper-methylated or hypo-methylated, M-values defined as the ratio of the M-probe intensity to UM-probe intensity were fitted to the mixture model of two normal distributions by Expectation-Maximization (EM) algorithm under the condition that the identified two peak values were used as means. If the posterior probability that a sample was hyper-methylated was less than 40%, then a sample was called "hypo-methylated" while if the probability was greater than 60%, a sample was labelled as "hyper-methylated". Otherwise, a sample was excluded from the survival analysis (FIG. 12).

RNA Sequencing Analysis.

Level 3 RNA-seq data were downloaded from TCGA for all cancer types, and Reads Per Kilobase of transcript per Million reads mapped (RPKM) values for the 1st exon of the alternative ZMIZ1 transcript (chr10: 81003425-81003495: +) were used to assess the RNA expression. Exon chr10: 81003425-81003495: + has been identified (Aceview-NCBI) as an alternative exon uniquely incorporated in the uc001kag.2 transcript of ZMIZ1; for this reason we used the expression levels of exon chr10: 81003425-81003495: + as a surrogate marker of the uc001kag.2 alternative transcript. A cut-off value of 1 Standard Deviation (SD) above the mean RPKM was used to stratify patients into the highly expressing uc001kag.2 group for all cancer types.

Cell Line Culture.

U87, U251 and LN18 cell lines were cultured in DMEM+10% FBS+1% Penicillin/Streptomycin. The Cancer Stem Cell (CSC)-like cell lines JHH-136, JHH-245, JHH-2010, JHH-221, JHH-211 (kindly provided by Dr. Gallia) and MY2 (kindly provided by Dr. Kai) were established from surgically resected GBM samples and were cultured in NeuroCult™ NS-A Proliferation Kit (Stem Cell Technologies, Vancouver, Canada) with the addition of EGF, FGF and 0.2% heparin per manufacturer's instructions. CSC-like cell lines GBM-318, GBM-276 (kindly provided by Dr. Quinones) and NS007 (kindly provided by Dr. Kai), were cultured in DMEM F12 with the addition of B27 w/o vitA, EGF, FGF and 0.2% heparin.

siRNA and Plasmid Design.

siRNA s32836 targeting both the full ZMIZ1 transcript (uc001kaf.2) and the truncated ZMIZ1 transcript (uc001kag.2) was purchased from Life Technologies (Grand Island, N.Y., USA), and two custom designed Stealth siRNAs (referred to as 56 and 62) targeting specifically uc001kag.2 were designed (Life Technologies) for all in vitro assays. The sequence of stealth_56 is Sense: CCGGUGCAACUUCUAGCCUUGUUGU (SEQ ID NO:23), Anti-Sense: ACAACAAGGCUAGAAGUUGCACCGG (SEQ ID NO:24), the sequence for stealth_62 is Sense: CAACUUCUAGCCUUGUUGUCCUCCU (SEQ ID NO:25), Anti-Sense: AGGAGGACAACAAGGCUAGAAGUUG (SEQ ID NO:26). Appropriate scrambled siRNAs were used as controls. Hyper-expressing plasmids were designed for both the full and the truncated plasmids. Appropriate empty vector was used as control for all in vitro assays described. Cells were transfected using Lipofectamine 2000 and the respective siRNA or plasmid and were treated for 6 h. The media was changed after 6 h and the regular culture media was subsequently used.

Viability Assay.

Cell titer glo (Promega, Madison, Mich.) assay was used to assess changes in the viability of cancer cells post manipulation of ZMIZ1 with siRNA or plasmid transfection. Briefly, cells were seeded in a 96 well plate at day 0 and allowed to grow for 1 day. At day 1, cells were transfected as described above. At several time points (day 2, 3, 4, 5) post transfection, cells were mixed with an equal volume of Cell titer glo solution and media to a volume of 200 ul. The 96 well plate was read 10 min after mixing in a Promega luminometer.

Proliferation Assay.

Carboxylfluosuccinimidylester (CFSE) labeling was performed according to the manufacturer's protocol (Life Technologies). Briefly, cells were rinsed with PBS supplemented with 1% BSA. The cells were incubated for 10 min with 10 uM of CFSE, then quenched with ice cold culture media for 5 min on ice and washed twice with culture media. Fresh media was subsequently added to the cells and they were incubated at 37 C. Cells were collected at certain time points (12 or 24 hours post CFSE labeling) from culture via trypsinization, washed once with Rinsing buffer (Miltenyi Biotec, San Diego, Calif., USA) and immediately analyzed on a FACS Calibur (BD Biosciences, San Jose, Calif., USA).

Migration-Invasion Assay.

Cells were seeded either in a polysterene 24 well plate or in 24 well plate coated with growth factor reduced Matrigel (Corning, Corning, N.Y.). When cells reached 100% confluency, treatment with either siRNA or plasmid was applied (Day 0). A scratch was created immediately after the completion of transfection. Low dose (5 ug/ml) of mitomycin C from *Streptomyces caespitosus* (Sigma-Aldrich, St. Louis, Mo.) was used in the migration experiments to inhibit any proliferative contribution to the "wound healing". The migration of cells was assessed using an inverted microscope (TE200 with CCD Camera, Nikon, Tokyo, Japan). NIS-Elements software (Nikon) was used to capture pictures of the scratch area at several time points (Day 0, 1, 2, 3, 4 post transfection) in the experiment. TScratch software developed by the Koumoutsakos group (CSE Lab), at ETH Zurich (Geback et al.) was used to quantitate the migration of cells. The migration of cells is reported as area covered in the scratch from the creation of the "wound" until its closure [$\Delta$ ($0_h$–$t_h$)].

Treatment with Temozolamide.

U87 and U251 GBM cell lines were treated with varying doses of temozolamide (Sigma Aldrich, St Louis, Mo.). 1000 cells/well were seeded in a 96 well plate. 24 hours later, cells were transfected with siRNA for 6 hours and when the media was changed, an appropriate amount of temozolamide (100 uM, 500 um and 1 mM for U251 and 10 uM and 20 uM for U87) was added to the desired concentration. Cells were followed for 3 days, and at the third day, viability was assessed with the cell titer glo assay.

Results

Putative Alternative Promoter Sites in Intragenic Regions are Enriched for Highly Differentially Methylated Sites in Glioblastoma Samples.

We first endeavored to identify CGIs that exhibit differential methylation in a TCGA cohort of 120 glioblastoma samples. We focused on sites found within NCBI gene annotated regions and considered sites that exhibited a standard deviation of beta values greater than 0.1 as highly differentially methylated. Using these criteria, we identified 30,399 probes within CGIs that were used to perform hierarchical clustering analysis. Our analysis identified a subgroup of 7 patients, mainly with IDH1 mutation (5 out of 6 patients with known IDH1 status) or G-CIMP positive signature (6 out of 7), confirming the previously reported results by Brennan et al. [5] (FIG. 1). This subgroup of patients exhibited a statistically significant improved overall survival compared to the other patients indicating the potential methylation has as a biomarker of improved survival in glioblastoma.

Figure 2:
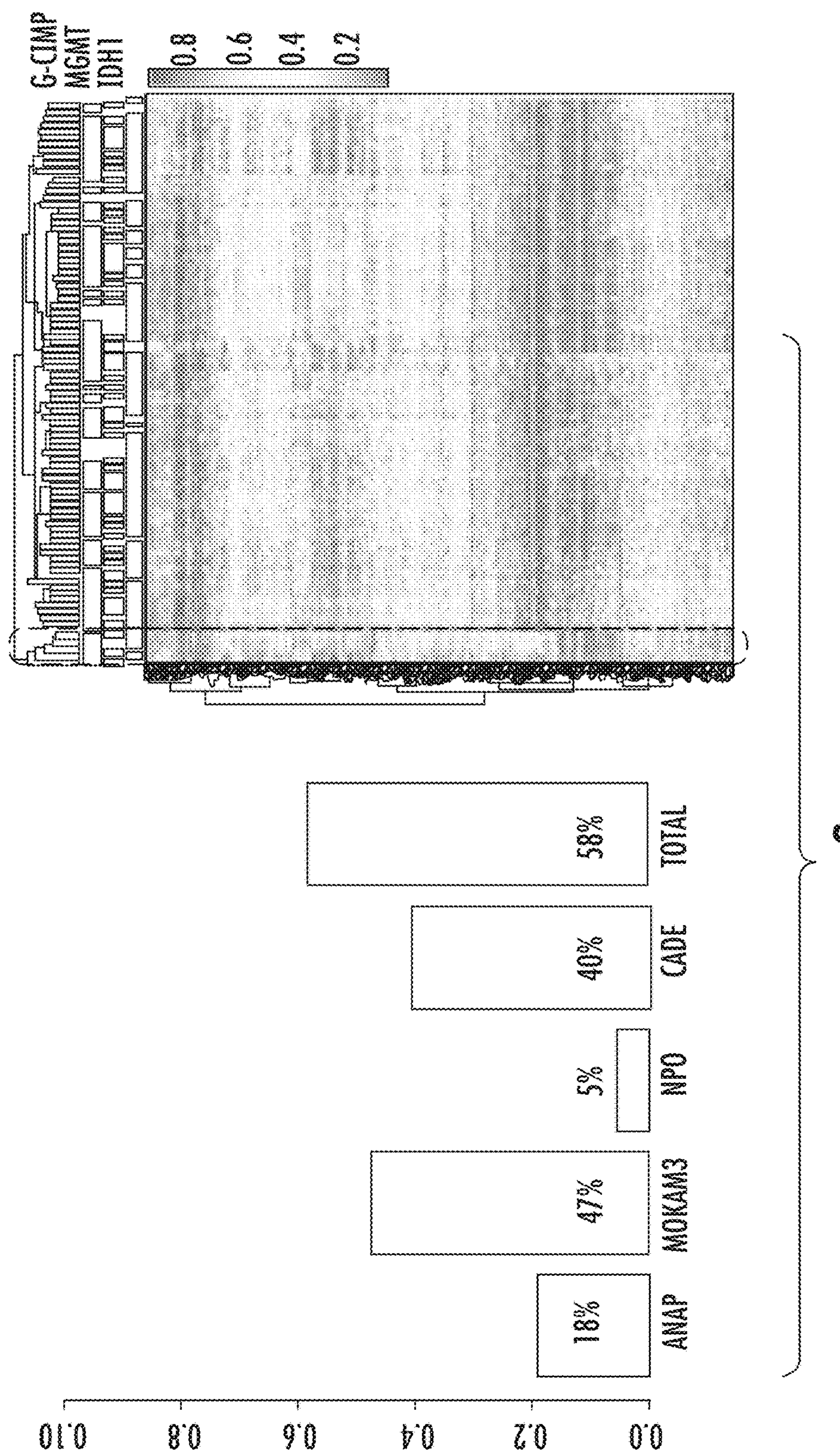
FIG. 2. Highly variable probes in the intragenic region are annotated with various types of molecular signatures for transcription. Intragenic variable sites alone can identify the G-CIMP positive subgroup of glioblastoma.

Most interestingly, we noted that the probes exhibiting the highest variability of beta values are enriched in the intragenic rather than the 5' promoter region (FIG. 1). Furthermore, 58% of these highly variable probes in the intragenic region are annotated with various types of molecular signatures for transcription such as binding sites of RNA polymerase II, specific histone-methylated (H3K4me3) sites, nascent RNA enrichment regions and 5' capping sites of RNA (FIG. 2). We also observed that intragenic variable sites alone can identify the G-CIMP positive subgroup of glioblastoma (FIG. 2).

Identification of a Truncated ZMIZ1 Isoform as an Intragenic Molecular Marker for Glioblastoma Classification The apparent ability of highly differentially methylated probes to discriminate survival status in gioblastoma patients (FIG. 1) as well as the higher percentage of highly differentially methylated probes within intragenic sites compared to 5' promoter sites motivated us to further analyze gene body associated CGI sites to identify possible molecular markers to predict survival in gliobastoma patients. To pursue this analysis, we chose to study all the probes that exhibited a strong bimodal distribution of beta values indicating that glioblastoma patients were either hypo- or hypermethylated at the site of that probe.

Using a defined set of criteria (Materials and Methods), we identified 161 probes in intragenic sites exhibiting a bimodal distribution of beta values. Table 1 shows the genes that contain at least two such probes with bimodal distribution.

Figure 3:
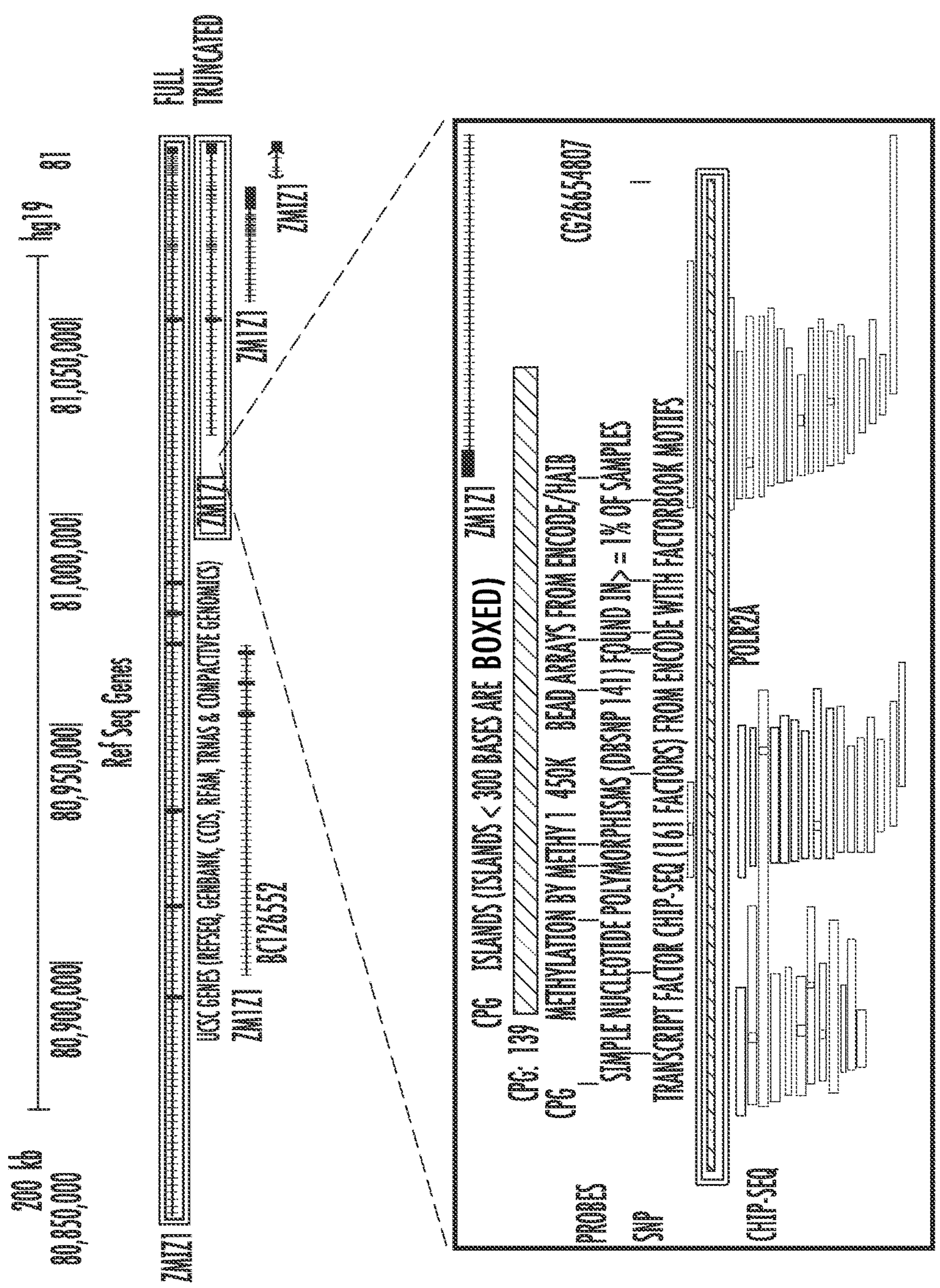
FIG. 3. Genomic region associated with a truncated transcript of ZMIZ1 carries histone marks and consensus genomic sequences that allow for transcription factor binding and most notably Polymerase II.

Among the sites in Table 1, we found that only the probes annotated with ZMIZ1 are associated with a known transcript. Specifically, cg26654807 450k Infinium methylation array probe is near the genomic region chr10:81002109-81003687 that is associated with a truncated transcript of ZMIZ1 found in UCSC mRNA database but not annotated in the NCBI refSeq database. This particular region carries histone marks and consensus genomic sequences that allow for transcription factor binding and most notably Polymerase II (FIG. 3), indicating a site of active transcription.

TABLE 1

| Chromosome | Gene | Probe ID | Coordinate | CpG Island | Standard Deviation | Peak 1 | Peak 2 |
|---|---|---|---|---|---|---|---|
| 1 | GPR153 | cg15892785 | 6309343 | Chr1:6309163-6310092 | 0.29 | 0.10 | 0.68 |
| | | cg07480647 | 6309724 | | 0.28 | 0.09 | 0.62 |
| | RAP1GAP | Cg21694350 | 21948793 | Chr1:21948674-21949263 | 0.23 | 0.11 | 0.61 |
| | | Cg00631482 | 21949221 | | 0.24 | 0.14 | 0.64 |

TABLE 1-continued

| Chromosome | Gene | Probe ID | Coordinate | CpG Island | Standard Deviation | Peak 1 | Peak 2 |
|---|---|---|---|---|---|---|---|
| | GPR88 | Cg14421860 | 101004934 | Chr1:101004471-101005885 | 0.23 | 0.03 | 0.63 |
| | | Cg22602002 | 101005376 | | 0.26 | 0.10 | 0.66 |
| 4 | PDGFRA | Cg03966785 | 55097476 | Chr4:55096185-55100331 | 0.24 | 0.07 | 0.63 |
| | | Cg23209990 | 55097576 | | 0.25 | 0.05 | 0.60 |
| 6 | NRN1 | Cg14386951 | 5999186 | Chr6:5999149-5999787 | 0.24 | 0.08 | 0.58 |
| | | Cg04187403 | 5999377 | | 0.23 | 0.24 | 0.78 |
| | HLA-J,ZNRD1-AS1 | Cg25318809 | 29974863 | Chr6:29974220-29975369 | 0.22 | 0.06 | 0.60 |
| | | Cg14781281 | 29974868 | | 0.21 | 0.05 | 0.59 |
| | | Cg08325845 | 29974886 | | 0.22 | 0.09 | 0.60 |
| | TRIM31 | Cg11002033 | 30071226 | Chr6:30071225-30071428 | 0.21 | 0.57 | 0.06 |
| | | Cg27319151 | 30071232 | | 0.20 | 0.62 | 0.10 |
| | | Cg23642250 | 30071394 | | 0.21 | 0.78 | 0.27 |
| | TNXB | Cg21460606 | 32055402 | Chr6:32055067-32055601 | 0.29 | 0.66 | 0.09 |
| | | Cg10365886 | 32063874 | Chr6:32053533-32065044 | 0.26 | 0.83 | 0.29 |
| 7 | EVX1 | Cg01357429 | 27285563 | Chr7:27284639-27286237 | 0.22 | 0.63 | 0.05 |
| | | Cg19480724 | 27285831 | | 0.23 | 0.06 | 0.58 |
| 9 | KIF12 | Cg13983319 | 116860500 | Chr9:116860473-116860695 | 0.22 | 0.06 | 0.64 |
| | | Cg14326196 | 116860650 | | 0.28 | 0.62 | 0.06 |
| 10 | ZMIZ1 | Cg26654807 | 81002218 | Chr10:81002109-81003687 | 0.21 | 0.20 | 0.74 |
| | | Cg14371731 | 81003175 | | 0.24 | 0.05 | 0.66 |
| | NKX2-3 | Cg17811778 | 101293172 | Chr10:101293015-101293238 | 0.21 | 0.11 | 0.64 |
| | | Cg19229344 | 101294643 | Chr10:101294443-101297263 | 0.23 | 0.12 | 0.63 |
| | TLX1 | Cg24812837 | 102894120 | Chr10:102893660-102895059 | 0.27 | 0.09 | 0.70 |
| | | Cg25266629 | 102894148 | | 0.26 | 0.14 | 0.69 |
| | MIR3663HG | Cg12112529 | 118922736 | Chr10:118922351-118923520 | 0.27 | 0.05 | 0.70 |
| | | Cg06746118 | 118922887 | | 0.26 | 0.08 | 0.69 |
| 13 | RNF219-AS1 | Cg27405554 | 79183424 | Chr13:79182859-79183880 | 0.24 | 0.12 | 0.65 |
| | | Cg17715222 | 79183694 | | 0.24 | 0.09 | 0.61 |
| | LINC00403 | Cg11423130 | 112630656 | Chr13:112630568-112630796 | 0.21 | 0.93 | 0.36 |
| | | Cg23619365 | 112712009 | Chr13:112709884-112712665 | 0.24 | 0.03 | 0.62 |
| 14 | LINC01551 | Cg20043105 | 29247458 | Chr14:29247324-29247624 | 0.23 | 0.12 | 0.63 |
| | | Cg12967137 | 29247605 | | 0.25 | 0.21 | 0.76 |
| 15 | MEIS2 | Cg15902390 | 37387438 | Chr15:37387386-37387614 | 0.29 | 0.12 | 0.76 |
| | | Cg26708220 | 37387577 | | 0.29 | 0.10 | 0.71 |
| 16 | PRSS27 | Cg04784471 | 2765637 | Chr16:2765619-2765855 | 0.22 | 0.03 | 0.54 |
| | | Cg10286959 | 2765843 | | 0.28 | 0.17 | 0.76 |
| 17 | ABR | Cg20592940 | 933155 | Chr17:933026-933236 | 0.26 | 0.85 | 0.30 |
| | | Cg22789318 | 981643 | Chr17:981508-981748 | 0.24 | 0.93 | 0.33 |
| 18 | MBP | Cg21655444 | 74770402 | Chr18:74770351-74770590 | 0.25 | 0.86 | 0.34 |
| | | Cg07807210 | 74770431 | | 0.28 | 0.84 | 0.31 |
| 19 | MAST1 | Cg08305551 | 12978611 | Chr19:12978359-12978785 | 0.26 | 0.05 | 0.63 |
| | | Cg06537894 | 12978706 | | 0.26 | 0.07 | 0.66 |
| | ARHGAP35 | Cg03604073 | 47507409 | Chr19:47507306-47507692 | 0.22 | 0.13 | 0.69 |
| | | Cg17431280 | 47507461 | | 0.25 | 0.10 | 0.72 |
| 21 | SIM2 | Cg10682155 | 38077473 | Chr21:38076762-38077685 | 0.23 | 0.13 | 0.68 |
| | | Cg01090834 | 38081193 | Chr21:38079941-38081833 | 0.27 | 0.18 | 0.69 |
| | | Cg01853561 | 38120466 | Chr21:38119793-38120741 | 0.24 | 0.19 | 0.73 |
| 22 | TBX1 | Cg19657174 | 19746268 | Chr22:19746155-19746369 | 0.21 | 0.19 | 0.69 |
| | | Cg08382235 | 19754251 | Chr22:19753312-19755013 | 0.20 | 0.09 | 0.61 |

In addition, the methylation status of this site is inversely correlated with the expression of the truncated ZMIZ1 transcript in GBM samples measured with RNA-sequencing in RPKM (FIG. 12), confirming an intragenic site associated with an alternative promoter.

Figure 4B:
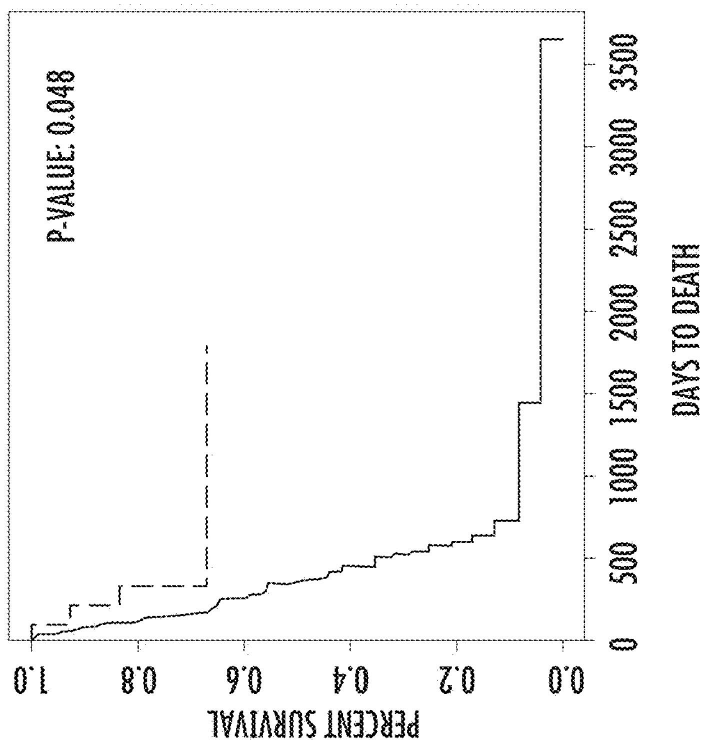
FIG. 4A-4B. Hyper-methylated samples show statistically significant survival advantage over hypo-methylated samples.
Figure 4A:
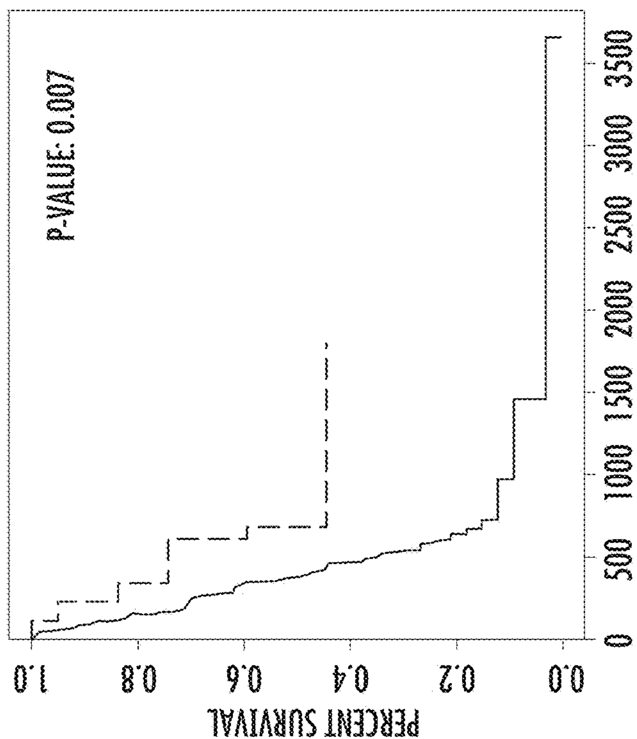

In order to evaluate the ZMIZ1 site as a molecular marker, Kaplan-Meier survival analysis was performed for the samples classified into the hyper-methylated or hypo-methylated group by the constrained normal mixture model (details are in the Materials and Methods section). The hyper-methylated samples show statistically significant survival advantage over hypo-methylated samples (n=120, p=0.007) (FIG. 4, Table 2). Univariate analysis was performed for identifying possible confounding factors of age, gender and race, type of surgical resection, type of adjuvant treatment (chemotherapy and radiation), intensity of treatment, IDH1 mutation status, G-CIMP status and MGMT methylation status. Multivariate analysis was performed using variables with a p-value less than 0.2 in the univariate analysis and known factors related with DNA methylation. After adjusting for age, IDH1 status, G-CIMP status, ZMIZ1 methylation status was marginally statistically significant with a p-value of 0.066 while IDH1 mutation and G-CIMP status were not significant.

TABLE 2

| | Kaplan-Meier | Cox regression | |
|---|---|---|---|
| Total number of samples | 116 | 95 | |
| # Hyper-methylated for ZMIZ1 | 20 | 17 | |
| # Hypo-methylated for ZMIZ1 | 96 | 78 | |
| p-value | 0.007 | ZMIZ1 | 0.066 |
| | | IDH1 | 0.929 |
| | | MGMT | 0.990 |
| | | Sex | 0.442 |
| | | Race | 0.298 |
| | | Age | <0.001 |

In addition, considering that IDH1 mutation is known to cause the G-CIMP phenotype and to confer survival benefit to glioblastoma patients, we excluded cases that harbored IDH1-mutation and analyzed with only the IDH1-WT cases. Again, the hyper-methylated cases showed a statistically significant survival difference compared to the hypo-methylated cases (p=0.048) (FIG. 4). Furthermore, Kaplan-Meier analysis of the same cohort of patients showed statistically significant changes in the variables: progression to death after radiation treatment (p-value: 0.021) and progression to death after chemotherapy (p-value: 0.025).

Regulation and Biological Significance of the Truncated ZMIZ1 Transcript

ZMIZ1 Methylation and Genetics.

Due to the well-known causative relation between IDH1 mutation and genome-wide methylation, we looked more closely into the correlation between IDH1 mutation and ZMIZ1 methylation. An independent dataset (GEO accession: GSE32283) shows that 21 of 26 (81%) IDH1-mutated glioblastoma samples were ZMIZ1 hyper-methylated. Within the same series, 7 cases out of 36 (19.4%) IDH1-wild type (WT) glioblastoma samples were ZMIZ1 hyper-methylated. Furthermore, the methylation analysis of 9 IDH1 and IDH2 WT stem-like glioblastoma cell lines in another independent dataset showed that 7/9 cell lines were ZMIZ1 hyper-methylated. These data show that IDH1 mutation correlates to a limited extent with the methylation of ZMIZ1 and the methylation of ZMIZ1 is conceivably regulated by additional mechanisms. Interestingly, we identified that 70% of glioblastoma samples had "Loss of Heterozygosity (LOH)" for the ZMIZ1 genomic region and a somatic mutation rate smaller than 2% (cBioPortal for Cancer Genomics, Gao et al., Cerami et al.).

In Vitro Mechanistic Studies

Cell Viability, Apoptosis and Proliferation.

Figure 5A:
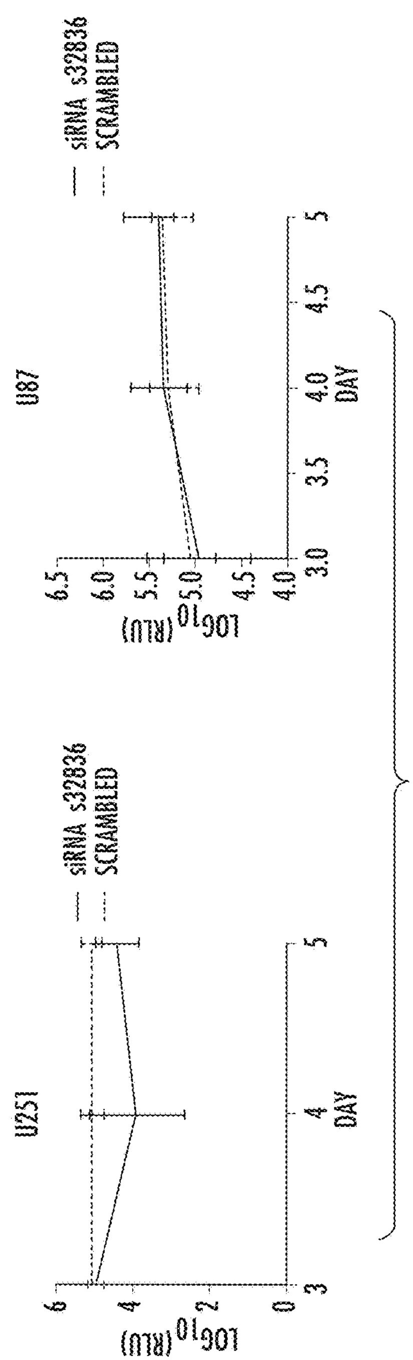
FIG. 5A. Cell titer glo viability assay.
Figure 5B:
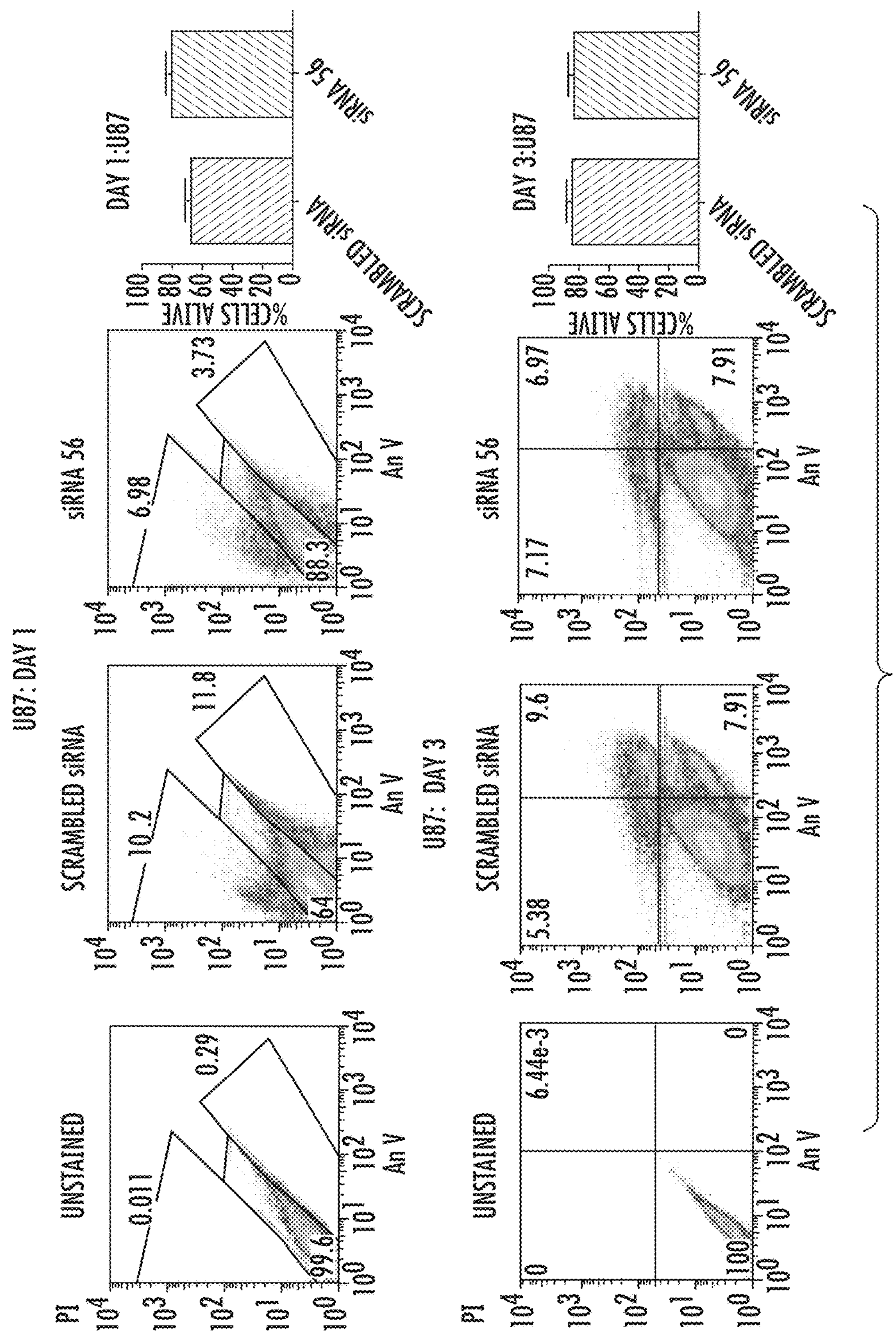
FIG. 5B. Annexin V-PI apoptosis assays.

The effect of knock down of both the full as well as the truncated ZMIZ1 on the viability of GBM cells was assessed with Cell Titer glo after siRNA transfection. We confirmed that knockdown of both full and truncated transcript was sustained for at least 5 days after siRNA transfection. U251 and U87 cell lines exhibited little to no viability differences (FIG. 5A). We also confirmed these results by performing an Annexin/PI apoptosis assay (FIG. 5B).

Figure 6:
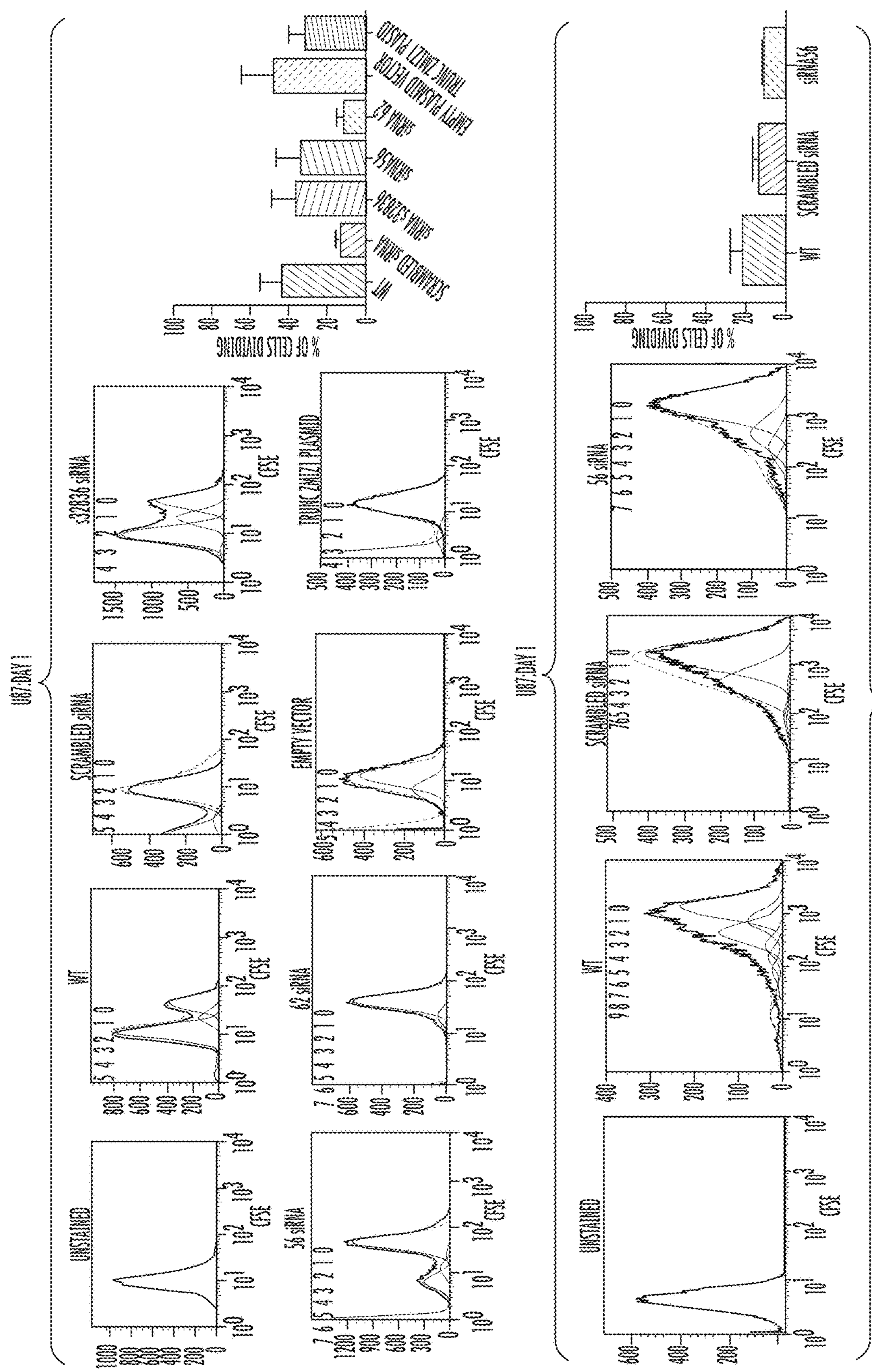
FIG. 6. Gain of function and loss of function studies in U87 and U251 cells labeled with CFSE were performed to assess the effect ZMIZ1 had on the proliferation capacity of glioblastoma cells.

To assess the effect ZMIZ1 had on the proliferation capacity of glioblastoma cells, we performed gain of function and loss of function studies in U87 and U251 cells labelled with CFSE (FIG. 6). 24 hours after transfection, analysis of CFSE intensity showed no statistical difference in the percent of dividing cells among the siRNA, scrambled, empty vector or ZMIZ1 hyper-expressing plasmids.

Migration-Invasion Studies.

Figure 7:
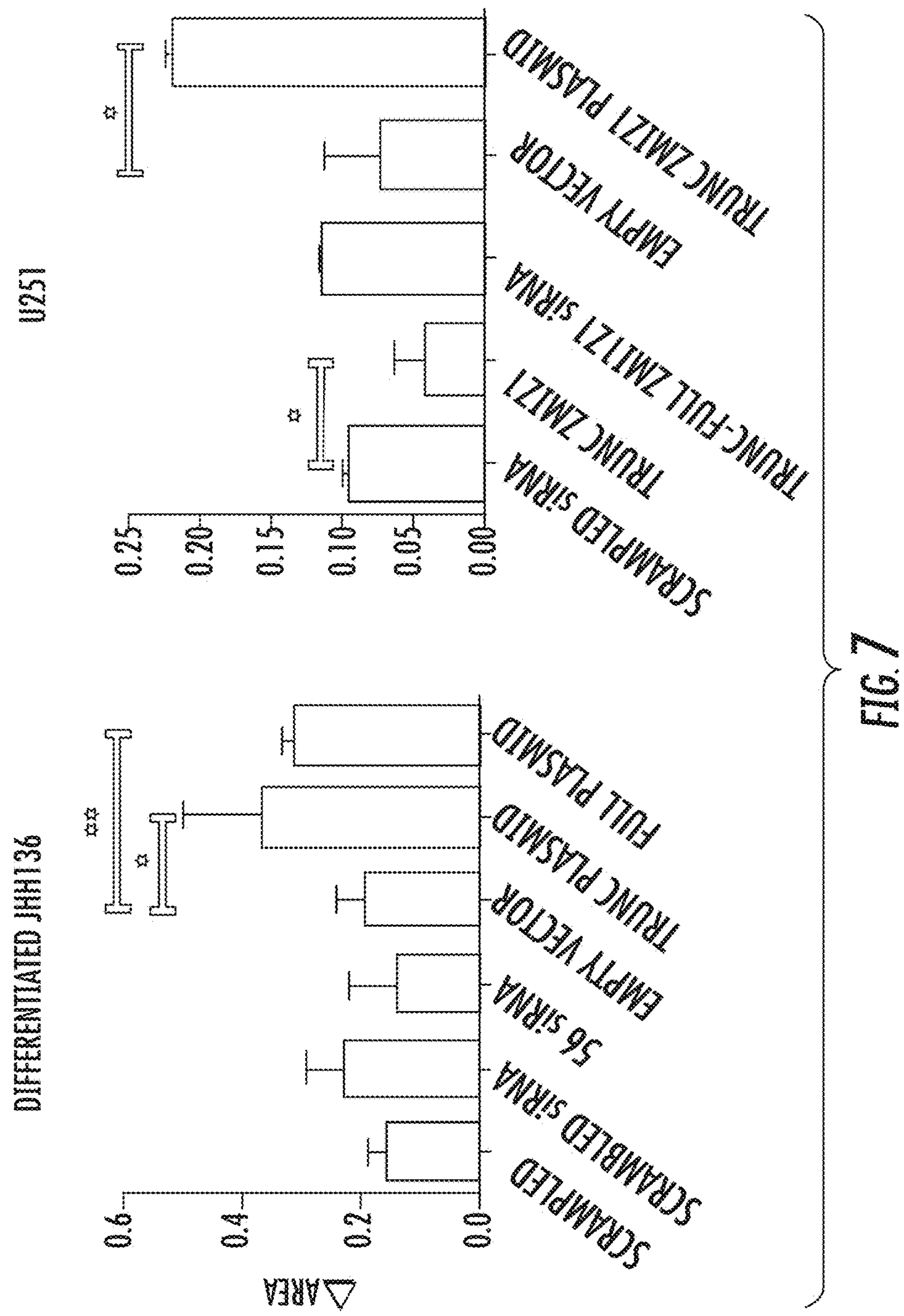
FIG. 7. Migration-invasion experiment.

U251 and LN18 glioblastoma cell lines as well as the differentiated JHH136 CSC-like cell line were transfected with the following agents in separate wells of a 6-well plate: siRNA targeting both the full and truncated ZMIZ1 transcript, siRNA targeting the truncated ZMIZ1 transcript, scrambled siRNA control, plasmid ectopically expressing the full ZMIZ1 transcript, or plasmid ectopically expressing the truncated ZMIZ1 transcript, empty vector plasmid. A scratch test was performed, and an increased migratory potential was exhibited in cells transfected with ZMIZ1 hyperexpressing plasmids while a decreased migratory potential was observed in cells with decreased ZMIZ1 expression (FIG. 7).

In Vitro Treatment with Temozolamide.

Figure 8:
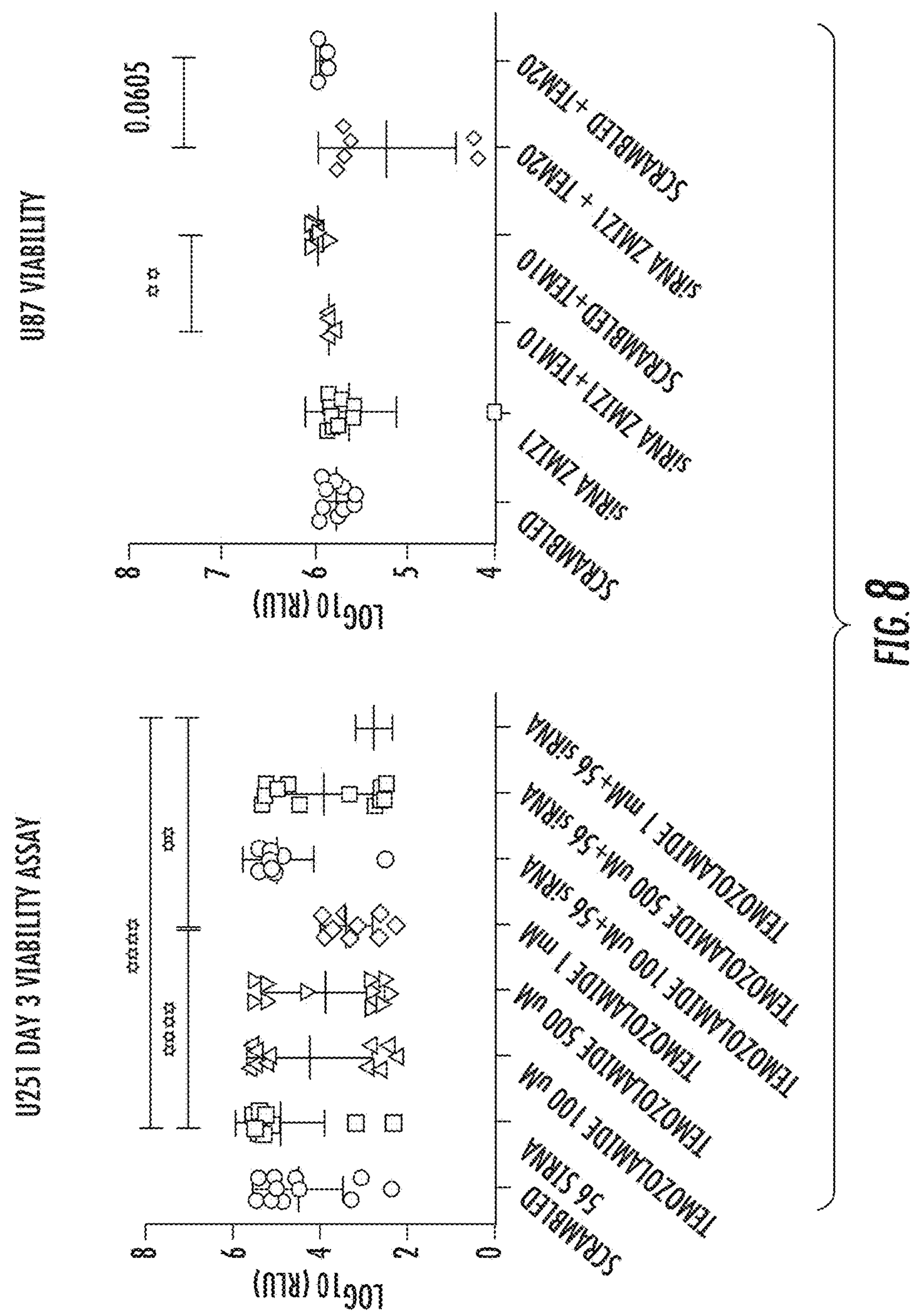
FIG. 8. Cell titer glo viability assay to assess the sensitivity of glioblastoma cell lines to temozolamide and ZMIZ1 knocked-down or -up.

Since temozolamide is the standard of care for Glioblastoma, we assessed whether knocking-down ZMIZ1 would sensitize cells to chemotherapy. Both U251 and U87 cell lines showed decreased viability in response to concomitant treatment with ZMIZ1 siRNA and temozolamide versus the single agent therapy. Three days post treatment, U251 cell line showed a statistically significant decrease in viability when combining 1 mM of temozolamide and 56 siRNA compared to 56 siRNA alone (p<0.0001) or 1 mM temozolamide alone (P<0.01). Three days post treatment, U87, an MGMT hypermethylated cell line, was more sensitive to temozolamide when dosed at either 10 uM or 20 uM in combination with s32836 siRNA than to temozolamide given in combination with scrambled siRNA (p<0.01 and p=0.06 respectively) (FIG. 8).

ZMIZ1 as a Molecular Marker in Multiple Tumor Types

To assess the discriminative survival power of ZMIZ1 as a molecular biomarker we analyzed all tumor types available in TCGA with adequate number of patients whose DNA methylation or RNA expression was assessed with the 450k Infinium array or RNA-sequencing. Analysis of patients with data from only these two platforms was necessary as the 27k Infinium array and current RNA microarray technology cannot capture the molecular signature involved in the truncated form of ZMIZ1.

Low Grade Glioma (LGG).

Figure 9A:
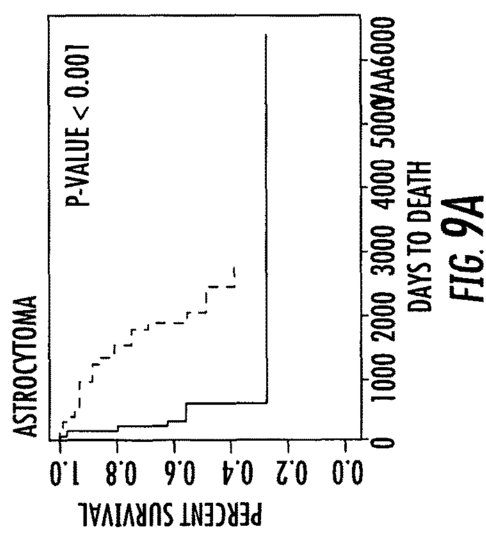
FIG. 9A-9D. ZMIZ1 as a molecular marker in multiple tumor types: astrocytoma (FIG. 9A), BLCA (FIG. 9B), ESCA (FIG. 9C) and KIRC (FIG. 9D).

We extended our analysis of ZMIZ1 methylation status in lower grade gliomas in adult population (Grade II & III). We only included Caucasian samples to exclude any race effect. Astrocytomas (n=143) but not oligodendrogliomas showed survival differences in ZMIZ1 hypermethylated cases (n=104) versus the hypomethylated cases (n=39), independent of the IDH1 status (FIG. 9A, Table 3). More specifically, in a multivariate analysis including age, sex, grade and IDH1 mutation, age was the only statistically significant factor correlating with improved survival in patients with astrocytoma with ZMIZ1 being the second most significant factor but it did not reach statistical significance (P=0.1). When age was excluded from the analysis ZMIZ1 methylation status was the only statistically significant factor (P=0.02) and IDH1 was not statistically significant (P=0.6).

Bladder Urothelial Carcinoma (BLCA).

Figure 9B:
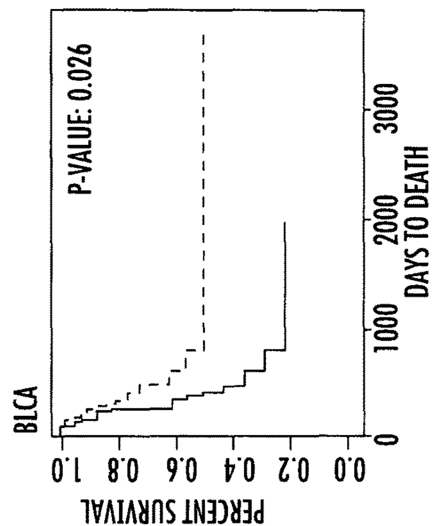

High grade BLCA samples (Grade III and IV) from TCGA showed a bimodal distribution for cg26654807 probe. After classifying the samples into two groups based on the methylation level of the probe, survival analysis was performed for 132 Caucasians. The hyper-methylated group (n=78) showed a significantly better survival than the hypomethylated group (n=54) (P=0.026). In a multivariate analysis including age, gender, tumor stage and tumor grade ZMIZ1 methylation was still an independent predictor of survival (P=0.037) (FIG. 9B, Table 3).

Esophageal Carcinoma (ESCA).

Figure 9C:
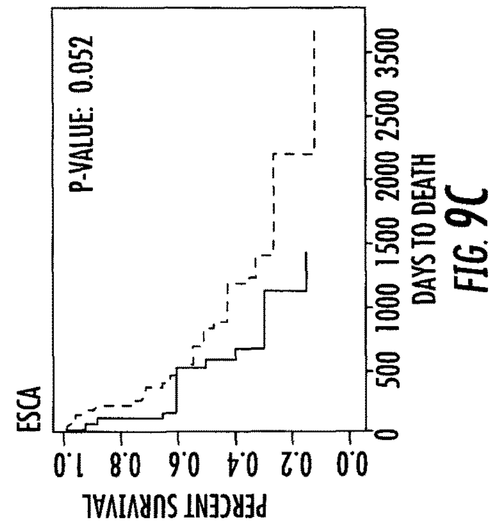

ESCA samples from TCGA (n=202) show a bimodal distribution for the cg26654807 probe. After classifying the samples into two groups based on the methylation level of the probe, survival analysis was performed for 156 classified samples with survival information. The hyper-methylated group (n=88) exhibits a significantly better survival than the hypomethylated group (n=68) (P=0.05, FIG. 9C, Table 3). Lack of additional clinical data in a great portion of this patient cohort prevented us from performing a multivariate analysis.

Kidney Renal Clear Cell Carcinoma (KIRC).

Figure 9D:
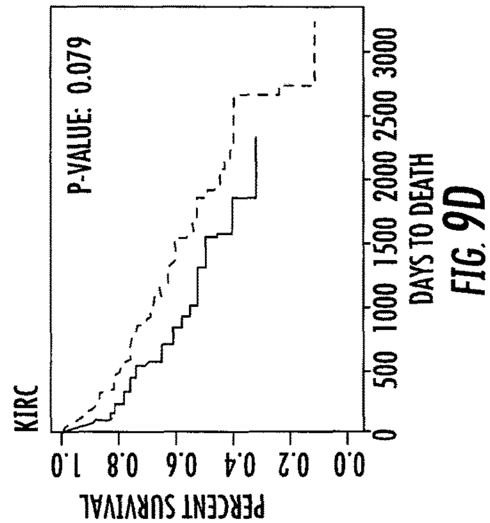

KIRC samples from TCGA (n=480) don't show a bimodal distribution for the cg26654807 probe. However, significant proportion of samples is distributed across a broad range of methylation values. After classifying the samples into two groups based on methylation levels of the probe, survival analysis was performed for 444 Caucasians with survival information. The hypermethylated group (n=387) shows a significantly better survival advantage than the hypomethylated group (n=57) (P=0.079). When controlling for race, age, gender, tumor grade and tumor stage ZMIZ1 methylation turned out to be more significant (P=0.007) than in univariate analysis (FIG. 9D, Table 3).

TABLE 3

| | | Astrocytoma | BLCA | KIRC | ESCA |
|---|---|---|---|---|---|
| Kaplan-Meier | | | | | |
| Total number of samples | | 143 | 132 | 444 | 156 |
| # Hyper-methylated | | 104 | 78 | 387 | 88 |
| # Hypo-methylated | | 39 | 54 | 57 | 68 |
| p-value | | <0.001 | 0.026 | 0.079 | 0.052 |
| Cox regression | | | | | |
| Total number of samples | | 92 | 104 | 427 | Not available |
| # Hyper-methylated | | 68 | 65 | 373 | |
| # Hypo-methylated | | 24 | 39 | 54 | |
| p-value | ZMIZ1 | 0.112 | 0.037 | 0.007 | |
| | Age | 0.046 | 0.351 | <0.001 | |
| | Sex | 0.166 | 0.182 | 0.777 | |
| | Race | 0.936 | NA (CAUC only) | 0.069 | |
| | IDH1 | 0.797 | NA | NA | |
| | Grade | 0.332 | NA (High only) | 0.037 (III), <0.001 (IV) | |
| | Stage | NA | 0.668 (III), 0.155(IV) | 0.874 (II), <0.001 (III), <0.001 (IV) | |

RNA Sequencing Analysis.

Figure 10:
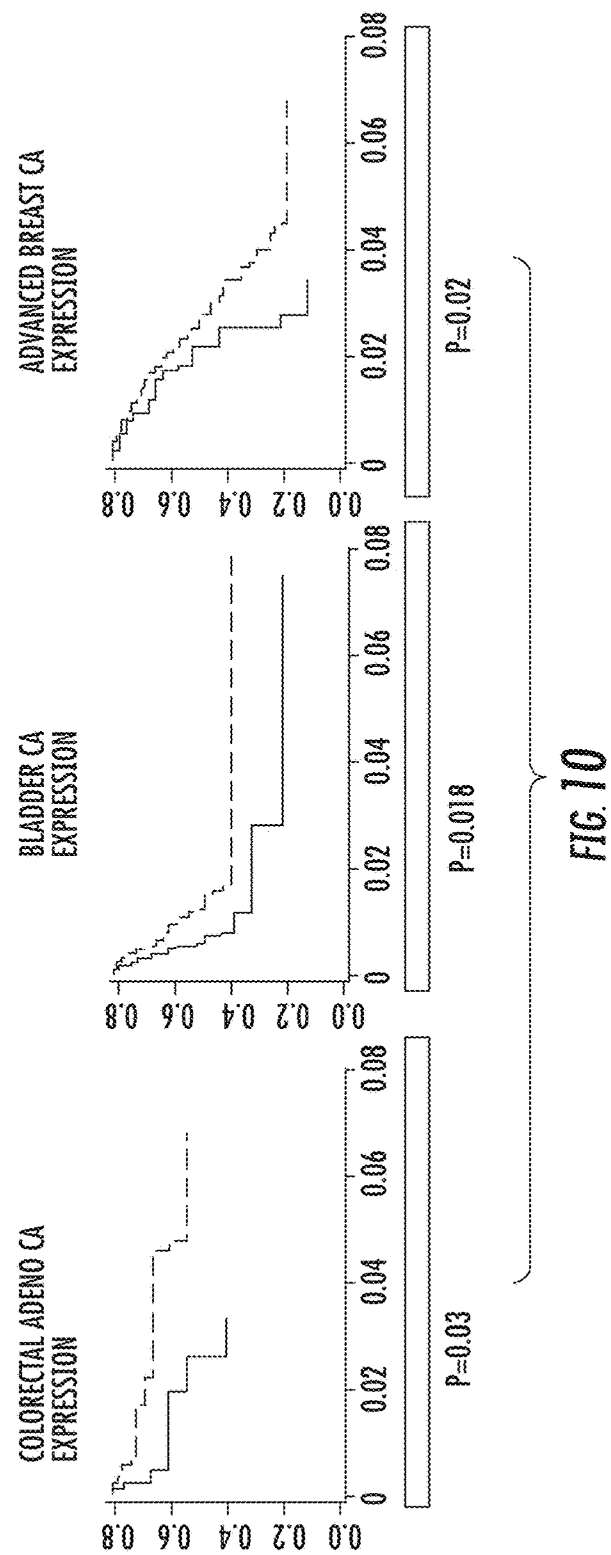
FIG. 10. High expression of the transcript correlated with a statistically significant decrease in patient survival [P=0.02 for breast cancer (n=1134) and P=0.03 for colon adenocarcinoma (n=215).

Analysis of mRNA expression of the truncated ZMIZ1 gene for bladder cancer, colon adenocarcinoma and breast invasive carcinoma proved to show survival differences confirming the clinical value that ZMIZ1 has in cancer as well as implying a significant biological function this gene has in tumor progression. These particular cancer types apart from bladder cancer showed a homogeneous methylation pattern for cg26654807 (hypomethylation for breast cancer and hypermethylation for colon adenocarcinoma) not allowing for classification of these tumors in survival groups based on methylation. As expected, some tumor types are not epigenetically regulating the ZMIZ1 truncated transcript and in these cases it remains to be found how the mRNA transcription is regulated. However, studying the effect high expression of the truncated ZMZI1 transcript has in these tumor types we found out that a high expression of the transcript correlated with a statistically significant decrease in patient survival [P=0.02 for breast cancer (n=1134) and P=0.03 for colon adenocarcinoma (n=215), FIG. 10]. Furthermore, bladder cancer correlated with a statistically significant better survival in patients with lower level of truncated ZMIZ1 transcript (P=0.018), consistent with what we observed for ZMIZ1 methylation and with our hypothesis that high methylation of the alternative promoter of ZMIZ1 correlates with low expression of the pertinent transcript (FIG. 10).

DISCUSSION

Advancements in high-throughput technologies, especially in next-generation sequencing (NGS) has fairly recently revealed that much larger portion of the human genome is transcribed than what was expected before. Many previously known intergenic or intragenic regions are now annotated as transcription units [11]. Additionally, the epigenetic signatures spanning intragenic regions have started to be understood and appreciated more. The intragenic DNA methylation in CGIs is one such signature, which is likely to be associated with alternative transcription. In this study, we systemically searched for biomarkers of cancer patient survival in intragenic regions in terms of gene body methylation. We first evaluated in a whole genome level, the importance of intragenic DNA methylation in the setting of glioblastoma, one of the most aggressive tumor types where the need for biomarkers is of outmost importance. Interestingly, we found that intragenic sites are enriched for highly “variable methylated sites” (sites with high inter-tumoral heterogeneity in methylation across the studied patient population) compared to the 5' promoter gene region and can form a G-CIMP phenotype similarly to what has been described before. These intragenic sites are annotated in areas of active transcription, implying that intragenic methylation can regulate alternative transcription. Based on this evidence we hypothesized that alternative transcripts regulated by intragenic methylation could be used as novel biomarkers of glioblastoma survival. By applying computational filters that would allow us to focus on intragenic sites showing the mixture of distinct DNA methylation in glioblastoma patients, we identified an alternative transcript of ZMIZ1 as a novel biomarker with prognostic significance in glioblastoma. We also discovered that the methylation of the alternative ZMIZ1 transcript can be used as a biomarker of survival in multiple tumor types. Furthermore, RNA expression in cancers that did not seem to be epigenetically regulating the ZMIZ1 gene stratified patients in good and poor prognosis groups. All cancer types available in TCGA with adequate number of patients with methylation and expression data as well as clinical information were assessed for methylation and RNA expression. A total of 1134 advanced breast cancer, 120 Glioblastoma, 330 LGG, 444 KIRC, 395 bladder cancer, 215 colon adenocarcinoma and 202 esophageal cancer samples showed survival differences denoting the prognostic significance of ZMIZ1 in multiple cancer types.

In glioblastoma, MGMT promoter hyper-methylation has been related with positive response to temozolamide treatment. Also, work from the TCGA group has identified key genetic, epigenetic and molecular alterations that have helped classify glioblastoma into distinct subgroups [5, 12]. The proneural molecular subtype as well as the G-CIMP status and IDH1 mutation status have been associated with a better prognosis compared to the rest of the patients. Here, we show that ZMIZ1 methylation status was independently linked to improved survival and superior in comparison with IDH1 mutation status and MGMT methylation status (p-value of ZMIZ1: 0.06, p-value of IDH1: 0.93, p-value of MGMT: 0.99 in Cox regression). ZMIZ1 methylation was not related with any particular molecular subtype (p-value: 0.67) [12]. Interestingly, a great percentage of glioblastoma cases had LOH approaching 80% of all the cases. Glioblastoma is the only tumor type with such a high percent of LOH for the ZMIZ1 region.

The prognostic significance of the truncated ZMIZ1 transcript is further highlighted by its application to multiple tumor types. The truncated ZMIZ1 methylation correlated with statistically different survival in astrocytoma, BLCA, ESCA and KIRC. These results indicate that the truncated ZMIZ1 transcript plays a broad role in cancer development. Rogers et al. have recently identified ZMIZ1 as commonly mutated in squamous cell carcinoma (SCC) in an experimental model of Sleeping Beauty transposon mutagenesis screen [13]. They found out that the mutation inserted by the SB transposon leads to a truncated ZMIZ1 protein that exhibits greater protein stability and half-life and the creation of spontaneous SCC in mice upon ectopic expression. The methylation probe that exhibits a prognostic significance in the tumor types we studied here, corresponds to the CpG island in the alternative promoter of the truncated ZMIZ1 transcript identified in the study by Rogers et al.

The mechanism of regulation of the truncated ZMIZ1 transcript expression, although unknown to its full extend, seems to be mainly regulated via methylation, as the copy number changes, rearrangements and mutations are very low in all cancer types. A low percentage of rearrangements that lead to a fusion protein of ZMIZ1-ABL have been identified as a distinct feature of B cell acute lymphoblastic leukemia. Although ZMIZ1 is a widely unknown protein with very little information available on the protein function, it has been found to be a regulator of SMAD3/4 [14] and TP53 [15], both very important pathways in cancer. The most well-known function of ZMIZ1 is the sumoylation of androgen receptor [16]. Additionally, ZMIZ1 has been shown to interact with the SWI/SNF complex possibly affecting the remodeling of chromatin [17]. Analysis of the functional role of ZMZI1 in glioblastoma cell lines showed an involvement of the gene in the migration/invasion rather than on the viability-apoptosis or the proliferation of cancer cells. Furthermore, we observed a synergistic antiproliferative effect of ZMZI1 knock-down and temozolamide. The role of ZMIZ1 in the normal development seems to involve processes related to vasculogenesis; mice homozygous for a null mutation of ZMIZ1 exhibit embryonal lethality at day 10 due to abnormal vascular development [18]. Analysis of ZMIZ1 deficient tumors in vivo would shed some light on the effect of ZMZI1 in the progression of cancer; if the observations of Beliakoff et al. on mouse embryonic development in the vasculature were confirmed on human tumor development that would give a new target for cancer therapy.

In conclusion, our study shows the importance of intragenic methylation as a regulatory mechanism of alternative transcription and its impact in cancer pathogenesis. This is supported by the discriminative power the methylation of the truncated form of ZMIZ1 has in patient survival in multiple tumor types and the already known experimental finding that the truncated ZMIZ1 transcript creates a more stable protein product than the full length transcript leading to high efficiency of ZMIZ1 gene function [13]. This high efficiency protein can lead to activation of oncogenic pathways and an increase in the migration-invasion of cancer cells making the treatment of these tumors exceedingly difficult. Finally, the importance of this alternative transcript of ZMIZ1 is highlighted by the discriminative power its expression has in the survival of cancer patients in a multitude of human cancer types.

REFERENCES

1. Esteller, M., et al., p14ARF silencing by promoter hypermethylation mediates abnormal intracellular localization of MDM2. Cancer Res, 2001. 61(7): p. 2816-21.
2. Jones, P. A. and S. B. Baylin, The fundamental role of epigenetic events in cancer. Nat Rev Genet, 2002. 3(6): p. 415-28.
3. Stupp, R., et al., Effects of radiotherapy with concomitant and adjuvant temozolomide versus radiotherapy alone on survival in glioblastoma in a randomised phase III study: 5-year analysis of the EORTC-NCIC trial. Lancet Oncol, 2009. 10(5): p. 459-66.
4. Noushmehr, H., et al., Identification of a CpG island methylator phenotype that defines a distinct subgroup of glioma. Cancer Cell, 2010. 17(5): p. 510-22.
5. Brennan, C. W., et al., The somatic genomic landscape of glioblastoma. Cell, 2013. 155(2): p. 462-77.
6. Parsons, D. W., et al., An integrated genomic analysis of human glioblastoma multiforme. Science, 2008. 321 (5897): p. 1807-12.
7. Maunakea, A. K., et al., Conserved role of intragenic DNA methylation in regulating alternative promoters. Nature, 2010. 466(7303): p. 253-7.
8. Maunakea, A. K., et al., Intragenic DNA methylation modulates alternative splicing by recruiting MeCP2 to promote exon recognition. Cell Res, 2013. 23(11): p. 1256-69.
9. Du, P., et al., Comparison of Beta-value and M-value methods for quantifying methylation levels by microarray analysis. BMC Bioinformatics, 2010. 11: p. 587.
10. Bady, P., et al., MGMT methylation analysis of glioblastoma on the Infinium methylation BeadChip identifies two distinct CpG regions associated with gene silencing and outcome, yielding a prediction model for comparisons across datasets, tumor grades, and CIMP-status. Acta Neuropathol, 2012. 124(4): p. 547-60.
11. Illingworth, R. S., et al., Orphan CpG islands identify numerous conserved promoters in the mammalian genome. PLoS Genet, 2010. 6(9): p. e1001134.
12. Verhaak, R. G., et al., Integrated genomic analysis identifies clinically relevant subtypes of glioblastoma characterized by abnormalities in PDGFRA, IDH1, EGFR, and NH. Cancer Cell, 2010. 17(1): p. 98-110.
13. Rogers, L. M., et al., Ectopic expression of Zmiz1 induces cutaneous squamous cell malignancies in a mouse model of cancer. J Invest Dermatol, 2013. 133(7): p. 1863-9.
14. Li, X., et al., The novel PIAS-like protein hZimp10 enhances Smad transcriptional activity. J Biol Chem, 2006. 281(33): p. 23748-56.
15. Lee, J., J. Beliakoff, and Z. Sun, The novel PIAS-like protein hZimp10 is a transcriptional co-activator of the p53 tumor suppressor. Nucleic Acids Res, 2007. 35(13): p. 4523-34.
16. Sharma, M., et al., hZimp10 is an androgen receptor co-activator and forms a complex with SUMO-1 at replication foci. EMBO J, 2003. 22(22): p. 6101-14.
17. Li, X., et al., ZMIZ1 preferably enhances the transcriptional activity of androgen receptor with short polyglutamine tract. PLoS One, 2011. 6(9): p. e25040.
18. Beliakoff, J., et al., The PIAS-like protein Zimp10 is essential for embryonic viability and proper vascular development. Mol Cell Biol, 2008. 28(1): p. 282-92.

We claim:

1. A method for predicting long-term survival of a cancer patient comprising the steps of:

(a) performing polymerase chain reaction (PCR) on nucleic acid isolated from a tumor sample obtained from a human cancer patient to amplify the alternative promoter of the ZMIZ1 gene, wherein the PCR is performed using the primers shown in SEQ ID NOS: 21-22, and wherein the cancer is glioblastoma, lower grade glioma, renal cell carcinoma or bladder cancer;

(b) determining the methylation status of the amplified alternative promoter of the ZMIZ1 gene of step (a); and (c) predicting long-term survival of the cancer patient if the alternative promoter of the ZMIZ1 gene is hypermethylated relative to a control.

* * * * *

SEQUENCE LISTING

```
<160> NUMBER OF SEQ ID NOS: 26

<210> SEQ ID NO 1
<211> LENGTH: 7555
```

<212> TYPE: DNA
<213> ORGANISM: Homo sapiens
<220> FEATURE:
<221> NAME/KEY: misc_feature
<222> LOCATION: (1)..(7555)
<223> OTHER INFORMATION: ZMIZ1 mRNA

<400> SEQUENCE: 1

```
cggcgcgccgg ggagagcggg cggccgggcg gcaggcgggc gagcagcgat cgggcggccg     60
agcgagcgag caacgccggc gcagcgcggt gaccccagcc ccagccggcg cggagcagga    120
gccggagccg agcggatctc ggcgccctcg ctgcgctcct cccggcccga gcctgcccta    180
cccggcggtg gcggcggcgc gtcctccagc ggcggcagcg gcgctcgcag cgcccggact    240
cacggcagct gtgttctgat ttcgtactac tgctggggct gccacctcct cctccagacg    300
ctctcagcag acttgagtcc tggtccttct gcagaggcct gagcaggagg aagaggagga    360
ggcccgttgg cgtcggacca atgctgcaag ggtgtgaggg agaggagccg ctgtttttca    420
ctgagctgcc ataccccgaa agcaggatgg agctggagtg aggtggaggg gccgcaagct    480
gctgaccggc gtgtggaaca ctggtggttt gcagatcact gaggctggac aacgttcatg    540
gctctcgggt agaacctagt gaaacggcca gaatgaattc tatggacagg cacatccagc    600
agaccaatga ccgactgcag tgcatcaagc agcacttaca gaatcctgcc aacttccaca    660
atgccgccac ggagctgctg gactggtgcg gagacccacg ggccttccag cggcccttcg    720
agcagagcct gatgggctgt ttgacggtgg tcagtcgggt ggcagcccag caaggctttg    780
acctggacct cggctacaga ctgctggctg tgtgtgctgc aaaccgagac aagttcaccc    840
cgaagtctgc cgccttgttg tcctcctggt gcgaagagct cggccgcctg ctgctgctcc    900
gacatcagaa gagccgccag agcgatcccc ctgggaaact ccccatgcag ccccctctca    960
gctccatgag ctccatgaaa cccactctgt cgcacagtga tgggtcgttc ccctatgact   1020
ctgtcccttg gcagcagaac accaaccagc ctcccggctc cctttccgtg gtcaccacgg   1080
tttggggagt aaccaacaca tcccagagcc aggtccttgg gaaccctatg gccaatgcca   1140
acaaccccat gaatccaggc ggcaacccca tggcgtcggg catgaccacc agcaacccag   1200
gcctcaactc cccacagttt gcggggcagc agcagcagtt ctcagccaag gctggccccg   1260
ctcagcccta catccagcag agcatgtatg gccggcccaa ctaccccggc agcgggggct   1320
ttggggccag ttaccctggg ggtcctaacg cccccgcagg catgggcatc cctccgcaca   1380
ccaggccgcc tgctgacttc actcagcccg cggcagccgc tgcagcagcg gcagtggcag   1440
cagcagcagc cacagctaca gccacagcca cggccactgt ggcagccctg caggagacac   1500
agaacaagga tataaaccag tatggaccga tgggtcccac ccaggcgtat aacagccaat   1560
tcatgaacca gcccgggccg cgggggcctg cctccatggg ggcagcatg aaccccgcga   1620
gcatggcggc tggcatgacg ccctcgggga tgagcggccc tcccatgggc atgaaccagc   1680
cccggccgcc cggcatcagc ccctttggca cacacgggca gcggatgccc cagcagacct   1740
acccgggccc ccggccccag tcccttccta ttcagaacat aaagaggcca taccctggag   1800
agcccaacta tggaaaccag caatatggac caaacagcca gttccccacc cagccaggcc   1860
agtacccagc ccccaacccc ccgaggccac tcacctcccc caactaccca ggacagagga   1920
tgcccagcca gccgagctcc gggcagtacc cgccccccac ggtcaacatg ggcagtatt   1980
acaagccaga acagtttaat ggacaaaata acacgttctc gggaagcagc tacagtaact   2040
acagccaagg gaatgtcaac aggcctccca ggccggttcc tgtggcaaat taccccccact   2100
```

```
cacctgttcc agggaacccc acaccccccca tgacccctgg gagcagcatc cctccatacc   2160

tgtcccccag ccaagacgtc aaaccaccct tcccgcctga catcaagcca aatatgagcg   2220

ctctgccacc acccccagcc aaccacaatg acgagctgcg gctcacattc cctgtgcggg   2280

atggcgtggt gctggagccc ttccgcctgg agcacaacct ggcggtcagc aaccatgtgt   2340

tccacctgcg gcccacggtc caccagacgc tgatgtggag gtctgacctg gagctgcagt   2400

tcaagtgcta ccaccacgag gaccggcaga tgaacaccaa ctggcccgcc tcggtgcagg   2460

tcagcgtgaa cgccacgccc ctcaccattg agcgcggcga caacaagacc tcccacaagc   2520

ccctgcacct gaagcacgtg tgccagccgg gccgcaacac catccagatc accgtcacgg   2580

cctgctgctg ctcccacctc ttcgtgctgc agctggtaca ccggccctcc gtccgctctg   2640

tgctgcaagg actcctcaag aagcgcctcc tgcccgcaga gcactgtatc acgaaaatca   2700

agcggaattt cagcagcgtg gctgcctcct cgggcaacac gaccctcaac ggggaggatg   2760

gggtggagca gacggccatc aaggtgtctc tgaagtgccc catcacattc cggcgcatcc   2820

agctgcctgc tcgaggacac gattgcaagc atgtgcagtg ctttgatctg gagtcatacc   2880

tgcagctgaa ttgcgagaga gggacctgga ggtgtcctgt gtgcaataaa accgctctgc   2940

tggagggcct ggaggtggat cagtacatgt ggggaatcct gaatgccatc caacactccg   3000

agtttgaaga ggtcaccatc gatcccacgt gcagctggcg gccggtgccc atcaagtcgg   3060

acttacacat caaggacgac cctgatggca tcccctccaa gcggttcaag accatgagtc   3120

ccagccagat gatcatgccc aatgtcatgg agatgatcgc agccctgggc cccggcccgt   3180

cccccctatcc cctcccgcct cccccagggg gcaccaactc caacgactac agcagccaag   3240

gcaacaacta ccaaggccat ggcaactttg acttccccca cgggaaccct ggagggacat   3300

ccatgaatga cttcatgcac gggccccccc agctctccca ccccccggac atgcccaaca   3360

acatggccgc cctcgagaaa cccctcagcc accccatgca ggaaactatg ccacacgctg   3420

gcagctctga ccagccccac ccctccatac aacaaggttt gcacgtacca caccccagca   3480

gccagtcagg gcctccatta catcacagtg gggctcctcc tcctcctcct tcccagcctc   3540

cccggcagcc gccacaggcc gctcccagca gccatccaca cagcgacctg acctttaacc   3600

cctcctcagc cttagagggt caggccggag cgcagggagc gtccgacatg ccggagcctt   3660

cgctggatct ccttcccgaa ctcacaaatc ctgacgagct cctgtcttat ctggaccccc   3720

ccgacctgcc gagcaatagt aacgatgacc tcctgtctct atttgagaac aactgagggc   3780

cacccggtcg gggccatccc tccacactct gcatcctacc ccacctaccc aacacacttt   3840

tccacctggg agcctgtgcc ctcagaccgc cccgcaccag agccacgggc tgtggggcgg   3900

ggagccctcc cccgctgcag ccctctcaga acagaggggt agggagggtg caccagtgca   3960

ccaggaaggc tgtgtgggtc tggagcccac gtcccacctc cacacccttg gcttgggccc   4020

atgcccagcg caggcctgaa gaccaccctc ccgagaggaa ccagcccggt aagagggcac   4080

acgctgatgc ggcttcccgg tccctccgcg tgtgccgatt ccagatgacc ttccagtgtc   4140

cccaaggttc ttccatcttc tagactgtaa ccctgcctcc ctgcttcctg gtccagagcc   4200

tccctccagt gactgtggag cctgagaagg cccccgggcc ccagcatggg ccccgagcct   4260

tggaggagca ctggcagttg gtggcagtga gaccagccca cccaccacca cccaccacag   4320

aaaagcacaa acctctggga aagacaacgt ctctcggggg ccaggggtca tcggtttgac   4380

ccctgaccta taagccaaga taccccataa acacactcag aaagcagaga aaaaggacaa   4440

gagtctgtgt ttgagagggg gtctgccatt cctgcttggg gactggtggg gaagagggcc   4500
```

```
aggacatctt ctgagccagg acgtccctga ggctccacct ccaagctcag acagggccca   4560
ggcttgggga acagagagag caggtgtaca cccaaccaaa gtgattgtgc ccttggttgg   4620
ggggcgcggg catataacct gtcagaagca aacaggagcg gcaacttcta actttgctcc   4680
aagccactct ctttttaaac agcaacaatt taaagctatg aagtcacctg gagaaaagga   4740
acgttgctct tggacagcaa gcaaaccatt tctctccgtc tgttctgttt ttctcctagt   4800
ccctctcctg ccacctctcc aagacttccg tgggacaccc acttccctct gtcctagttc   4860
tctttgtcca atcagatggc aagggcagtg cgtggaaagg ccggggaggt gcagaaacca   4920
gagcccaggg caatggtgtc tgtccagccc ctccctctgt ccctgtgctc caagctgccc   4980
ccggctgcag cccaggccat ggacatgtgc accagtatgt acctgcaggc atgggggga    5040
gggggcgtg tttctgggcc tgccccagac actgcccttg gctgccagcc taccctgcct    5100
gcactcctcc accatcacaa tctcacccaa actcctgctc actcaagcaa aagcagcctc   5160
tggccttccc tccaccgctt tgctccatct ggcttaccac tctccagggc ctcctgggga   5220
gcctgtcctg tgttcacttt gtttcaggct ggtctgtgcc ccgtgagcca catggcctag   5280
ggtgatgcca ggttgtcccg tcactggggt cccatctgta aattctttgc gcccttcccg   5340
gctgctgcct ggggcccttt cctgctctcc cgtccgctgt gggtggtccc cagctctcct   5400
ctgtgggttt taccggaaag gtggccccag ctgttgactt ccagtcactg tcccagacgg   5460
cacaaggttt tctgtaggaa agctgccatt gccccggccc cttttcttcc tttgtcccgt   5520
tgtcgaggtt ttttcaaata gcgtgttgtt cagtatgcaa atcaattatt ttaagaatcg   5580
cttttgtaaa tatctttgtg aatattttag tatcgtcttt gataatattc aacattttca   5640
tgacctggtt atagcctttg ctggtgtttt taaaatacct ggactcaatg acaaagaccg   5700
agtcttcttt ttttttaaac aaaaacaaaa aaagcaacca gggctatttg tacagttgaa   5760
ggggtgaaca gaatgggcgg ctgtgctggg agttggaaga ccgggcagcc cgctatttag   5820
agccatccct cagtcagctg gcagggacaa gccaacgcca ggtagcatgt ggccaccctt   5880
gcccagtgtc tgtggcctgg caagtggcca cgccctgtgt cagaccatct gggaattaag   5940
ctccagacag acttacagat gccttcctta ggagttcttg cttcttgcgt tgatactttg   6000
ccccagaaag gcctgggatt cattctggtt cttatcaggg tgtgtccaca ctctgctcac   6060
aggtggatcc acggctttcc agtgcggaga gtcgagatgc tccctgcagc ccaggccccg   6120
ggcacctcct gcaaccatct ctgggctcag cacctgaggc gggtttcctg ggtcccctct   6180
ccagcaagcc tccaccagca agctcggccc agagcttccc ttccggctgg ctctgaaccg   6240
tgcgtggtgc ctacagcctg cagtctggag acaagctctt ccggagtgct ctgggagcca   6300
ggccagggtg tgagggaggt gcagaggcat ccggggcggg agcaagcccc aggttgtgac   6360
aggtgcaggt agacaacgcc cataaacaga gatggtcctg aactctggag agatccttcc   6420
ctgatccttt cggacgacta cttggagcca taagtaacct cagcaaaaac gaggcctctg   6480
caagccactt ttccatgcca agcatccacc cggcccacag gcatgtttct gccgccactc   6540
cgcaagatgg acagggagcc agcaggcagg cgggaagggc caagtacagg caatcacccc   6600
catcttcttg gtttgaagct ttatccatgt atcatgttcc gtgtagccat tttatttttt   6660
aagaaactgc taatactttc tccctaatgg aagccctgat cccccagaga gctacaggtc   6720
tgctcccgac gggcctcggg cctgacccgt ccacacaggg ccgtgtcaac agcagcgact   6780
caagggacgt gtgtacatat gtaaatgaga aatagagacg tgtcaacaga tgcattcatt   6840
```

```
tctcttggaa tgtgtattgt ttttattttg cgaaacaaaa caaaacaaaa aaaaaagctt   6900
ggaactccat cacgtggaaa aactagatcc tgttggttat agcatttgtg agttctccac   6960
gtctgtctct ctcgctcatg taatatactc tgaccctgag tggaaagggg tttttgttct   7020
gtttttattt tacctacatg tactatttag cttcagtgta ctagtcctgc cacctgtgta   7080
tttttagggt gctatggaaa taatgaaaag aaacggggat ttcagaagaa aattgtaacc   7140
aaattcatac tttgtataat ttttgatatc atgatcacag gtgattcaca cgtacacaca   7200
taaacacacc caccagtgca gcctgaagta actcccacag aaaccatcat cgtctttgta   7260
catcgtatgt acaatgcaat catttcatac tttaaactgg tcaaaaaact aattgtgatt   7320
tctagtcttg caaagctgta tgtagttaga tgatgtgaca acctctaata tttatctaat   7380
aaatatgtat tcagatgaaa cctgtatatt aggtgttcat gtggttattt tgtatttaaa   7440
gatcaaatta tttgactatt gctagacatt tctatactct gttgtaacac tgaggtatct   7500
catttgccca tgttaatttt tttctaaata aattgacaaa aacaaaggtt tggcg        7555
```

<210> SEQ ID NO 2
<211> LENGTH: 1067
<212> TYPE: PRT
<213> ORGANISM: Homo sapiens
<220> FEATURE:
<221> NAME/KEY: MISC_FEATURE
<222> LOCATION: (1)..(1067)
<223> OTHER INFORMATION: ZMIZ1 amino acid sequence

<400> SEQUENCE: 2

```
Met Asn Ser Met Asp Arg His Ile Gln Gln Thr Asn Asp Arg Leu Gln
1               5                   10                  15

Cys Ile Lys Gln His Leu Gln Asn Pro Ala Asn Phe His Asn Ala Ala
            20                  25                  30

Thr Glu Leu Leu Asp Trp Cys Gly Asp Pro Arg Ala Phe Gln Arg Pro
        35                  40                  45

Phe Glu Gln Ser Leu Met Gly Cys Leu Thr Val Val Ser Arg Val Ala
    50                  55                  60

Ala Gln Gln Gly Phe Asp Leu Asp Leu Gly Tyr Arg Leu Leu Ala Val
65                  70                  75                  80

Cys Ala Ala Asn Arg Asp Lys Phe Thr Pro Lys Ser Ala Ala Leu Leu
                85                  90                  95

Ser Ser Trp Cys Glu Glu Leu Gly Arg Leu Leu Leu Leu Arg His Gln
            100                 105                 110

Lys Ser Arg Gln Ser Asp Pro Pro Gly Lys Leu Pro Met Gln Pro Pro
        115                 120                 125

Leu Ser Ser Met Ser Ser Met Lys Pro Thr Leu Ser His Ser Asp Gly
    130                 135                 140

Ser Phe Pro Tyr Asp Ser Val Pro Trp Gln Gln Asn Thr Asn Gln Pro
145                 150                 155                 160

Pro Gly Ser Leu Ser Val Val Thr Thr Val Trp Gly Val Thr Asn Thr
                165                 170                 175

Ser Gln Ser Gln Val Leu Gly Asn Pro Met Ala Asn Ala Asn Asn Pro
            180                 185                 190

Met Asn Pro Gly Gly Asn Pro Met Ala Ser Gly Met Thr Thr Ser Asn
        195                 200                 205

Pro Gly Leu Asn Ser Pro Gln Phe Ala Gly Gln Gln Gln Gln Phe Ser
    210                 215                 220

Ala Lys Ala Gly Pro Ala Gln Pro Tyr Ile Gln Gln Ser Met Tyr Gly
```

```
225                 230                 235                 240

Arg Pro Asn Tyr Pro Gly Ser Gly Gly Phe Gly Ala Ser Tyr Pro Gly
                245                 250                 255

Gly Pro Asn Ala Pro Ala Gly Met Gly Ile Pro Pro His Thr Arg Pro
            260                 265                 270

Pro Ala Asp Phe Thr Gln Pro Ala Ala Ala Ala Ala Ala Ala Ala Val
        275                 280                 285

Ala Ala Ala Ala Ala Thr Ala Thr Ala Thr Ala Thr Ala Thr Val Ala
    290                 295                 300

Ala Leu Gln Glu Thr Gln Asn Lys Asp Ile Asn Gln Tyr Gly Pro Met
305                 310                 315                 320

Gly Pro Thr Gln Ala Tyr Asn Ser Gln Phe Met Asn Gln Pro Gly Pro
                325                 330                 335

Arg Gly Pro Ala Ser Met Gly Gly Ser Met Asn Pro Ala Ser Met Ala
            340                 345                 350

Ala Gly Met Thr Pro Ser Gly Met Ser Gly Pro Pro Met Gly Met Asn
        355                 360                 365

Gln Pro Arg Pro Pro Gly Ile Ser Pro Phe Gly Thr His Gly Gln Arg
    370                 375                 380

Met Pro Gln Gln Thr Tyr Pro Gly Pro Arg Pro Gln Ser Leu Pro Ile
385                 390                 395                 400

Gln Asn Ile Lys Arg Pro Tyr Pro Gly Glu Pro Asn Tyr Gly Asn Gln
                405                 410                 415

Gln Tyr Gly Pro Asn Ser Gln Phe Pro Thr Gln Pro Gly Gln Tyr Pro
            420                 425                 430

Ala Pro Asn Pro Pro Arg Pro Leu Thr Ser Pro Asn Tyr Pro Gly Gln
        435                 440                 445

Arg Met Pro Ser Gln Pro Ser Ser Gly Gln Tyr Pro Pro Pro Thr Val
    450                 455                 460

Asn Met Gly Gln Tyr Tyr Lys Pro Glu Gln Phe Asn Gly Gln Asn Asn
465                 470                 475                 480

Thr Phe Ser Gly Ser Ser Tyr Ser Asn Tyr Ser Gln Gly Asn Val Asn
                485                 490                 495

Arg Pro Pro Arg Pro Val Pro Val Ala Asn Tyr Pro His Ser Pro Val
            500                 505                 510

Pro Gly Asn Pro Thr Pro Pro Met Thr Pro Gly Ser Ser Ile Pro Pro
        515                 520                 525

Tyr Leu Ser Pro Ser Gln Asp Val Lys Pro Pro Phe Pro Pro Asp Ile
    530                 535                 540

Lys Pro Asn Met Ser Ala Leu Pro Pro Pro Pro Ala Asn His Asn Asp
545                 550                 555                 560

Glu Leu Arg Leu Thr Phe Pro Val Arg Asp Gly Val Val Leu Glu Pro
                565                 570                 575

Phe Arg Leu Glu His Asn Leu Ala Val Ser Asn His Val Phe His Leu
            580                 585                 590

Arg Pro Thr Val His Gln Thr Leu Met Trp Arg Ser Asp Leu Glu Leu
        595                 600                 605

Gln Phe Lys Cys Tyr His His Glu Asp Arg Gln Met Asn Thr Asn Trp
    610                 615                 620

Pro Ala Ser Val Gln Val Ser Val Asn Ala Thr Pro Leu Thr Ile Glu
625                 630                 635                 640

Arg Gly Asp Asn Lys Thr Ser His Lys Pro Leu His Leu Lys His Val
                645                 650                 655
```

```
Cys Gln Pro Gly Arg Asn Thr Ile Gln Ile Thr Val Thr Ala Cys Cys
            660                 665                 670

Cys Ser His Leu Phe Val Leu Gln Leu Val His Arg Pro Ser Val Arg
        675                 680                 685

Ser Val Leu Gln Gly Leu Leu Lys Lys Arg Leu Leu Pro Ala Glu His
    690                 695                 700

Cys Ile Thr Lys Ile Lys Arg Asn Phe Ser Ser Val Ala Ala Ser Ser
705                 710                 715                 720

Gly Asn Thr Thr Leu Asn Gly Glu Asp Gly Val Glu Gln Thr Ala Ile
                725                 730                 735

Lys Val Ser Leu Lys Cys Pro Ile Thr Phe Arg Arg Ile Gln Leu Pro
            740                 745                 750

Ala Arg Gly His Asp Cys Lys His Val Gln Cys Phe Asp Leu Glu Ser
        755                 760                 765

Tyr Leu Gln Leu Asn Cys Glu Arg Gly Thr Trp Arg Cys Pro Val Cys
    770                 775                 780

Asn Lys Thr Ala Leu Leu Glu Gly Leu Glu Val Asp Gln Tyr Met Trp
785                 790                 795                 800

Gly Ile Leu Asn Ala Ile Gln His Ser Glu Phe Glu Glu Val Thr Ile
                805                 810                 815

Asp Pro Thr Cys Ser Trp Arg Pro Val Pro Ile Lys Ser Asp Leu His
            820                 825                 830

Ile Lys Asp Asp Pro Asp Gly Ile Pro Ser Lys Arg Phe Lys Thr Met
        835                 840                 845

Ser Pro Ser Gln Met Ile Met Pro Asn Val Met Glu Met Ile Ala Ala
    850                 855                 860

Leu Gly Pro Gly Pro Ser Pro Tyr Pro Leu Pro Pro Pro Pro Gly Gly
865                 870                 875                 880

Thr Asn Ser Asn Asp Tyr Ser Ser Gln Gly Asn Asn Tyr Gln Gly His
                885                 890                 895

Gly Asn Phe Asp Phe Pro His Gly Asn Pro Gly Gly Thr Ser Met Asn
            900                 905                 910

Asp Phe Met His Gly Pro Pro Gln Leu Ser His Pro Pro Asp Met Pro
        915                 920                 925

Asn Asn Met Ala Ala Leu Glu Lys Pro Leu Ser His Pro Met Gln Glu
    930                 935                 940

Thr Met Pro His Ala Gly Ser Ser Asp Gln Pro His Pro Ser Ile Gln
945                 950                 955                 960

Gln Gly Leu His Val Pro His Pro Ser Ser Gln Ser Gly Pro Pro Leu
                965                 970                 975

His His Ser Gly Ala Pro Pro Pro Pro Pro Ser Gln Pro Pro Arg Gln
            980                 985                 990

Pro Pro Gln Ala Ala Pro Ser Ser  His Pro His Ser Asp  Leu Thr Phe
        995                 1000                1005

Asn Pro  Ser Ser Ala Leu Glu  Gly Gln Ala Gly Ala  Gln Gly Ala
    1010                1015                1020

Ser Asp  Met Pro Glu Pro Ser  Leu Asp Leu Leu Pro  Glu Leu Thr
    1025                1030                1035

Asn Pro  Asp Glu Leu Leu Ser  Tyr Leu Asp Pro Pro  Asp Leu Pro
    1040                1045                1050

Ser Asn  Ser Asn Asp Asp Leu  Leu Ser Leu Phe Glu  Asn Asn
    1055                1060                1065
```

<210> SEQ ID NO 3
<211> LENGTH: 2196
<212> TYPE: DNA
<213> ORGANISM: Homo sapiens
<220> FEATURE:
<221> NAME/KEY: misc_feature
<222> LOCATION: (1)..(2196)
<223> OTHER INFORMATION: ZMIZ1 mRNA transcript encoding 228 amino acid protein

<400> SEQUENCE: 3

```
ttcatggctc tcgggtagaa cctagtgaaa cggccagaat gaattctatg gacaggcaca     60

tccagcagac caatgaccga ctgcagtgca tcaagcagca cttacagaat cctgccaact    120

tccacaatgc cgccacggag ctgctggact ggtgcggaga cccacgggcc ttccagcggc    180

ccttcgagca gagcctgatg ggctgtttga cggtggtcag tcgggtggca gcccagcaag    240

gctttgacct ggacctcggc tacagactgc tggctgtgtg tgctgcaaac cgagacaagt    300

tcaccccgaa gtctgccgcc ttgttgtcct cctggtgcga agagctcggc cgcctgctgc    360

tgctccgaca tcagaagagc cgccagagcg atccccctgg gaaactcccc atgcagcccc    420

ctctcagctc catgagctcc atgaaaccca ctctgtcgca cagtgatggg tcgttcccct    480

atgactctgt cccttggctg ccagcctacc ctgcctgcac tcctccacca tcacaatctc    540

acccaaactc ctgctcactc aagcaaaagc agcctctggc cttccctcca ccgctttgct    600

ccatctggct taccactctc cagggcctcc tggggagcct gtcctgtgtt cactttgttt    660

caggctggtc tgtgccccgt gagccacatg gcctagggtg atgccaggtt gtcccgtcac    720

tggggtccca tctgtaaatt ctttgcgccc ttcccggctg ctgcctgggg ccctttcctg    780

ctctcccgtc cgctgtgggt ggtccccagc tctcctctgt gggttttacc ggaaaggtgg    840

ccccagctgt tgacttccag tcactgtccc agacggcaca aggttttctg taggaaagct    900

gccattgccc cggccccttt tcttcctttg tcccgttgtc gaggtttttt caaatagcgt    960

gttgttcagt atgcaaatca attattttaa gaatcgcttt tgtaaatatc tttgtgaata   1020

ttttagtatc gtctttgata atattcaaca ttttcatgac ctggttatag cctttgctgg   1080

tgtttttaaa atacctggac tcaatgacaa agaccgagtc ttcttttttt ttaaacaaaa   1140

acaaaaaaag caaccaggc tatttgtaca gttgaagggg tgaacagaat gggcggctgt    1200

gctgggagtt ggaagaccgg gcagcccgct atttagagcc atccctcagt cagctggcag   1260

ggacaagcca acgccaggta gcatgtggcc acccttgccc agtgtctgtg gcctggcaag   1320

tggccacgcc ctgtgtcaga ccatctggga attaagctcc agacagactt acagatgcct   1380

tccttaggag ttcttgcttc ttgcgttgat actttgcccc agaaaggcct gggattcatt   1440

ctggttctta tcagggtgtg tccacactct gctcacaggt ggatccacgg ctttccagtg   1500

cggagagtcg agatgctccc tgcagcccag gccccgggca cctcctgcaa ccatctctgg   1560

gctcagcacc tgaggcgggt ttcctgggtc ccctctccag caagcctcca ccagcaagct   1620

cggcccagag cttcccttcc ggctggctct gaaccgtgcg tggtgcctac agcctgcagt   1680

ctggagacaa gctcttccgg agtgctctgg gagccaggcc agggtgtgag ggaggtgcag   1740

aggcatccgg ggcgggagca agccccaggt tgtgacaggt gcaggtagac aacgcccata   1800

aacagagatg gtcctgaact ctggagagat ccttccctga tcctttcgga cgactacttg   1860

gagccataag taacctcagc aaaaacgagg cctctgcaag ccacttttcc atgccaagca   1920

tccacccggc ccacaggcat gtttctgccg ccactccgca agatggacag ggagccagca   1980
```

```
ggcaggcggg aagggccaag tacaggcaat cacccccatc ttcttggttt gaagctttat   2040

ccatgtatca tgttccgtgt agccatttta ttttttaaga aactgctaat actttctccc   2100

taatggaagc cctgatcccc cagagagcta caggtctgct cccgacgggc ctcgggcctg   2160

acccgtccac acagggccgt gtcaacagca gcgact                             2196


<210> SEQ ID NO 4
<211> LENGTH: 220
<212> TYPE: PRT
<213> ORGANISM: Homo sapiens
<220> FEATURE:
<221> NAME/KEY: MISC_FEATURE
<222> LOCATION: (1)..(220)
<223> OTHER INFORMATION: ZMIZ1 228 amino acid protein

<400> SEQUENCE: 4

Met Asn Ser Met Asp Arg His Ile Gln Gln Thr Asn Asp Arg Leu Gln
1               5                   10                  15

Cys Ile Lys Gln His Leu Gln Asn Pro Ala Asn Phe His Asn Ala Ala
            20                  25                  30

Thr Glu Leu Leu Asp Trp Cys Gly Asp Pro Arg Ala Phe Gln Arg Pro
        35                  40                  45

Phe Glu Gln Ser Leu Met Gly Cys Leu Thr Val Val Ser Arg Val Ala
    50                  55                  60

Ala Gln Gln Gly Phe Asp Leu Asp Leu Gly Tyr Arg Leu Leu Ala Val
65                  70                  75                  80

Cys Ala Ala Asn Arg Asp Lys Phe Thr Pro Lys Ser Ala Ala Leu Leu
                85                  90                  95

Ser Ser Trp Cys Glu Glu Leu Gly Arg Leu Leu Leu Leu Arg His Gln
            100                 105                 110

Lys Ser Arg Gln Ser Asp Pro Pro Gly Lys Leu Pro Met Gln Pro Pro
        115                 120                 125

Leu Ser Ser Met Ser Ser Met Lys Pro Thr Leu Ser His Ser Asp Gly
    130                 135                 140

Ser Phe Pro Tyr Asp Ser Val Pro Trp Leu Pro Ala Tyr Pro Ala Cys
145                 150                 155                 160

Thr Pro Pro Pro Ser Gln Ser His Pro Asn Ser Cys Ser Leu Lys Gln
                165                 170                 175

Lys Gln Pro Leu Ala Phe Pro Pro Pro Leu Cys Ser Ile Trp Leu Thr
            180                 185                 190

Thr Leu Gln Gly Leu Leu Gly Ser Leu Ser Cys Val His Phe Val Ser
        195                 200                 205

Gly Trp Ser Val Pro Arg Glu Pro His Gly Leu Gly
    210                 215                 220


<210> SEQ ID NO 5
<211> LENGTH: 6686
<212> TYPE: DNA
<213> ORGANISM: Homo sapiens
<220> FEATURE:
<221> NAME/KEY: misc_feature
<222> LOCATION: (1)..(6686)
<223> OTHER INFORMATION: ZMIZ1 mRNA transcript encoding 968 amino acid
      protein.

<400> SEQUENCE: 5

atgaggttgc tgaggcatac agagagtgag cagtggtttc atcgcttccc tctgtgtcct     60

tctctcactt tctgggcccc agtggccatg tggccacaga cacactgtgt aggtggtcgg    120
```

```
tcatcaggct taacgaaatg gacatattca ttttcagcat cactccaaga tgggtcgttc    180
ccctatgact ctgtcccttg gcagcagaac accaaccagc ctcccggctc cctttccgtg    240
gtcaccacgg tttggggagt aaccaacaca tcccagagcc aggctgacgt tctcatcccc    300
cacgccacct gccgcccagg cccgctcctt atcagtcctt gggaacccta tggccaatgc    360
caacaacccc atgaatccag gcggcaaccc catggcgtcg ggcatgacca ccagcaaccc    420
aggcctcaac tccccacagt ttgcggggca gcagcagcag ttctcagcca aggctggccc    480
cgctcagccc tacatccagc agagcatgta tggccggccc aactaccccg gcagcggggg    540
ctttggggcc agcccgcggc agccgctgca gcagcggcag tggcagcagc agcagccaca    600
gctacagcca cagccacggc cactgtggca gccctgcagg agacacagaa caaggatata    660
aaccagtatg gaccggcccc agtgctgctc cctgaccttc tgaaggatgg gttaggggat    720
gaggagaggg gagcccccat aggaatgcag aacaggagga accccgcgag catggcggct    780
ggcatgacgc cctcggggat gagcggccct cccatgggca tgaaccagcc ccggccgccc    840
ggcatcagcc cctttggcac acacgggcag cggatgcccc agcagaccta cccgggcccc    900
cggccccagt cccttcctat tcagaacata aagaggccat accctggaga gcccaactat    960
ggaaaccagc aatatggacc aaacagccag ttccccaccc agccaggcca gtacccagcc   1020
cccaaccccc cgaggccact cacctccccc aactacccag gacagaggat gcccagccag   1080
ccgagctccg ggcagtaccc gcccccccacg gtcaacatgg ggcagtatta caagccagaa   1140
cagtttaatg gacaaaataa cacgttctcg ggaagcagct acagtaacta cagccaaggg   1200
aatgtcaaca ggcctcccag gccggttcct gtggcaaatt acccccactc acctgttcca   1260
gggaacccca caccccccat gacccctggg agcagcatcc ctccatacct gtcccccagc   1320
caagacgtca aaccaccctt cccgcctgac atcaagccaa atatgagcgc tctgccacca   1380
cccccagacc acaatgacga gctgcggctc acattccctg tgcgggatgg cgtggtgctg   1440
gagcccttcc gcctggagca caacctggcg gtcagcaacc atgtgttcca cctgcggccc   1500
acggtccacc agacgctgat gtggtctgac ctggagctgc agttcaagtg ctaccaccac   1560
gaggaccggc agatgaacac caactggccc gcctcggtgc aggtcagcgt gaacgccacg   1620
cccctcacca ttgagcgcgg cgacaacaag acctcccaca agcccctgca cctgaagcac   1680
gtgtgccagc cgggccgcaa caccatccag atcaccgtca cggcctgctg ctgctcccac   1740
ctcttcgtgc tgcagctggt acaccggccc tccgtccgct ctgtgctgca aggactcctc   1800
aagaagcgcc tcctgcccgc agagcactgt atcacgaaaa agcggaattt cagcagcgtg   1860
gctgcctcct cgggcaacac gaccctcaac ggggaggatg gggtggagca gacggccatc   1920
aaggtgtctc tgaagtgccc catcacattc cggcgcatcc agctgcctgc tcgaggacac   1980
gattgcaagc atgtgcagtg ctttgatctg gagtcatacc tgcagctgaa ttgcgagaga   2040
gggacctgga ggtgtcctgt gtgcaaaacc gctctgctgg agggcctgga ggtggatcag   2100
tacatgtggg gaatcctgaa tgccatccaa cacgagtttg aagaggtcac catcgatccc   2160
acgtgcagct ggcggccggt gcccatcaag tcggacttac acatcaagga cgaccctgat   2220
ggcatcccct ccaagcggtt caagaccatg agtcccagcc agatgatcat gcccaatgtc   2280
atggagatga tcgcagccct gggccccggc ccgtcccccct atcccctccc gcctccccca   2340
gggggcacca actccaacga ctacagcagc caagacaact accaaggcca tggcaacttt   2400
gacttccccc acgggaaccc tggagggaca tccatgaatg acttcatgca cgggcccccc   2460
cagctctccc acccccccgga catgcccaac aacatggccg ccctcgagaa acccctcagc   2520
```

```
caccccatgc aggaaactat gccacacgct ggcagctctg accagcccca cccctccata   2580
caacaaggtt tgcacgtacc acaccccagc agccagtcag ggcctccatt acatcacagt   2640
ggggctcctc ctcctcctcc ttcccagcct ccccggcagc cgccacaggc cgctcccagc   2700
agccatccac acagcgacct gacctttaac cctcctcag ccttagaggg tcaggccgga   2760
gcgcagggag cgtccgacat gccggagcct tcgctggatc tccttcccga actcacaaat   2820
cctgacgagc tcctgtctta tctggacccc cccgacctgc cgagcaatag taacgatgac   2880
ctcctgtctc tatttgagaa caactgaggg ccacccggtc ggggccatcc ctccacactc   2940
tgcatcctac cccacctacc caacacactt ttccacctgg gagcctgtgc cctcagaccg   3000
ccccgcacca gagccacggg ctgtggggcg gggagccctc ccccgctgca gccctctcag   3060
aacagagggg tagggagggt gcaccagtgc accaggaagg ctgtgtgggt ctggagccca   3120
cgtcccacct ccacaccctt ggcttgggcc catgcccagc gcaggcctga agaccacccct   3180
cccgagagga accagcccgg taagagggca cacgctgatg cggcttcccg gtccctccgc   3240
gtgtgccgat tccagatgac cttccagtgt ccccaaggtt cttccatctt ctagactgta   3300
accctgcctc cctgcttcct ggtccagagc ctccctccag tgactgtgga gcctgagaag   3360
gcccccgggc cccagcatgg gccccgagcc ttggaggagc actggcagtt ggtggcagtg   3420
agaccagccc acccaccacc acccaccaca gaaaagcaca aacctctggg aaagacaacg   3480
tctctcgggg gccaggggtc atcggtttga cccctgacct ataagccaag ataccccata   3540
aacacactca gaaagcagag aaaaaggaca agagtctgtg tttgagaggg ggtctgccat   3600
tcctgcttgg ggactggtgg ggaagagggc caggacatct tctgagccag gacgtccctg   3660
aggctccacc tccaagctca gacagggccc aggcttgggg aacagagaga gcaggtgtac   3720
acccaaccaa agtgattgtg cccttggttg gggggcgcgg gcatataacc tgtcagaagc   3780
aaacaggagc ggcaacttct aactttgctc caagccactc tctttttaaa cagcaacaat   3840
ttaaagctat gaagtcacct ggagaaaagg aacgttgctc ttggacagca agcaaaccat   3900
ttctctccgt ctgttctgtt tttctcctag tccctctcct gccacctctc caagacttcc   3960
gtgggacacc cacttccctc tgtcctagtt ctctttgtcc aatcagatgg caagggcagt   4020
gcgtggaaag gccggggagg tgcagaaacc agagcccagg gcaatggtgt ctgtccagcc   4080
cctccctctg tccctgtgct ccaagctgcc cccggctgca gcccaggcca tggacatgtg   4140
caccagtatg tacctgcagg catggggggg agggggcgt gtttctgggc ctgccccaga   4200
cactgccctt ggctgccagc ctaccctgcc tgcactcctc caccatcaca atctcaccca   4260
aactcctgct cactcaagca aaagcagcct ctggccttcc ctccaccgct ttgctccatc   4320
tggcttacca ctctccaggg cctcctgggg agcctgtcct gtgttcactt tgtttcaggc   4380
tggtctgtgc cccgtgagcc acatggccta gggtgatgcc aggttgtccc gtcactgggg   4440
tcccatctgt aaattctttg cgcccttccc ggctgctgcc tggggccctt tcctgctctc   4500
ccgtccgctg tgggtggtcc ccagctctcc tctgtgggtt ttaccggaaa ggtggcccca   4560
gctgttgact tccagtcact gtcccagacg gcacaaggtt ttctgtagga aagctgccat   4620
tgccccggcc cctttcttc ctttgtcccg ttgtcgaggt tttttcaaat agcgtgttgt   4680
tcagtatgca aatcaattat tttaagaatc gcttttgtaa atatctttgt gaatatttta   4740
gtatcgtctt tgataatatt caacattttc atgacctggt tatagccttt gctggtgttt   4800
ttaaaatacc tggactcaat gacaaagacc gagtcttctt tttttttaaa caaaaacaaa   4860
```

```
aaaagcaacc agggctattt gtacagttga aggggtgaac agaatgggcg gctgtgctgg   4920

gagttggaag accgggcagc ccgctattta gagccatccc tcagtcagct ggcagggaca   4980

agccaacgcc aggtagcatg tggccaccct tgcccagtgt ctgtggcctg gcaagtggcc   5040

acgccctgtg tcagaccatc tgggaattaa gctccagaca gacttacaga tgccttcctt   5100

aggagttctt gcttcttgcg ttgatacttt gccccagaaa ggcctgggat tcattctggt   5160

tcttatcagg gtgtgtccac actctgctca caggtggatc cacggctttc cagtgcggag   5220

agtcgagatg ctccctgcag cccaggcccc gggcacctcc tgcaaccatc tctgggctca   5280

gcacctgagg cgggtttcct gggtcccctc tccagcaagc ctccaccagc aagctcggcc   5340

cagagcttcc cttccggctg gctctgaacc gtgcgtggtg cctacagcct gcagtctgga   5400

gacaagctct tccggagtgc tctgggagcc aggccagggt gtgagggagg tgcagaggca   5460

tccggggcgg gagcaagccc caggttgtga caggtgcagg tagacaacgc ccataaacag   5520

agatggtcct gaactctgga gagatccttc cctgatcctt tcggacgact acttggagcc   5580

ataagtaacc tcagcaaaaa cgaggcctct gcaagccact tttccatgcc aagcatccac   5640

ccggcccaca ggcatgtttc tgccgccact ccgcaagatg gacagggagc cagcaggcag   5700

gcgggaaggg ccaagtacag gcaatcaccc ccatcttctt ggtttgaagc tttatccatg   5760

tatcatgttc cgtgtagcca ttttattttt taagaaactg ctaatacttt ctccctaatg   5820

gaagccctga tcccccagag agctacaggt ctgctcccga cgggcctcgg gcctgacccg   5880

tccacacagg gccgtgtcaa cagcagcgac tcaagggacg tgtgtacata tgtaaatgag   5940

aaatagagac gtgtcaacag atgcattcat ttctcttgga atgtgtattg tttttatttt   6000

gcgaaacaaa acaaaacaaa aaaaaaagct tggaactcca tcacgtggaa aaactagatc   6060

ctgttggtta tagcatttgt gagttctcca cgtctgtctc tctcgctcat gtaatatact   6120

ctgaccctga gtggaaaggg gtttttgttc tgtttttatt ttacctacat gtactattta   6180

gcttcagtgt actagtcctg ccacctgtgt atttttaggg tgctatggaa ataatgaaaa   6240

gaaacgggga tttcagaaga aaattgtaac caaattcata ctttgtataa tttttgatat   6300

catgatcaca ggtgattcac acgtacacac ataaacacac ccaccagtgc agcctgaagt   6360

aactcccaca gaaaccatca tcgtctttgt acatcgtatg tacaatgcaa tcatttcata   6420

ctttaaactg gtcaaaaaac taattgtgat ttctagtctt gcaaagctgt atgtagttag   6480

atgatgtgac aacctctaat atttatctaa taaatatgta ttcagatgaa acctgtatat   6540

taggtgttca tgtggttatt ttgtatttaa agatcaaatt atttgactat tgctagacat   6600

ttctatactc tgttgtaaca ctgaggtatc tcatttgccc atgttaattt ttttctaaat   6660

aaattgacaa aaacaaaggt ttggcg                                         6686
```

```
<210> SEQ ID NO 6
<211> LENGTH: 968
<212> TYPE: PRT
<213> ORGANISM: Homo sapiens
<220> FEATURE:
<221> NAME/KEY: MISC_FEATURE
<222> LOCATION: (1)..(968)
<223> OTHER INFORMATION: ZMIZ1 968 amino acid protein

<400> SEQUENCE: 6

Met Arg Leu Leu Arg His Thr Glu Ser Glu Gln Trp Phe His Arg Phe
1               5                   10                  15

Pro Leu Cys Pro Ser Leu Thr Phe Trp Ala Pro Val Ala Met Trp Pro
            20                  25                  30
```

```
Gln Thr His Cys Val Gly Gly Arg Ser Ser Gly Leu Thr Lys Trp Thr
        35                  40                  45

Tyr Ser Phe Ser Ala Ser Leu Gln Asp Gly Ser Phe Pro Tyr Asp Ser
    50                  55                  60

Val Pro Trp Gln Gln Asn Thr Asn Gln Pro Pro Gly Ser Leu Ser Val
65                  70                  75                  80

Val Thr Thr Val Trp Gly Val Thr Asn Thr Ser Gln Ser Gln Ala Asp
                85                  90                  95

Val Leu Ile Pro His Ala Thr Cys Arg Pro Gly Pro Leu Leu Ile Ser
            100                 105                 110

Pro Trp Glu Pro Tyr Gly Gln Cys Gln Gln Pro His Glu Ser Arg Arg
        115                 120                 125

Gln Pro His Gly Val Gly His Asp His Gln Gln Pro Arg Pro Gln Leu
    130                 135                 140

Pro Thr Val Cys Gly Ala Ala Ala Ala Val Leu Ser Gln Gly Trp Pro
145                 150                 155                 160

Arg Ser Ala Leu His Pro Ala Glu His Val Trp Pro Ala Gln Leu Pro
                165                 170                 175

Arg Gln Arg Gly Leu Trp Gly Gln Pro Ala Ala Ala Ala Ala Ala Ala
            180                 185                 190

Ala Val Ala Ala Ala Ala Ala Thr Ala Thr Ala Thr Ala Thr Ala Thr
        195                 200                 205

Val Ala Ala Leu Gln Glu Thr Gln Asn Lys Asp Ile Asn Gln Tyr Gly
    210                 215                 220

Pro Ala Pro Val Leu Leu Pro Asp Leu Leu Lys Asp Gly Leu Gly Asp
225                 230                 235                 240

Glu Glu Arg Gly Ala Pro Ile Gly Met Gln Asn Arg Arg Asn Pro Ala
                245                 250                 255

Ser Met Ala Ala Gly Met Thr Pro Ser Gly Met Ser Gly Pro Pro Met
            260                 265                 270

Gly Met Asn Gln Pro Arg Pro Pro Gly Ile Ser Pro Phe Gly Thr His
        275                 280                 285

Gly Gln Arg Met Pro Gln Gln Thr Tyr Pro Gly Pro Arg Pro Gln Ser
    290                 295                 300

Leu Pro Ile Gln Asn Ile Lys Arg Pro Tyr Pro Gly Glu Pro Asn Tyr
305                 310                 315                 320

Gly Asn Gln Gln Tyr Gly Pro Asn Ser Gln Phe Pro Thr Gln Pro Gly
                325                 330                 335

Gln Tyr Pro Ala Pro Asn Pro Pro Arg Pro Leu Thr Ser Pro Asn Tyr
            340                 345                 350

Pro Gly Gln Arg Met Pro Ser Gln Pro Ser Ser Gly Gln Tyr Pro Pro
        355                 360                 365

Pro Thr Val Asn Met Gly Gln Tyr Tyr Lys Pro Glu Gln Phe Asn Gly
    370                 375                 380

Gln Asn Asn Thr Phe Ser Gly Ser Ser Tyr Ser Asn Tyr Ser Gln Gly
385                 390                 395                 400

Asn Val Asn Arg Pro Pro Arg Pro Val Pro Val Ala Asn Tyr Pro His
                405                 410                 415

Ser Pro Val Pro Gly Asn Pro Thr Pro Pro Met Thr Pro Gly Ser Ser
            420                 425                 430

Ile Pro Pro Tyr Leu Ser Pro Ser Gln Asp Val Lys Pro Pro Phe Pro
        435                 440                 445
```

```
Pro Asp Ile Lys Pro Asn Met Ser Ala Leu Pro Pro Pro Pro Asp His
    450                 455                 460

Asn Asp Glu Leu Arg Leu Thr Phe Pro Val Arg Asp Gly Val Val Leu
465                 470                 475                 480

Glu Pro Phe Arg Leu Glu His Asn Leu Ala Val Ser Asn His Val Phe
                485                 490                 495

His Leu Arg Pro Thr Val His Gln Thr Leu Met Trp Ser Asp Leu Glu
            500                 505                 510

Leu Gln Phe Lys Cys Tyr His His Glu Asp Arg Gln Met Asn Thr Asn
        515                 520                 525

Trp Pro Ala Ser Val Gln Val Ser Val Asn Ala Thr Pro Leu Thr Ile
    530                 535                 540

Glu Arg Gly Asp Asn Lys Thr Ser His Lys Pro Leu His Leu Lys His
545                 550                 555                 560

Val Cys Gln Pro Gly Arg Asn Thr Ile Gln Ile Thr Val Thr Ala Cys
                565                 570                 575

Cys Cys Ser His Leu Phe Val Leu Gln Leu Val His Arg Pro Ser Val
            580                 585                 590

Arg Ser Val Leu Gln Gly Leu Leu Lys Lys Arg Leu Leu Pro Ala Glu
        595                 600                 605

His Cys Ile Thr Lys Lys Arg Asn Phe Ser Ser Val Ala Ala Ser Ser
    610                 615                 620

Gly Asn Thr Thr Leu Asn Gly Glu Asp Gly Val Glu Gln Thr Ala Ile
625                 630                 635                 640

Lys Val Ser Leu Lys Cys Pro Ile Thr Phe Arg Arg Ile Gln Leu Pro
                645                 650                 655

Ala Arg Gly His Asp Cys Lys His Val Gln Cys Phe Asp Leu Glu Ser
            660                 665                 670

Tyr Leu Gln Leu Asn Cys Glu Arg Gly Thr Trp Arg Cys Pro Val Cys
        675                 680                 685

Lys Thr Ala Leu Leu Glu Gly Leu Glu Val Asp Gln Tyr Met Trp Gly
    690                 695                 700

Ile Leu Asn Ala Ile Gln His Glu Phe Glu Glu Val Thr Ile Asp Pro
705                 710                 715                 720

Thr Cys Ser Trp Arg Pro Val Pro Ile Lys Ser Asp Leu His Ile Lys
                725                 730                 735

Asp Asp Pro Asp Gly Ile Pro Ser Lys Arg Phe Lys Thr Met Ser Pro
            740                 745                 750

Ser Gln Met Ile Met Pro Asn Val Met Glu Met Ile Ala Ala Leu Gly
        755                 760                 765

Pro Gly Pro Ser Pro Tyr Pro Leu Pro Pro Pro Pro Gly Gly Thr Asn
    770                 775                 780

Ser Asn Asp Tyr Ser Ser Gln Asp Asn Tyr Gln Gly His Gly Asn Phe
785                 790                 795                 800

Asp Phe Pro His Gly Asn Pro Gly Gly Thr Ser Met Asn Asp Phe Met
                805                 810                 815

His Gly Pro Pro Gln Leu Ser His Pro Pro Asp Met Pro Asn Asn Met
            820                 825                 830

Ala Ala Leu Glu Lys Pro Leu Ser His Pro Met Gln Glu Thr Met Pro
        835                 840                 845

His Ala Gly Ser Ser Asp Gln Pro His Pro Ser Ile Gln Gln Gly Leu
    850                 855                 860

His Val Pro His Pro Ser Ser Gln Ser Gly Pro Pro Leu His His Ser
```

```
865                 870                 875                 880

Gly Ala Pro Pro Pro Pro Pro Ser Gln Pro Pro Arg Gln Pro Pro Gln
                885                 890                 895

Ala Ala Pro Ser Ser His Pro His Ser Asp Leu Thr Phe Asn Pro Ser
            900                 905                 910

Ser Ala Leu Glu Gly Gln Ala Gly Ala Gln Gly Ala Ser Asp Met Pro
        915                 920                 925

Glu Pro Ser Leu Asp Leu Leu Pro Glu Leu Thr Asn Pro Asp Glu Leu
    930                 935                 940

Leu Ser Tyr Leu Asp Pro Pro Asp Leu Pro Ser Asn Ser Asn Asp Asp
945                 950                 955                 960

Leu Leu Ser Leu Phe Glu Asn Asn
                965


<210> SEQ ID NO 7
<211> LENGTH: 7635
<212> TYPE: DNA
<213> ORGANISM: Homo sapiens
<220> FEATURE:
<221> NAME/KEY: misc_feature
<222> LOCATION: (1)..(7635)
<223> OTHER INFORMATION: ZMIZ1 X1 transcript

<400> SEQUENCE: 7

tcacttactc accccctaac gccgagttcc ttttcactgt ctgtggacat taaaaaagcg     60

agcggcggcg gcgggcgccg gggagagcgg gcggccgggc ggcaggcggg cgagcagcga    120

tcgggcggcc gagcgagcga gcaacgccgg cgcagcgcgg tgaccccagc cccagccggc    180

gcggagcagg agccggagcc gagcggatct cggcgccctc gctgcgctcc tcccggcccg    240

agcctgccct acccggcggt ggcggcggcg cgtcctccag cggcggcagc ggcgctcgca    300

gcgcccggac tcacggcagc tgtgttctga tttcgtacta ctgctggggc tgccacctcc    360

tcctccagac gctctcagca gacttgagtc ctggtccttc tgcagaggcc tgagcaggag    420

gaagaggagg aggcccgttg gcgtcggacc aatgctgcaa ggggtgtgag gagaggagcc    480

gctgtttttc actgagctgc cataccccga aagcaggatg gagctggagt gaggtggagg    540

ggccgcaagc tgctgaccgg cgtgtggaac actggtggtt tgcagatcac tgaggctgga    600

caacgttcat ggctctcggg tagaacctag tgaaacggcc agaatgaatt ctatggacag    660

gcacatccag cagaccaatg accgactgca gtgcatcaag cagcacttac agaatcctgc    720

caacttccac aatgccgcca cggagctgct ggactggtgc ggagacccac gggccttcca    780

gcggcccttc gagcagagcc tgatgggctg tttgacggtg gtcagtcggg tggcagccca    840

gcaaggcttt gacctggacc tcggctacag actgctggct gtgtgtgctg caaaccgaga    900

caagttcacc ccgaagtctg ccgccttgtt gtcctcctgg tgcgaagagc tcggccgcct    960

gctgctgctc cgacatcaga agagccgcca gagcgatccc cctgggaaac tccccatgca   1020

gccccctctc agctccatga gctccatgaa acccactctg tcgcacagtg atgggtcgtt   1080

cccctatgac tctgtccctt ggcagcagaa caccaaccag cctcccggct ccctttccgt   1140

ggtcaccacg gtttggggag taaccaacac atcccagagc caggtccttg ggaaccctat   1200

ggccaatgcc aacaacccca tgaatccagg cggcaacccc atggcgtcgg gcatgaccac   1260

cagcaaccca ggcctcaact ccccacagtt tgcggggcag cagcagcagt tctcagccaa   1320

ggctggcccc gctcagccct acatccagca gagcatgtat ggccggccca actaccccgg   1380

cagcgggggc tttggggcca gttaccctgg gggtcctaac gcccccgcag gcatgggcat   1440
```

```
ccctccgcac accaggccgc ctgctgactt cactcagccc gcggcagccg ctgcagcagc   1500

ggcagtggca gcagcagcag ccacagctac agccacagcc acggccactg tggcagccct   1560

gcaggagaca cagaacaagg atataaacca gtatggaccg gtctgttcct ctttccagat   1620

gggtcccacc caggcgtata acagccaatt catgaaccag cccgggccgc gggggcctgc   1680

ctccatgggg ggcagcatga accccgcgag catggcggct ggcatgacgc cctcggggat   1740

gagcggccct cccatgggca tgaaccagcc ccggccgccc ggcatcagcc cctttggcac   1800

acacgggcag cggatgcccc agcagaccta cccgggcccc cggcccagt  cccttcctat   1860

tcagaacata aagaggccat accctggaga gcccaactat ggaaaccagc aatatggacc   1920

aaacagccag ttccccaccc agccaggcca gtacccagcc cccaaccccc cgaggccact   1980

cacctccccc aactacccag gacagaggat gcccagccag ccgagctccg ggcagtaccc   2040

gccccccacg gtcaacatgg ggcagtatta caagccagaa cagtttaatg gacaaaataa   2100

cacgttctcg ggaagcagct acagtaacta cagccaaggg aatgtcaaca ggcctcccag   2160

gccggttcct gtggcaaatt acccccactc acctgttcca gggaacccca caccccccat   2220

gacccctggg agcagcatcc ctccatacct gtcccccagc caagacgtca aaccaccctt   2280

cccgcctgac atcaagccaa atatgagcgc tctgccacca cccccagcca accacaatga   2340

cgagctgcgg ctcacattcc ctgtgcggga tggcgtggtg ctggagccct tccgcctgga   2400

gcacaacctg gcggtcagca accatgtgtt ccacctgcgg cccacggtcc accagacgct   2460

gatgtggagg tctgacctgg agctgcagtt caagtgctac caccacgagg accggcagat   2520

gaacaccaac tggcccgcct cggtgcaggt cagcgtgaac gccacgcccc tcaccattga   2580

gcgcggcgac aacaagacct cccacaagcc cctgcacctg aagcacgtgt gccagccggg   2640

ccgcaacacc atccagatca ccgtcacggc ctgctgctgc tcccacctct tcgtgctgca   2700

gctggtacac cggccctccg tccgctctgt gctgcaagga ctcctcaaga agcgcctcct   2760

gcccgcagag cactgtatca cgaaaatcaa gcggaatttc agcagcgtgg ctgcctcctc   2820

gggcaacacg accctcaacg gggaggatgg ggtggagcag acggccatca aggtgtctct   2880

gaagtgcccc atcacattcc ggcgcatcca gctgcctgct cgaggacacg attgcaagca   2940

tgtgcagtgc tttgatctgg agtcatacct gcagctgaat tgcgagagag ggacctggag   3000

gtgtcctgtg tgcaataaaa ccgctctgct ggagggcctg gaggtggatc agtacatgtg   3060

gggaatcctg aatgccatcc aacactccga gtttgaagag gtcaccatcg atcccacgtg   3120

cagctggcgg ccggtgccca tcaagtcgga cttacacatc aaggacgacc ctgatggcat   3180

cccctccaag cggttcaaga ccatgagtcc cagccagatg atcatgccca atgtcatgga   3240

gatgatcgca gccctgggcc ccggcccgtc cccctatccc ctcccgcctc ccccaggggg   3300

caccaactcc aacgactaca gcagccaagg caacaactac caaggccatg gcaactttga   3360

cttcccccac gggaaccctg gagggacatc catgaatgac ttcatgcacg ggccccccca   3420

gctctcccac cccccggaca tgcccaacaa catggccgcc ctcgagaaac ccctcagcca   3480

ccccatgcag gaaactatgc cacacgctgg cagctctgac cagccccacc cctccataca   3540

acaaggtttg cacgtaccac accccagcag ccagtcaggg cctccattac atcacagtgg   3600

ggctcctcct cctcctcctt cccagcctcc ccggcagccg ccacaggccg ctcccagcag   3660

ccatccacac agcgacctga cctttaaccc ctcctcagcc ttagagggtc aggccggagc   3720

gcagggagcg tccgacatgc cggagccttc gctggatctc cttcccgaac tcacaaatcc   3780
```

-continued

```
tgacgagctc ctgtcttatc tggacccccc cgacctgccg agcaatagta acgatgacct   3840
cctgtctcta tttgagaaca actgagggcc acccggtcgg ggccatccct ccacactctg   3900
catcctaccc cacctaccca acacactttt ccacctggga gcctgtgccc tcagaccgcc   3960
ccgcaccaga gccacgggct gtggggcggg gagccctccc ccgctgcagc cctctcagaa   4020
cagaggggta gggagggtgc accagtgcac caggaaggct gtgtgggtct ggagcccacg   4080
tcccacctcc acacccttgg cttgggccca tgcccagcgc aggcctgaag accaccctcc   4140
cgagaggaac cagcccggta agagggcaca cgctgatgcg gcttcccggt ccctccgcgt   4200
gtgccgattc cagatgacct tccagtgtcc ccaaggttct tccatcttct agactgtaac   4260
cctgcctccc tgcttcctgg tccagagcct ccctccagtg actgtggagc ctgagaaggc   4320
ccccgggccc cagcatgggc cccgagcctt ggaggagcac tggcagttgg tggcagtgag   4380
accagcccac ccaccaccac ccaccacaga aaagcacaaa cctctgggaa agacaacgtc   4440
tctcgggggc caggggtcat cggtttgacc cctgacctat aagccaagat accccataaa   4500
cacactcaga aagcagagaa aaaggacaag agtctgtgtt tgagaggggg tctgccattc   4560
ctgcttgggg actggtgggg aagagggcca ggacatcttc tgagccagga cgtccctgag   4620
gctccacctc caagctcaga cagggcccag gcttggggaa cagagagagc aggtgtacac   4680
ccaaccaaag tgattgtgcc cttggttggg gggcgcgggc atataacctg tcagaagcaa   4740
acaggagcgg caacttctaa ctttgctcca agccactctc tttttaaaca gcaacaattt   4800
aaagctatga agtcacctgg agaaaaggaa cgttgctctt ggacagcaag caaaccattt   4860
ctctccgtct gttctgtttt tctcctagtc cctctcctgc cacctctcca agacttccgt   4920
gggacaccca cttccctctg tcctagttct ctttgtccaa tcagatggca agggcagtgc   4980
gtggaaaggc cggggaggtg cagaaaccag agcccagggc aatggtgtct gtccagcccc   5040
tccctctgtc cctgtgctcc aagctgcccc cggctgcagc ccaggccatg gacatgtgca   5100
ccagtatgta cctgcaggca tggggggggag gggggcgtgt ttctgggcct gccccagaca   5160
ctgcccttgg ctgccagcct accctgcctg cactcctcca ccatcacaat ctcacccaaa   5220
ctcctgctca ctcaagcaaa agcagcctct ggccttccct ccaccgcttt gctccatctg   5280
gcttaccact ctccagggcc tcctggggag cctgtcctgt gttcactttg tttcaggctg   5340
gtctgtgccc cgtgagccac atggcctagg gtgatgccag gttgtcccgt cactggggtc   5400
ccatctgtaa attctttgcg cccttcccgg ctgctgcctg gggccctttc ctgctctccc   5460
gtccgctgtg ggtggtcccc agctctcctc tgtgggtttt accggaaagg tggccccagc   5520
tgttgacttc cagtcactgt cccagacggc acaaggtttt ctgtaggaaa gctgccattg   5580
ccccggcccc ttttcttcct ttgtcccgtt gtcgaggttt tttcaaatag cgtgttgttc   5640
agtatgcaaa tcaattattt taagaatcgc ttttgtaaat atctttgtga atattttagt   5700
atcgtctttg ataatattca acattttcat gacctggtta tagcctttgc tggtgttttt   5760
aaaatacctg gactcaatga caaagaccga gtcttctttt tttttaaaca aaaacaaaaa   5820
aagcaaccag ggctatttgt acagttgaag ggtgaacag aatgggcggc tgtgctggga   5880
gttggaagac cgggcagccc gctatttaga gccatccctc agtcagctgg cagggacaag   5940
ccaacgccag gtagcatgtg gccacccttg cccagtgtct gtggcctggc aagtggccac   6000
gccctgtgtc agaccatctg ggaattaagc tccagacaga cttacagatg ccttccttag   6060
gagttcttgc ttcttgcgtt gatactttgc cccagaaagg cctgggattc attctggttc   6120
ttatcagggt gtgtccacac tctgctcaca ggtggatcca cggctttcca gtgcggagag   6180
```

```
tcgagatgct ccctgcagcc caggccccgg gcacctcctg caaccatctc tgggctcagc   6240

acctgaggcg ggtttcctgg gtcccctctc cagcaagcct ccaccagcaa gctcggccca   6300

gagcttccct tccggctggc tctgaaccgt gcgtggtgcc tacagcctgc agtctggaga   6360

caagctcttc cggagtgctc tgggagccag gccagggtgt gagggaggtg cagaggcatc   6420

cggggcggga gcaagcccca ggttgtgaca ggtgcaggta gacaacgccc ataaacagag   6480

atggtcctga actctggaga gatccttccc tgatcctttc ggacgactac ttggagccat   6540

aagtaacctc agcaaaaacg aggcctctgc aagccacttt tccatgccaa gcatccaccc   6600

ggcccacagg catgtttctg ccgccactcc gcaagatgga cagggagcca gcaggcaggc   6660

gggaagggcc aagtacaggc aatcaccccc atcttcttgg tttgaagctt tatccatgta   6720

tcatgttccg tgtagccatt ttattttta agaaactgct aatactttct ccctaatgga   6780

agccctgatc cccagagag ctacaggtct gctcccgacg ggcctcgggc ctgacccgtc    6840

cacacagggc cgtgtcaaca gcagcgactc aagggacgtg tgtacatatg taaatgagaa   6900

atagagacgt gtcaacagat gcattcattt ctcttggaat gtgtattgtt tttattttgc   6960

gaaacaaaac aaaacaaaaa aaaaagcttg gaactccatc acgtggaaaa actagatcct   7020

gttggttata gcatttgtga gttctccacg tctgtctctc tcgctcatgt aatatactct   7080

gaccctgagt ggaaaggggt ttttgttctg tttttatttt acctacatgt actatttagc   7140

ttcagtgtac tagtcctgcc acctgtgtat ttttagggtg ctatggaaat aatgaaaaga   7200

aacggggatt tcagaagaaa attgtaacca aattcatact ttgtataatt tttgatatca   7260

tgatcacagg tgattcacac gtacacacat aaacacaccc accagtgcag cctgaagtaa   7320

ctcccacaga aaccatcatc gtctttgtac atcgtatgta caatgcaatc atttcatact   7380

ttaaactggt caaaaaacta attgtgattt ctagtcttgc aaagctgtat gtagttagat   7440

gatgtgacaa cctctaatat ttatctaata aatatgtatt cagatgaaac ctgtatatta   7500

ggtgttcatg tggttatttt gtatttaaag atcaaattat ttgactattg ctagacattt   7560

ctatactctg ttgtaacact gaggtatctc atttgcccat gttaattttt ttctaaataa   7620

attgacaaaa acaaa                                                    7635
```

<210> SEQ ID NO 8
<211> LENGTH: 1073
<212> TYPE: PRT
<213> ORGANISM: Homo sapiens
<220> FEATURE:
<221> NAME/KEY: MISC_FEATURE
<222> LOCATION: (1)..(1073)
<223> OTHER INFORMATION: ZMIZ1 X1 amino acid sequence

<400> SEQUENCE: 8

```
Met Asn Ser Met Asp Arg His Ile Gln Gln Thr Asn Asp Arg Leu Gln
1               5                   10                  15

Cys Ile Lys Gln His Leu Gln Asn Pro Ala Asn Phe His Asn Ala Ala
            20                  25                  30

Thr Glu Leu Leu Asp Trp Cys Gly Asp Pro Arg Ala Phe Gln Arg Pro
        35                  40                  45

Phe Glu Gln Ser Leu Met Gly Cys Leu Thr Val Val Ser Arg Val Ala
    50                  55                  60

Ala Gln Gln Gly Phe Asp Leu Asp Leu Gly Tyr Arg Leu Leu Ala Val
65                  70                  75                  80

Cys Ala Ala Asn Arg Asp Lys Phe Thr Pro Lys Ser Ala Ala Leu Leu
```

```
                85                  90                  95

Ser Ser Trp Cys Glu Glu Leu Gly Arg Leu Leu Leu Leu Arg His Gln
            100                 105                 110

Lys Ser Arg Gln Ser Asp Pro Pro Gly Lys Leu Pro Met Gln Pro Pro
        115                 120                 125

Leu Ser Ser Met Ser Ser Met Lys Pro Thr Leu Ser His Ser Asp Gly
    130                 135                 140

Ser Phe Pro Tyr Asp Ser Val Pro Trp Gln Gln Asn Thr Asn Gln Pro
145                 150                 155                 160

Pro Gly Ser Leu Ser Val Val Thr Thr Val Trp Gly Val Thr Asn Thr
                165                 170                 175

Ser Gln Ser Gln Val Leu Gly Asn Pro Met Ala Asn Ala Asn Asn Pro
            180                 185                 190

Met Asn Pro Gly Gly Asn Pro Met Ala Ser Gly Met Thr Thr Ser Asn
        195                 200                 205

Pro Gly Leu Asn Ser Pro Gln Phe Ala Gly Gln Gln Gln Gln Phe Ser
    210                 215                 220

Ala Lys Ala Gly Pro Ala Gln Pro Tyr Ile Gln Gln Ser Met Tyr Gly
225                 230                 235                 240

Arg Pro Asn Tyr Pro Gly Ser Gly Gly Phe Gly Ala Ser Tyr Pro Gly
                245                 250                 255

Gly Pro Asn Ala Pro Ala Gly Met Gly Ile Pro Pro His Thr Arg Pro
            260                 265                 270

Pro Ala Asp Phe Thr Gln Pro Ala Ala Ala Ala Ala Ala Ala Ala Val
        275                 280                 285

Ala Ala Ala Ala Ala Thr Ala Thr Ala Thr Ala Thr Ala Thr Val Ala
    290                 295                 300

Ala Leu Gln Glu Thr Gln Asn Lys Asp Ile Asn Gln Tyr Gly Pro Val
305                 310                 315                 320

Cys Ser Ser Phe Gln Met Gly Pro Thr Gln Ala Tyr Asn Ser Gln Phe
                325                 330                 335

Met Asn Gln Pro Gly Pro Arg Gly Pro Ala Ser Met Gly Gly Ser Met
            340                 345                 350

Asn Pro Ala Ser Met Ala Ala Gly Met Thr Pro Ser Gly Met Ser Gly
        355                 360                 365

Pro Pro Met Gly Met Asn Gln Pro Arg Pro Pro Gly Ile Ser Pro Phe
    370                 375                 380

Gly Thr His Gly Gln Arg Met Pro Gln Gln Thr Tyr Pro Gly Pro Arg
385                 390                 395                 400

Pro Gln Ser Leu Pro Ile Gln Asn Ile Lys Arg Pro Tyr Pro Gly Glu
                405                 410                 415

Pro Asn Tyr Gly Asn Gln Gln Tyr Gly Pro Asn Ser Gln Phe Pro Thr
            420                 425                 430

Gln Pro Gly Gln Tyr Pro Ala Pro Asn Pro Pro Arg Pro Leu Thr Ser
        435                 440                 445

Pro Asn Tyr Pro Gly Gln Arg Met Pro Ser Gln Pro Ser Ser Gly Gln
    450                 455                 460

Tyr Pro Pro Pro Thr Val Asn Met Gly Gln Tyr Tyr Lys Pro Glu Gln
465                 470                 475                 480

Phe Asn Gly Gln Asn Asn Thr Phe Ser Gly Ser Ser Tyr Ser Asn Tyr
                485                 490                 495

Ser Gln Gly Asn Val Asn Arg Pro Pro Arg Pro Val Pro Val Ala Asn
            500                 505                 510
```

```
Tyr Pro His Ser Pro Val Pro Gly Asn Pro Thr Pro Pro Met Thr Pro
        515                 520                 525

Gly Ser Ser Ile Pro Pro Tyr Leu Ser Pro Ser Gln Asp Val Lys Pro
    530                 535                 540

Pro Phe Pro Pro Asp Ile Lys Pro Asn Met Ser Ala Leu Pro Pro Pro
545                 550                 555                 560

Pro Ala Asn His Asn Asp Glu Leu Arg Leu Thr Phe Pro Val Arg Asp
                565                 570                 575

Gly Val Val Leu Glu Pro Phe Arg Leu Glu His Asn Leu Ala Val Ser
            580                 585                 590

Asn His Val Phe His Leu Arg Pro Thr Val His Gln Thr Leu Met Trp
        595                 600                 605

Arg Ser Asp Leu Glu Leu Gln Phe Lys Cys Tyr His His Glu Asp Arg
    610                 615                 620

Gln Met Asn Thr Asn Trp Pro Ala Ser Val Gln Val Ser Val Asn Ala
625                 630                 635                 640

Thr Pro Leu Thr Ile Glu Arg Gly Asp Asn Lys Thr Ser His Lys Pro
                645                 650                 655

Leu His Leu Lys His Val Cys Gln Pro Gly Arg Asn Thr Ile Gln Ile
            660                 665                 670

Thr Val Thr Ala Cys Cys Cys Ser His Leu Phe Val Leu Gln Leu Val
        675                 680                 685

His Arg Pro Ser Val Arg Ser Val Leu Gln Gly Leu Leu Lys Lys Arg
    690                 695                 700

Leu Leu Pro Ala Glu His Cys Ile Thr Lys Ile Lys Arg Asn Phe Ser
705                 710                 715                 720

Ser Val Ala Ala Ser Ser Gly Asn Thr Thr Leu Asn Gly Glu Asp Gly
                725                 730                 735

Val Glu Gln Thr Ala Ile Lys Val Ser Leu Lys Cys Pro Ile Thr Phe
            740                 745                 750

Arg Arg Ile Gln Leu Pro Ala Arg Gly His Asp Cys Lys His Val Gln
        755                 760                 765

Cys Phe Asp Leu Glu Ser Tyr Leu Gln Leu Asn Cys Glu Arg Gly Thr
    770                 775                 780

Trp Arg Cys Pro Val Cys Asn Lys Thr Ala Leu Leu Glu Gly Leu Glu
785                 790                 795                 800

Val Asp Gln Tyr Met Trp Gly Ile Leu Asn Ala Ile Gln His Ser Glu
                805                 810                 815

Phe Glu Glu Val Thr Ile Asp Pro Thr Cys Ser Trp Arg Pro Val Pro
            820                 825                 830

Ile Lys Ser Asp Leu His Ile Lys Asp Asp Pro Asp Gly Ile Pro Ser
        835                 840                 845

Lys Arg Phe Lys Thr Met Ser Pro Ser Gln Met Ile Met Pro Asn Val
    850                 855                 860

Met Glu Met Ile Ala Ala Leu Gly Pro Gly Pro Ser Pro Tyr Pro Leu
865                 870                 875                 880

Pro Pro Pro Pro Gly Gly Thr Asn Ser Asn Asp Tyr Ser Ser Gln Gly
                885                 890                 895

Asn Asn Tyr Gln Gly His Gly Asn Phe Asp Phe Pro His Gly Asn Pro
            900                 905                 910

Gly Gly Thr Ser Met Asn Asp Phe Met His Gly Pro Pro Gln Leu Ser
        915                 920                 925
```

```
His Pro Pro Asp Met Pro Asn Asn Met Ala Ala Leu Glu Lys Pro Leu
    930                 935                 940

Ser His Pro Met Gln Glu Thr Met Pro His Ala Gly Ser Ser Asp Gln
945                 950                 955                 960

Pro His Pro Ser Ile Gln Gln Gly Leu His Val Pro His Pro Ser Ser
                965                 970                 975

Gln Ser Gly Pro Pro Leu His His Ser Gly Ala Pro Pro Pro Pro Pro
            980                 985                 990

Ser Gln Pro Pro Arg Gln Pro Pro  Gln Ala Ala Pro Ser  Ser His Pro
        995                 1000                1005

His Ser  Asp Leu Thr Phe Asn  Pro Ser Ser Ala Leu  Glu Gly Gln
    1010                 1015                 1020

Ala Gly  Ala Gln Gly Ala Ser  Asp Met Pro Glu Pro  Ser Leu Asp
    1025                 1030                 1035

Leu Leu  Pro Glu Leu Thr Asn  Pro Asp Glu Leu Leu  Ser Tyr Leu
    1040                 1045                 1050

Asp Pro  Pro Asp Leu Pro Ser  Asn Ser Asn Asp Asp  Leu Leu Ser
    1055                 1060                 1065

Leu Phe  Glu Asn Asn
    1070


<210> SEQ ID NO 9
<211> LENGTH: 7634
<212> TYPE: DNA
<213> ORGANISM: Homo sapiens
<220> FEATURE:
<221> NAME/KEY: misc_feature
<222> LOCATION: (1)..(7634)
<223> OTHER INFORMATION: ZMIZ1 X2 transcript

<400> SEQUENCE: 9

cccaccgaag aagagttcaa gcttttcttc cagggaactg agagggccat gctgaaactg      60

gaagcctcag cctgcaagag gtgccctggg gaaggaggta gttggtactg atgttggccg     120

actacaaagg agctggctcc tgggactctg aatgctgtgc cctctgcagc cacccagccc     180

cacaatggga agccagtggt tacatttacc cctgtctctt ctgaaccata tggtggctgc     240

accacagctg gctcagaggc tctgaaagaa ggcccacagg ggaacatgat gtcttgcctg     300

agccaggact cacggcagct gtgttctgat ttcgtactac tgctggggct gccacctcct     360

cctccagacg ctctcagcag acttgagtcc tggtccttct gcagaggcct gagcaggagg     420

aagaggagga ggcccgttgg cgtcggacca atgctgcaag ggtgtgaggg agaggagccg     480

ctgtttttca ctgagctgcc ataccccgaa agcaggatgg agctggagtg aggtggaggg     540

gccgcaagct gctgaccggc gtgtggaaca ctggtggttt gcagatcact gaggctggac     600

aacgttcatg gctctcgggt agaacctagt gaaacggcca gaatgaattc tatggacagg     660

cacatccagc agaccaatga ccgactgcag tgcatcaagc agcacttaca gaatcctgcc     720

aacttccaca atgccgccac ggagctgctg gactggtgcg gagacccacg ggccttccag     780

cggcccttcg agcagagcct gatgggctgt ttgacggtgg tcagtcgggt ggcagcccag     840

caaggctttg acctggacct cggctacaga ctgctggctg tgtgtgctgc aaaccgagac     900

aagttcaccc cgaagtctgc cgccttgttg tcctcctggt gcgaagagct cggccgcctg     960

ctgctgctcc gacatcagaa gagccgccag agcgatcccc ctgggaaact ccccatgcag    1020

ccccctctca gctccatgag ctccatgaaa cccactctgt cgcacagtga tgggtcgttc    1080

ccctatgact ctgtcccttg gcagcagaac accaaccagc ctcccggctc cctttccgtg    1140
```

```
gtcaccacgg tttggggagt aaccaacaca tcccagagcc aggtccttgg gaaccctatg   1200
gccaatgcca acaaccccat gaatccaggc ggcaacccca tggcgtcggg catgaccacc   1260
agcaacccag gcctcaactc cccacagttt gcggggcagc agcagcagtt ctcagccaag   1320
gctggccccg ctcagcccta catccagcag agcatgtatg gccggcccaa ctaccccggc   1380
agcgggggct ttggggccag ttaccctggg ggtcctaacg cccccgcagg catgggcatc   1440
cctccgcaca ccaggccgcc tgctgacttc actcagcccg cggcagccgc tgcagcagcg   1500
gcagtggcag cagcagcagc cacagctaca gccacagcca cggccactgt ggcagccctg   1560
caggagacac agaacaagga tataaaccag tatggaccgg tctgttcctc tttccagatg   1620
ggtcccaccc aggcgtataa cagccaattc atgaaccagc ccgggccgcg gggggcctgcc   1680
tccatggggg gcagcatgaa ccccgcgagc atggcggctg gcatgacgcc ctcggggatg   1740
agcggccctc ccatgggcat gaaccagccc cggccgcccg gcatcagccc ctttggcaca   1800
cacgggcagc ggatgcccca gcagacctac ccgggccccc ggccccagtc ccttcctatt   1860
cagaacataa agaggccata ccctggagag cccaactatg gaaaccagca atatggacca   1920
aacagccagt tccccaccca gccaggccag tacccagccc ccaaccccc gaggccactc   1980
acctcccccca actacccagg acagaggatg cccagccagc cgagctccgg gcagtacccg   2040
cccccacgg tcaacatggg gcagtattac aagccagaac agtttaatgg acaaaataac   2100
acgttctcgg gaagcagcta cagtaactac agccaaggga atgtcaacag gcctcccagg   2160
ccggttcctg tggcaaatta cccccactca cctgttccag ggaaccccac accccccatg   2220
acccctggga gcagcatccc tccatacctg tcccccagcc aagacgtcaa accacccttc   2280
ccgcctgaca tcaagccaaa tatgagcgct ctgccaccac ccccagccaa ccacaatgac   2340
gagctgcggc tcacattccc tgtgcgggat ggcgtggtgc tggagccctt ccgcctggag   2400
cacaacctgg cggtcagcaa ccatgtgttc cacctgcggc ccacggtcca ccagacgctg   2460
atgtggaggt ctgacctgga gctgcagttc aagtgctacc accacgagga ccggcagatg   2520
aacaccaact ggcccgcctc ggtgcaggtc agcgtgaacg ccacgcccct caccattgag   2580
cgcggcgaca acaagacctc ccacaagccc ctgcacctga agcacgtgtg ccagccgggc   2640
cgcaacacca tccagatcac cgtcacggcc tgctgctgct cccacctctt cgtgctgcag   2700
ctggtacacc ggccctccgt ccgctctgtg ctgcaaggac tcctcaagaa gcgcctcctg   2760
cccgcagagc actgtatcac gaaaatcaag cggaatttca gcagcgtggc tgcctcctcg   2820
ggcaacacga ccctcaacgg ggaggatggg gtggagcaga cggccatcaa ggtgtctctg   2880
aagtgcccca tcacattccg gcgcatccag ctgcctgctc gaggacacga ttgcaagcat   2940
gtgcagtgct ttgatctgga gtcatacctg cagctgaatt gcgagagagg gacctggagg   3000
tgtcctgtgt gcaataaaac cgctctgctg gagggcctgg aggtggatca gtacatgtgg   3060
ggaatcctga atgccatcca acactccgag tttgaagagg tcaccatcga tcccacgtgc   3120
agctggcggc cggtgcccat caagtcggac ttacacatca aggacgaccc tgatggcatc   3180
cctccaagc ggttcaagac catgagtccc agccagatga tcatgcccaa tgtcatggag   3240
atgatcgcag ccctgggccc cggcccgtcc ccctatcccc tcccgcctcc cccagggggc   3300
accaactcca acgactacag cagccaaggc aacaactacc aaggccatgg caactttgac   3360
ttcccccacg ggaaccctgg agggacatcc atgaatgact tcatgcacgg gcccccccag   3420
ctctcccacc ccccggacat gcccaacaac atggccgccc tcgagaaacc cctcagccac   3480
```

-continued

```
cccatgcagg aaactatgcc acacgctggc agctctgacc agccccaccc ctccatacaa   3540

caaggtttgc acgtaccaca ccccagcagc cagtcagggc ctccattaca tcacagtggg   3600

gctcctcctc ctcctccttc ccagcctccc cggcagccgc cacaggccgc tcccagcagc   3660

catccacaca gcgacctgac ctttaacccc tcctcagcct tagagggtca ggccggagcg   3720

cagggagcgt ccgacatgcc ggagccttcg ctggatctcc ttcccgaact cacaaatcct   3780

gacgagctcc tgtcttatct ggaccccccc gacctgccga gcaatagtaa cgatgacctc   3840

ctgtctctat ttgagaacaa ctgagggcca cccggtcggg gccatccctc cacactctgc   3900

atcctacccc acctacccaa cacacttttc cacctgggag cctgtgccct cagaccgccc   3960

cgcaccagag ccacgggctg tggggcgggg agccctcccc cgctgcagcc ctctcagaac   4020

agaggggtag ggagggtgca ccagtgcacc aggaaggctg tgtgggtctg gagcccacgt   4080

cccacctcca cacccttggc ttgggcccat gcccagcgca ggcctgaaga ccaccctccc   4140

gagaggaacc agcccggtaa gagggcacac gctgatgcgg cttcccggtc cctccgcgtg   4200

tgccgattcc agatgacctt ccagtgtccc caaggttctt ccatcttcta gactgtaacc   4260

ctgcctccct gcttcctggt ccagagcctc cctccagtga ctgtggagcc tgagaaggcc   4320

cccgggcccc agcatgggcc ccgagccttg gaggagcact ggcagttggt ggcagtgaga   4380

ccagcccacc caccaccacc caccacagaa aagcacaaac ctctgggaaa gacaacgtct   4440

ctcgggggcc aggggtcatc ggtttgaccc ctgacctata agccaagata ccccataaac   4500

acactcagaa agcagagaaa aaggacaaga gtctgtgttt gagagggggt ctgccattcc   4560

tgcttgggga ctggtgggga agagggccag gacatcttct gagccaggac gtccctgagg   4620

ctccacctcc aagctcagac agggcccagg cttggggaac agagagagca ggtgtacacc   4680

caaccaaagt gattgtgccc ttggttgggg ggcgcgggca tataacctgt cagaagcaaa   4740

caggagcggc aacttctaac tttgctccaa gccactctct ttttaaacag caacaattta   4800

aagctatgaa gtcacctgga gaaaaggaac gttgctcttg gacagcaagc aaaccatttc   4860

tctccgtctg ttctgttttt ctcctagtcc ctctcctgcc acctctccaa gacttccgtg   4920

ggacacccac ttccctctgt cctagttctc tttgtccaat cagatggcaa gggcagtgcg   4980

tggaaaggcc ggggaggtgc agaaaccaga gcccagggca atggtgtctg tccagcccct   5040

ccctctgtcc ctgtgctcca agctgccccc ggctgcagcc caggccatgg acatgtgcac   5100

cagtatgtac ctgcaggcat gggggggagg ggggcgtgtt tctgggcctg ccccagacac   5160

tgcccttggc tgccagccta ccctgcctgc actcctccac catcacaatc tcacccaaac   5220

tcctgctcac tcaagcaaaa gcagcctctg gccttccctc caccgctttg ctccatctgg   5280

cttaccactc tccagggcct cctggggagc ctgtcctgtg ttcactttgt ttcaggctgg   5340

tctgtgcccc gtgagccaca tggcctaggg tgatgccagg ttgtcccgtc actggggtcc   5400

catctgtaaa ttctttgcgc ccttcccggc tgctgcctgg ggccctttcc tgctctcccg   5460

tccgctgtgg gtggtcccca gctctcctct gtgggtttta ccggaaaggt ggccccagct   5520

gttgacttcc agtcactgtc ccagacggca caaggttttc tgtaggaaag ctgccattgc   5580

cccggcccct tttcttcctt tgtcccgttg tcgaggtttt ttcaaatagc gtgttgttca   5640

gtatgcaaat caattatttt aagaatcgct tttgtaaata tctttgtgaa tattttagta   5700

tcgtctttga taatattcaa cattttcatg acctggttat agcctttgct ggtgttttta   5760

aaatacctgg actcaatgac aaagaccgag tcttcttttt ttttaaacaa aaacaaaaaa   5820

agcaaccagg gctatttgta cagttgaagg ggtgaacaga atgggcggct gtgctgggag   5880
```

```
ttggaagacc gggcagcccg ctatttagag ccatccctca gtcagctggc agggacaagc   5940

caacgccagg tagcatgtgg ccacccttgc ccagtgtctg tggcctggca agtggccacg   6000

ccctgtgtca gaccatctgg gaattaagct ccagacagac ttacagatgc cttccttagg   6060

agttcttgct tcttgcgttg atactttgcc ccagaaaggc ctgggattca ttctggttct   6120

tatcagggtg tgtccacact ctgctcacag gtggatccac ggctttccag tgcggagagt   6180

cgagatgctc cctgcagccc aggccccggg cacctcctgc aaccatctct gggctcagca   6240

cctgaggcgg gtttcctggg tcccctctcc agcaagcctc caccagcaag ctcggcccag   6300

agcttccctt ccggctggct ctgaaccgtg cgtggtgcct acagcctgca gtctggagac   6360

aagctcttcc ggagtgctct gggagccagg ccagggtgtg agggaggtgc agaggcatcc   6420

ggggcgggag caagccccag gttgtgacag gtgcaggtag acaacgccca taaacagaga   6480

tggtcctgaa ctctggagag atccttccct gatcctttcg gacgactact tggagccata   6540

agtaacctca gcaaaaacga ggcctctgca agccactttt ccatgccaag catccacccg   6600

gcccacaggc atgtttctgc cgccactccg caagatggac agggagccag caggcaggcg   6660

ggaagggcca agtacaggca atcaccccca tcttcttggt ttgaagcttt atccatgtat   6720

catgttccgt gtagccattt tattttttaa gaaactgcta atactttctc cctaatggaa   6780

gccctgatcc cccagagagc tacaggtctg ctcccgacgg gcctcgggcc tgacccgtcc   6840

acacagggcc gtgtcaacag cagcgactca agggacgtgt gtacatatgt aaatgagaaa   6900

tagagacgtg tcaacagatg cattcatttc tcttggaatg tgtattgttt ttattttgcg   6960

aaacaaaaca aaacaaaaaa aaaagcttgg aactccatca cgtggaaaaa ctagatcctg   7020

ttggttatag catttgtgag ttctccacgt ctgtctctct cgctcatgta atatactctg   7080

accctgagtg gaaaggggtt tttgttctgt ttttatttta cctacatgta ctatttagct   7140

tcagtgtact agtcctgcca cctgtgtatt tttagggtgc tatggaaata atgaaaagaa   7200

acggggattt cagaagaaaa ttgtaaccaa attcatactt tgtataattt ttgatatcat   7260

gatcacaggt gattcacacg tacacacata aacacaccca ccagtgcagc ctgaagtaac   7320

tcccacagaa accatcatcg tctttgtaca tcgtatgtac aatgcaatca tttcatactt   7380

taaactggtc aaaaaactaa ttgtgatttc tagtcttgca aagctgtatg tagttagatg   7440

atgtgacaac ctctaatatt tatctaataa atatgtattc agatgaaacc tgtatattag   7500

gtgttcatgt ggttattttg tatttaaaga tcaaattatt tgactattgc tagacatttc   7560

tatactctgt tgtaacactg aggtatctca tttgcccatg ttaatttttt tctaaataaa   7620

ttgacaaaaa caaa                                                     7634
```

<210> SEQ ID NO 10
<211> LENGTH: 1073
<212> TYPE: PRT
<213> ORGANISM: Homo sapiens
<220> FEATURE:
<221> NAME/KEY: MISC_FEATURE
<222> LOCATION: (1)..(1073)
<223> OTHER INFORMATION: ZMIZ1 X2 amino acid sequence

<400> SEQUENCE: 10

```
Met Asn Ser Met Asp Arg His Ile Gln Gln Thr Asn Asp Arg Leu Gln
1               5                   10                  15

Cys Ile Lys Gln His Leu Gln Asn Pro Ala Asn Phe His Asn Ala Ala
            20                  25                  30
```

```
Thr Glu Leu Leu Asp Trp Cys Gly Asp Pro Arg Ala Phe Gln Arg Pro
        35                  40                  45

Phe Glu Gln Ser Leu Met Gly Cys Leu Thr Val Val Ser Arg Val Ala
    50                  55                  60

Ala Gln Gln Gly Phe Asp Leu Asp Leu Gly Tyr Arg Leu Leu Ala Val
65                  70                  75                  80

Cys Ala Ala Asn Arg Asp Lys Phe Thr Pro Lys Ser Ala Ala Leu Leu
                85                  90                  95

Ser Ser Trp Cys Glu Glu Leu Gly Arg Leu Leu Leu Leu Arg His Gln
            100                 105                 110

Lys Ser Arg Gln Ser Asp Pro Pro Gly Lys Leu Pro Met Gln Pro Pro
        115                 120                 125

Leu Ser Ser Met Ser Ser Met Lys Pro Thr Leu Ser His Ser Asp Gly
    130                 135                 140

Ser Phe Pro Tyr Asp Ser Val Pro Trp Gln Gln Asn Thr Asn Gln Pro
145                 150                 155                 160

Pro Gly Ser Leu Ser Val Val Thr Thr Val Trp Gly Val Thr Asn Thr
                165                 170                 175

Ser Gln Ser Gln Val Leu Gly Asn Pro Met Ala Asn Ala Asn Asn Pro
            180                 185                 190

Met Asn Pro Gly Gly Asn Pro Met Ala Ser Gly Met Thr Thr Ser Asn
        195                 200                 205

Pro Gly Leu Asn Ser Pro Gln Phe Ala Gly Gln Gln Gln Gln Phe Ser
    210                 215                 220

Ala Lys Ala Gly Pro Ala Gln Pro Tyr Ile Gln Gln Ser Met Tyr Gly
225                 230                 235                 240

Arg Pro Asn Tyr Pro Gly Ser Gly Gly Phe Gly Ala Ser Tyr Pro Gly
                245                 250                 255

Gly Pro Asn Ala Pro Ala Gly Met Gly Ile Pro Pro His Thr Arg Pro
            260                 265                 270

Pro Ala Asp Phe Thr Gln Pro Ala Ala Ala Ala Ala Ala Ala Ala Val
        275                 280                 285

Ala Ala Ala Ala Ala Thr Ala Thr Ala Thr Ala Thr Ala Thr Val Ala
    290                 295                 300

Ala Leu Gln Glu Thr Gln Asn Lys Asp Ile Asn Gln Tyr Gly Pro Val
305                 310                 315                 320

Cys Ser Ser Phe Gln Met Gly Pro Thr Gln Ala Tyr Asn Ser Gln Phe
                325                 330                 335

Met Asn Gln Pro Gly Pro Arg Gly Pro Ala Ser Met Gly Gly Ser Met
            340                 345                 350

Asn Pro Ala Ser Met Ala Ala Gly Met Thr Pro Ser Gly Met Ser Gly
        355                 360                 365

Pro Pro Met Gly Met Asn Gln Pro Arg Pro Pro Gly Ile Ser Pro Phe
    370                 375                 380

Gly Thr His Gly Gln Arg Met Pro Gln Gln Thr Tyr Pro Gly Pro Arg
385                 390                 395                 400

Pro Gln Ser Leu Pro Ile Gln Asn Ile Lys Arg Pro Tyr Pro Gly Glu
                405                 410                 415

Pro Asn Tyr Gly Asn Gln Gln Tyr Gly Pro Asn Ser Gln Phe Pro Thr
            420                 425                 430

Gln Pro Gly Gln Tyr Pro Ala Pro Asn Pro Pro Arg Pro Leu Thr Ser
        435                 440                 445

Pro Asn Tyr Pro Gly Gln Arg Met Pro Ser Gln Pro Ser Ser Gly Gln
```

-continued

```
    450                 455                 460

Tyr Pro Pro Pro Thr Val Asn Met Gly Gln Tyr Tyr Lys Pro Glu Gln
465                 470                 475                 480

Phe Asn Gly Gln Asn Asn Thr Phe Ser Gly Ser Ser Tyr Ser Asn Tyr
                485                 490                 495

Ser Gln Gly Asn Val Asn Arg Pro Pro Arg Pro Val Pro Val Ala Asn
            500                 505                 510

Tyr Pro His Ser Pro Val Pro Gly Asn Pro Thr Pro Pro Met Thr Pro
        515                 520                 525

Gly Ser Ser Ile Pro Pro Tyr Leu Ser Pro Ser Gln Asp Val Lys Pro
    530                 535                 540

Pro Phe Pro Pro Asp Ile Lys Pro Asn Met Ser Ala Leu Pro Pro Pro
545                 550                 555                 560

Pro Ala Asn His Asn Asp Glu Leu Arg Leu Thr Phe Pro Val Arg Asp
                565                 570                 575

Gly Val Val Leu Glu Pro Phe Arg Leu Glu His Asn Leu Ala Val Ser
            580                 585                 590

Asn His Val Phe His Leu Arg Pro Thr Val His Gln Thr Leu Met Trp
        595                 600                 605

Arg Ser Asp Leu Glu Leu Gln Phe Lys Cys Tyr His His Glu Asp Arg
    610                 615                 620

Gln Met Asn Thr Asn Trp Pro Ala Ser Val Gln Val Ser Val Asn Ala
625                 630                 635                 640

Thr Pro Leu Thr Ile Glu Arg Gly Asp Asn Lys Thr Ser His Lys Pro
                645                 650                 655

Leu His Leu Lys His Val Cys Gln Pro Gly Arg Asn Thr Ile Gln Ile
            660                 665                 670

Thr Val Thr Ala Cys Cys Cys Ser His Leu Phe Val Leu Gln Leu Val
        675                 680                 685

His Arg Pro Ser Val Arg Ser Val Leu Gln Gly Leu Leu Lys Lys Arg
    690                 695                 700

Leu Leu Pro Ala Glu His Cys Ile Thr Lys Ile Lys Arg Asn Phe Ser
705                 710                 715                 720

Ser Val Ala Ala Ser Ser Gly Asn Thr Thr Leu Asn Gly Glu Asp Gly
                725                 730                 735

Val Glu Gln Thr Ala Ile Lys Val Ser Leu Lys Cys Pro Ile Thr Phe
            740                 745                 750

Arg Arg Ile Gln Leu Pro Ala Arg Gly His Asp Cys Lys His Val Gln
        755                 760                 765

Cys Phe Asp Leu Glu Ser Tyr Leu Gln Leu Asn Cys Glu Arg Gly Thr
    770                 775                 780

Trp Arg Cys Pro Val Cys Asn Lys Thr Ala Leu Leu Glu Gly Leu Glu
785                 790                 795                 800

Val Asp Gln Tyr Met Trp Gly Ile Leu Asn Ala Ile Gln His Ser Glu
                805                 810                 815

Phe Glu Glu Val Thr Ile Asp Pro Thr Cys Ser Trp Arg Pro Val Pro
            820                 825                 830

Ile Lys Ser Asp Leu His Ile Lys Asp Asp Pro Asp Gly Ile Pro Ser
        835                 840                 845

Lys Arg Phe Lys Thr Met Ser Pro Ser Gln Met Ile Met Pro Asn Val
    850                 855                 860

Met Glu Met Ile Ala Ala Leu Gly Pro Gly Pro Ser Pro Tyr Pro Leu
865                 870                 875                 880
```

```
Pro Pro Pro Pro Gly Gly Thr Asn Ser Asn Asp Tyr Ser Ser Gln Gly
                885                 890                 895

Asn Asn Tyr Gln Gly His Gly Asn Phe Asp Phe Pro His Gly Asn Pro
            900                 905                 910

Gly Gly Thr Ser Met Asn Asp Phe Met His Gly Pro Pro Gln Leu Ser
        915                 920                 925

His Pro Pro Asp Met Pro Asn Asn Met Ala Ala Leu Glu Lys Pro Leu
    930                 935                 940

Ser His Pro Met Gln Glu Thr Met Pro His Ala Gly Ser Ser Asp Gln
945                 950                 955                 960

Pro His Pro Ser Ile Gln Gln Gly Leu His Val Pro His Pro Ser Ser
                965                 970                 975

Gln Ser Gly Pro Pro Leu His His Ser Gly Ala Pro Pro Pro Pro Pro
            980                 985                 990

Ser Gln Pro Pro Arg Gln Pro Pro  Gln Ala Ala Pro Ser  Ser His Pro
        995                 1000                 1005

His Ser  Asp Leu Thr Phe Asn  Pro Ser Ser Ala Leu  Glu Gly Gln
    1010                 1015                 1020

Ala Gly  Ala Gln Gly Ala Ser  Asp Met Pro Glu Pro  Ser Leu Asp
    1025                 1030                 1035

Leu Leu  Pro Glu Leu Thr Asn  Pro Asp Glu Leu Leu  Ser Tyr Leu
    1040                 1045                 1050

Asp Pro  Pro Asp Leu Pro Ser  Asn Ser Asn Asp Asp  Leu Leu Ser
    1055                 1060                 1065

Leu Phe  Glu Asn Asn
    1070
```

<210> SEQ ID NO 11
<211> LENGTH: 7632
<212> TYPE: DNA
<213> ORGANISM: Homo sapiens
<220> FEATURE:
<221> NAME/KEY: misc_feature
<222> LOCATION: (1)..(7632)
<223> OTHER INFORMATION: ZMIZ1 X2 transcript

<400> SEQUENCE: 11

```
tcacttactc accccctaac gccgagttcc ttttcactgt ctgtggacat taaaaaagcg     60

agcggcggcg gcgggcgccg gggagagcgg gcggccgggc ggcaggcggg cgagcagcga    120

tcgggcggcc gagcgagcga gcaacgccgg cgcagcgcgg tgaccccagc cccagccggc    180

gcggagcagg agccggagcc gagcggatct cggcgccctc gctgcgctcc tcccggcccg    240

agcctgccct acccggcggt ggcggcggcg cgtcctccag cggcggcagc ggcgctcgca    300

gcgcccggac tcacggcagc tgtgttctga tttcgtacta ctgctggggc tgccacctcc    360

tcctccagac gctctcagca gacttgagtc ctggtccttc tgcagaggcc tgagcaggag    420

gaagaggagg aggcccgttg gcgtcggacc aatgctgcaa ggggtgtgag gagaggagcc    480

gctgtttttc actgagctgc catacccga aaggatggag ctggagtgag gtggaggggc    540

cgcaagctgc tgaccggcgt gtggaacact ggtggtttgc agatcactga ggctggacaa    600

cgttcatggc tctcgggtag aacctagtga aacggccaga atgaattcta tggacaggca    660

catccagcag accaatgacc gactgcagtg catcaagcag cacttacaga atcctgccaa    720

cttccacaat gccgccacgg agctgctgga ctggtgcgga gacccacggg ccttccagcg    780

gcccttcgag cagagcctga tgggctgttt gacggtggtc agtcgggtgg cagcccagca    840
```

```
aggctttgac ctggacctcg gctacagact gctggctgtg tgtgctgcaa accgagacaa    900
gttcaccccg aagtctgccg ccttgttgtc ctcctggtgc gaagagctcg gccgcctgct    960
gctgctccga catcagaaga gccgccagag cgatccccct gggaaactcc ccatgcagcc   1020
ccctctcagc tccatgagct ccatgaaacc cactctgtcg cacagtgatg ggtcgttccc   1080
ctatgactct gtcccttggc agcagaacac caaccagcct cccggctccc tttccgtggt   1140
caccacggtt tggggagtaa ccaacacatc ccagagccag gtccttggga accctatggc   1200
caatgccaac aaccccatga atccaggcgg caaccccatg gcgtcgggca tgaccaccag   1260
caacccaggc ctcaactccc cacagtttgc ggggcagcag cagcagttct cagccaaggc   1320
tggccccgct cagccctaca tccagcagag catgtatggc cggcccaact accccggcag   1380
cgggggcttt ggggccagtt accctggggg tcctaacgcc cccgcaggca tgggcatccc   1440
tccgcacacc aggccgcctg ctgacttcac tcagcccgcg gcagccgctg cagcagcggc   1500
agtggcagca gcagcagcca cagctacagc cacagccacg gccactgtgg cagccctgca   1560
ggagacacag aacaaggata taaaccagta tggaccggtc tgttcctctt tccagatggg   1620
tcccacccag gcgtataaca gccaattcat gaaccagccc gggccgcggg ggcctgcctc   1680
catggggggc agcatgaacc ccgcgagcat ggcggctggc atgacgccct cggggatgag   1740
cggccctccc atgggcatga accagccccg gccgcccggc atcagcccct ttggcacaca   1800
cgggcagcgg atgccccagc agacctaccc gggcccccgg ccccagtccc ttcctattca   1860
gaacataaag aggccatacc ctggagagcc caactatgga aaccagcaat atggaccaaa   1920
cagccagttc ccccacccagc caggccagta cccagccccc aaccccccga ggccactcac   1980
ctcccccaac tacccaggac agaggatgcc cagccagccg agctccgggc agtacccgcc   2040
ccccacggtc aacatggggc agtattacaa gccagaacag tttaatggac aaaataacac   2100
gttctcggga agcagctaca gtaactacag ccaagggaat gtcaacaggc ctcccaggcc   2160
ggttcctgtg gcaaattacc cccactcacc tgttccaggg aaccccacac cccccatgac   2220
ccctgggagc agcatccctc catacctgtc ccccagccaa gacgtcaaac caccccttccc   2280
gcctgacatc aagccaaata tgagcgctct gccaccaccc ccagccaacc acaatgacga   2340
gctgcggctc acattccctg tgcgggatgg cgtggtgctg gagcccttcc gcctggagca   2400
caacctggcg gtcagcaacc atgtgttcca cctgcggccc acggtccacc agacgctgat   2460
gtggaggtct gacctggagc tgcagttcaa gtgctaccac cacgaggacc ggcagatgaa   2520
caccaactgg cccgcctcgg tgcaggtcag cgtgaacgcc acgcccctca ccattgagcg   2580
cggcgacaac aagacctccc acaagcccct gcacctgaag cacgtgtgcc agccgggccg   2640
caacaccatc cagatcaccg tcacggcctg ctgctgctcc cacctcttcg tgctgcagct   2700
ggtacaccgg ccctccgtcc gctctgtgct gcaaggactc ctcaagaagc gcctcctgcc   2760
cgcagagcac tgtatcacga aaatcaagcg gaatttcagc agcgtggctg cctcctcggg   2820
caacacgacc ctcaacgggg aggatggggt ggagcagacg gccatcaagg tgtctctgaa   2880
gtgccccatc acattccggc gcatccagct gcctgctcga ggacacgatt gcaagcatgt   2940
gcagtgcttt gatctggagt catacctgca gctgaattgc gagagaggga cctggaggtg   3000
tcctgtgtgc aataaaaccg ctctgctgga gggcctggag gtggatcagt acatgtgggg   3060
aatcctgaat gccatccaac actccgagtt tgaagaggtc accatcgatc ccacgtgcag   3120
ctggcggccg gtgcccatca agtcggactt acacatcaag gacgaccctg atggcatccc   3180
```

-continued

```
ctccaagcgg ttcaagacca tgagtcccag ccagatgatc atgcccaatg tcatggagat   3240
gatcgcagcc ctgggccccg gcccgtcccc ctatcccctc ccgcctcccc caggggggcac   3300
caactccaac gactacagca gccaaggcaa caactaccaa ggccatggca actttgactt   3360
cccccacggg aaccctggag ggacatccat gaatgacttc atgcacgggc ccccccagct   3420
ctcccacccc ccggacatgc ccaacaacat ggccgccctc gagaaacccc tcagccaccc   3480
catgcaggaa actatgccac acgctggcag ctctgaccag ccccacccct ccatacaaca   3540
aggtttgcac gtaccacacc ccagcagcca gtcagggcct ccattacatc acagtggggc   3600
tcctcctcct cctccttccc agcctccccg gcagccgcca caggccgctc ccagcagcca   3660
tccacacagc gacctgacct ttaacccctc ctcagcctta gagggtcagg ccggagcgca   3720
gggagcgtcc gacatgccgg agccttcgct ggatctcctt cccgaactca caaatcctga   3780
cgagctcctg tcttatctgg accccccga cctgccgagc aatagtaacg atgacctcct   3840
gtctctattt gagaacaact gagggccacc cggtcggggc catccctcca cactctgcat   3900
cctaccccac ctacccaaca cacttttcca cctgggagcc tgtgccctca gaccgccccg   3960
caccagagcc acgggctgtg gggcggggag ccctcccccg ctgcagccct ctcagaacag   4020
aggggtaggg agggtgcacc agtgcaccag gaaggctgtg tgggtctgga gcccacgtcc   4080
cacctccaca cccttggctt gggcccatgc ccagcgcagg cctgaagacc accctcccga   4140
gaggaaccag cccggtaaga gggcacacgc tgatgcggct tcccggtccc tccgcgtgtg   4200
ccgattccag atgaccttcc agtgtcccca aggttcttcc atcttctaga ctgtaaccct   4260
gcctccctgc ttcctggtcc agagcctccc tccagtgact gtggagcctg agaaggcccc   4320
cgggccccag catgggcccc gagccttgga ggagcactgg cagttggtgg cagtgagacc   4380
agcccaccca ccaccaccca ccacagaaaa gcacaaacct ctgggaaaga caacgtctct   4440
cgggggccag ggtcatcgg tttgacccct gacctataag ccaagatacc ccataaacac   4500
actcagaaag cagagaaaaa ggacaagagt ctgtgtttga gagggggtct gccattcctg   4560
cttggggact ggtggggaag agggccagga catcttctga gccaggacgt ccctgaggct   4620
ccacctccaa gctcagacag ggcccaggct tggggaacag agagagcagg tgtacaccca   4680
accaaagtga ttgtgccctt ggttgggggg cgcgggcata taacctgtca gaagcaaaca   4740
ggagcggcaa cttctaactt tgctccaagc cactctcttt ttaaacagca acaatttaaa   4800
gctatgaagt cacctggaga aaaggaacgt tgctcttgga cagcaagcaa accatttctc   4860
tccgtctgtt ctgtttttct cctagtccct ctcctgccac ctctccaaga cttccgtggg   4920
acacccactt ccctctgtcc tagttctctt tgtccaatca gatggcaagg gcagtgcgtg   4980
gaaaggccgg ggaggtgcag aaaccagagc ccagggcaat ggtgtctgtc cagcccctcc   5040
ctctgtccct gtgctccaag ctgcccccgg ctgcagccca ggccatggac atgtgcacca   5100
gtatgtacct gcaggcatgg gggggagggg ggcgtgtttc tgggcctgcc ccagacactg   5160
cccttggctg ccagcctacc ctgcctgcac tcctccacca tcacaatctc acccaaactc   5220
ctgctcactc aagcaaaagc agcctctggc cttccctcca ccgctttgct ccatctggct   5280
taccactctc cagggcctcc tggggagcct gtcctgtgtt cactttgttt caggctggtc   5340
tgtgccccgt gagccacatg gcctagggtg atgccaggtt gtcccgtcac tggggtccca   5400
tctgtaaatt ctttgcgccc ttcccggctg ctgcctgggg ccctttcctg ctctcccgtc   5460
cgctgtgggt ggtccccagc tctcctctgt gggttttacc ggaaaggtgg ccccagctgt   5520
tgacttccag tcactgtccc agacggcaca aggttttctg taggaaagct gccattgccc   5580
```

```
cggccccttt tcttcctttg tcccgttgtc gaggtttttt caaatagcgt gttgttcagt   5640
atgcaaatca attattttaa gaatcgcttt tgtaaatatc tttgtgaata ttttagtatc   5700
gtctttgata atattcaaca ttttcatgac ctggttatag cctttgctgg tgtttttaaa   5760
atacctggac tcaatgacaa agaccgagtc ttcttttttt ttaaacaaaa acaaaaaaag   5820
caaccagggc tatttgtaca gttgaagggg tgaacagaat gggcggctgt gctgggagtt   5880
ggaagaccgg gcagcccgct atttagagcc atccctcagt cagctggcag ggacaagcca   5940
acgccaggta gcatgtggcc acccttgccc agtgtctgtg gcctggcaag tggccacgcc   6000
ctgtgtcaga ccatctggga attaagctcc agacagactt acagatgcct tccttaggag   6060
ttcttgcttc ttgcgttgat actttgcccc agaaaggcct gggattcatt ctggttctta   6120
tcagggtgtg tccacactct gctcacaggt ggatccacgg ctttccagtg cggagagtcg   6180
agatgctccc tgcagcccag gccccgggca cctcctgcaa ccatctctgg gctcagcacc   6240
tgaggcgggt ttcctgggtc ccctctccag caagcctcca ccagcaagct cggcccagag   6300
cttcccttcc ggctggctct gaaccgtgcg tggtgcctac agcctgcagt ctggagacaa   6360
gctcttccgg agtgctctgg gagccaggcc agggtgtgag ggaggtgcag aggcatccgg   6420
ggcgggagca agccccaggt tgtgacaggt gcaggtagac aacgcccata aacagagatg   6480
gtcctgaact ctggagagat ccttccctga tcctttcgga cgactacttg gagccataag   6540
taacctcagc aaaaacgagg cctctgcaag ccactttcc atgccaagca tccacccggc   6600
ccacaggcat gtttctgccg ccactccgca agatggacag ggagccagca ggcaggcggg   6660
aagggccaag tacaggcaat cacccccatc ttcttggttt gaagctttat ccatgtatca   6720
tgttccgtgt agccatttta ttttttaaga aactgctaat actttctccc taatggaagc   6780
cctgatcccc cagagagcta caggtctgct cccgacgggc ctcgggcctg acccgtccac   6840
acagggccgt gtcaacagca gcgactcaag ggacgtgtgt acatatgtaa atgagaaata   6900
gagacgtgtc aacagatgca ttcatttctc ttggaatgtg tattgttttt attttgcgaa   6960
acaaaacaaa acaaaaaaaa aagcttggaa ctccatcacg tggaaaaact agatcctgtt   7020
ggttatagca tttgtgagtt ctccacgtct gtctctctcg ctcatgtaat atactctgac   7080
cctgagtgga aaggggtttt tgttctgttt ttattttacc tacatgtact atttagcttc   7140
agtgtactag tcctgccacc tgtgtatttt tagggtgcta tggaaataat gaaaagaaac   7200
ggggatttca gaagaaaatt gtaaccaaat tcatactttg tataattttt gatatcatga   7260
tcacaggtga ttcacacgta cacacataaa cacacccacc agtgcagcct gaagtaactc   7320
ccacagaaac catcatcgtc tttgtacatc gtatgtacaa tgcaatcatt tcatacttta   7380
aactggtcaa aaaactaatt gtgatttcta gtcttgcaaa gctgtatgta gttagatgat   7440
gtgacaacct ctaatattta tctaataaat atgtattcag atgaaacctg tatattaggt   7500
gttcatgtgg ttattttgta tttaaagatc aaattatttg actattgcta gacatttcta   7560
tactctgttg taacactgag gtatctcatt tgcccatgtt aatttttttc taaataaatt   7620
gacaaaaaca aa                                                       7632
```

<210> SEQ ID NO 12
<211> LENGTH: 1073
<212> TYPE: PRT
<213> ORGANISM: Homo sapiens
<220> FEATURE:
<221> NAME/KEY: MISC_FEATURE
<222> LOCATION: (1)..(1073)

<223> OTHER INFORMATION: ZMIZ1 X3 amino acid sequence

<400> SEQUENCE: 12

```
Met Asn Ser Met Asp Arg His Ile Gln Gln Thr Asn Asp Arg Leu Gln
1               5                   10                  15

Cys Ile Lys Gln His Leu Gln Asn Pro Ala Asn Phe His Asn Ala Ala
            20                  25                  30

Thr Glu Leu Leu Asp Trp Cys Gly Asp Pro Arg Ala Phe Gln Arg Pro
        35                  40                  45

Phe Glu Gln Ser Leu Met Gly Cys Leu Thr Val Val Ser Arg Val Ala
    50                  55                  60

Ala Gln Gln Gly Phe Asp Leu Asp Leu Gly Tyr Arg Leu Leu Ala Val
65                  70                  75                  80

Cys Ala Ala Asn Arg Asp Lys Phe Thr Pro Lys Ser Ala Ala Leu Leu
                85                  90                  95

Ser Ser Trp Cys Glu Glu Leu Gly Arg Leu Leu Leu Leu Arg His Gln
            100                 105                 110

Lys Ser Arg Gln Ser Asp Pro Pro Gly Lys Leu Pro Met Gln Pro Pro
        115                 120                 125

Leu Ser Ser Met Ser Ser Met Lys Pro Thr Leu Ser His Ser Asp Gly
    130                 135                 140

Ser Phe Pro Tyr Asp Ser Val Pro Trp Gln Gln Asn Thr Asn Gln Pro
145                 150                 155                 160

Pro Gly Ser Leu Ser Val Val Thr Thr Val Trp Gly Val Thr Asn Thr
                165                 170                 175

Ser Gln Ser Gln Val Leu Gly Asn Pro Met Ala Asn Ala Asn Asn Pro
            180                 185                 190

Met Asn Pro Gly Gly Asn Pro Met Ala Ser Gly Met Thr Thr Ser Asn
        195                 200                 205

Pro Gly Leu Asn Ser Pro Gln Phe Ala Gly Gln Gln Gln Gln Phe Ser
    210                 215                 220

Ala Lys Ala Gly Pro Ala Gln Pro Tyr Ile Gln Gln Ser Met Tyr Gly
225                 230                 235                 240

Arg Pro Asn Tyr Pro Gly Ser Gly Gly Phe Gly Ala Ser Tyr Pro Gly
                245                 250                 255

Gly Pro Asn Ala Pro Ala Gly Met Gly Ile Pro Pro His Thr Arg Pro
            260                 265                 270

Pro Ala Asp Phe Thr Gln Pro Ala Ala Ala Ala Ala Ala Ala Ala Val
        275                 280                 285

Ala Ala Ala Ala Ala Thr Ala Thr Ala Thr Ala Thr Ala Thr Val Ala
    290                 295                 300

Ala Leu Gln Glu Thr Gln Asn Lys Asp Ile Asn Gln Tyr Gly Pro Val
305                 310                 315                 320

Cys Ser Ser Phe Gln Met Gly Pro Thr Gln Ala Tyr Asn Ser Gln Phe
                325                 330                 335

Met Asn Gln Pro Gly Pro Arg Gly Pro Ala Ser Met Gly Gly Ser Met
            340                 345                 350

Asn Pro Ala Ser Met Ala Ala Gly Met Thr Pro Ser Gly Met Ser Gly
        355                 360                 365

Pro Pro Met Gly Met Asn Gln Pro Arg Pro Pro Gly Ile Ser Pro Phe
    370                 375                 380

Gly Thr His Gly Gln Arg Met Pro Gln Gln Thr Tyr Pro Gly Pro Arg
385                 390                 395                 400
```

```
Pro Gln Ser Leu Pro Ile Gln Asn Ile Lys Arg Pro Tyr Pro Gly Glu
                405                 410                 415

Pro Asn Tyr Gly Asn Gln Gln Tyr Gly Pro Asn Ser Gln Phe Pro Thr
            420                 425                 430

Gln Pro Gly Gln Tyr Pro Ala Pro Asn Pro Pro Arg Pro Leu Thr Ser
        435                 440                 445

Pro Asn Tyr Pro Gly Gln Arg Met Pro Ser Gln Pro Ser Ser Gly Gln
    450                 455                 460

Tyr Pro Pro Pro Thr Val Asn Met Gly Gln Tyr Tyr Lys Pro Glu Gln
465                 470                 475                 480

Phe Asn Gly Gln Asn Asn Thr Phe Ser Gly Ser Ser Tyr Ser Asn Tyr
                485                 490                 495

Ser Gln Gly Asn Val Asn Arg Pro Pro Arg Pro Val Pro Val Ala Asn
            500                 505                 510

Tyr Pro His Ser Pro Val Pro Gly Asn Pro Thr Pro Pro Met Thr Pro
        515                 520                 525

Gly Ser Ser Ile Pro Pro Tyr Leu Ser Pro Ser Gln Asp Val Lys Pro
    530                 535                 540

Pro Phe Pro Pro Asp Ile Lys Pro Asn Met Ser Ala Leu Pro Pro Pro
545                 550                 555                 560

Pro Ala Asn His Asn Asp Glu Leu Arg Leu Thr Phe Pro Val Arg Asp
                565                 570                 575

Gly Val Val Leu Glu Pro Phe Arg Leu Glu His Asn Leu Ala Val Ser
            580                 585                 590

Asn His Val Phe His Leu Arg Pro Thr Val His Gln Thr Leu Met Trp
        595                 600                 605

Arg Ser Asp Leu Glu Leu Gln Phe Lys Cys Tyr His His Glu Asp Arg
    610                 615                 620

Gln Met Asn Thr Asn Trp Pro Ala Ser Val Gln Val Ser Val Asn Ala
625                 630                 635                 640

Thr Pro Leu Thr Ile Glu Arg Gly Asp Asn Lys Thr Ser His Lys Pro
                645                 650                 655

Leu His Leu Lys His Val Cys Gln Pro Gly Arg Asn Thr Ile Gln Ile
            660                 665                 670

Thr Val Thr Ala Cys Cys Cys Ser His Leu Phe Val Leu Gln Leu Val
        675                 680                 685

His Arg Pro Ser Val Arg Ser Val Leu Gln Gly Leu Leu Lys Lys Arg
    690                 695                 700

Leu Leu Pro Ala Glu His Cys Ile Thr Lys Ile Lys Arg Asn Phe Ser
705                 710                 715                 720

Ser Val Ala Ala Ser Ser Gly Asn Thr Thr Leu Asn Gly Glu Asp Gly
                725                 730                 735

Val Glu Gln Thr Ala Ile Lys Val Ser Leu Lys Cys Pro Ile Thr Phe
            740                 745                 750

Arg Arg Ile Gln Leu Pro Ala Arg Gly His Asp Cys Lys His Val Gln
        755                 760                 765

Cys Phe Asp Leu Glu Ser Tyr Leu Gln Leu Asn Cys Glu Arg Gly Thr
    770                 775                 780

Trp Arg Cys Pro Val Cys Asn Lys Thr Ala Leu Leu Glu Gly Leu Glu
785                 790                 795                 800

Val Asp Gln Tyr Met Trp Gly Ile Leu Asn Ala Ile Gln His Ser Glu
                805                 810                 815

Phe Glu Glu Val Thr Ile Asp Pro Thr Cys Ser Trp Arg Pro Val Pro
```

```
            820                 825                 830

Ile Lys Ser Asp Leu His Ile Lys Asp Asp Pro Asp Gly Ile Pro Ser
        835                 840                 845

Lys Arg Phe Lys Thr Met Ser Pro Ser Gln Met Ile Met Pro Asn Val
    850                 855                 860

Met Glu Met Ile Ala Ala Leu Gly Pro Gly Pro Ser Pro Tyr Pro Leu
865                 870                 875                 880

Pro Pro Pro Pro Gly Gly Thr Asn Ser Asn Asp Tyr Ser Ser Gln Gly
                885                 890                 895

Asn Asn Tyr Gln Gly His Gly Asn Phe Asp Phe Pro His Gly Asn Pro
            900                 905                 910

Gly Gly Thr Ser Met Asn Asp Phe Met His Gly Pro Pro Gln Leu Ser
        915                 920                 925

His Pro Pro Asp Met Pro Asn Asn Met Ala Ala Leu Glu Lys Pro Leu
    930                 935                 940

Ser His Pro Met Gln Glu Thr Met Pro His Ala Gly Ser Ser Asp Gln
945                 950                 955                 960

Pro His Pro Ser Ile Gln Gln Gly Leu His Val Pro His Pro Ser Ser
                965                 970                 975

Gln Ser Gly Pro Pro Leu His His Ser Gly Ala Pro Pro Pro Pro Pro
            980                 985                 990

Ser Gln Pro Pro Arg Gln Pro Pro  Gln Ala Ala Pro Ser  Ser His Pro
        995                 1000                 1005

His Ser  Asp Leu Thr Phe Asn  Pro Ser Ser Ala Leu  Glu Gly Gln
    1010                 1015                 1020

Ala Gly  Ala Gln Gly Ala Ser  Asp Met Pro Glu Pro  Ser Leu Asp
    1025                 1030                 1035

Leu Leu  Pro Glu Leu Thr Asn  Pro Asp Glu Leu Leu  Ser Tyr Leu
    1040                 1045                 1050

Asp Pro  Pro Asp Leu Pro Ser  Asn Ser Asn Asp Asp  Leu Leu Ser
    1055                 1060                 1065

Leu Phe  Glu Asn Asn
    1070


<210> SEQ ID NO 13
<211> LENGTH: 7554
<212> TYPE: DNA
<213> ORGANISM: Homo sapiens
<220> FEATURE:
<221> NAME/KEY: misc_feature
<222> LOCATION: (1)..(7554)
<223> OTHER INFORMATION: ZMIZ1 X4 transcript

<400> SEQUENCE: 13

tcacttactc accccctaac gccgagttcc ttttcactgt ctgtggacat taaaaaagcg     60

agcggcggcg gcgggcgccg gggagagcgg gcggccgggc ggcaggcggg cgagcagcga    120

tcgggcggcc gagcgagcga gcaacgccgg cgcagcgcgg tgaccccagc cccagccggc    180

gcggagcagg agccggagcc gagcggatct cggcgccctc gctgcgctcc tcccggcccg    240

agcctgccct acccggcggt ggcggcggcg cgtcctccag cggcggcagc ggcgctcgca    300

gcgcccggac tcacggcagc tgtgttctga tttcgtacta ctgctggggc tgccacctcc    360

tcctccagac gctctcagca gacttgagtc ctggtccttc tgcagaggcc tgagcaggag    420

gaagaggagg aggcccgttg gcgtcggacc aatgctgcaa ggggtgtgag gagaggagcc    480

gctgtttttc actgagctgc catacccga aaggctggac aacgttcatg gctctcgggt     540
```

```
agaacctagt gaaacggcca gaatgaattc tatggacagg cacatccagc agaccaatga    600
ccgactgcag tgcatcaagc agcacttaca gaatcctgcc aacttccaca atgccgccac    660
ggagctgctg gactggtgcg gagacccacg ggccttccag cggcccttcg agcagagcct    720
gatgggctgt ttgacggtgg tcagtcgggt ggcagcccag caaggctttg acctggacct    780
cggctacaga ctgctggctg tgtgtgctgc aaaccgagac aagttcaccc cgaagtctgc    840
cgccttgttg tcctcctggt gcgaagagct cggccgcctg ctgctgctcc gacatcagaa    900
gagccgccag agcgatcccc ctgggaaact ccccatgcag cccccctctca gctccatgag    960
ctccatgaaa cccactctgt cgcacagtga tgggtcgttc ccctatgact ctgtcccttg   1020
gcagcagaac accaaccagc ctcccggctc cctttccgtg gtcaccacgg tttggggagt   1080
aaccaacaca tcccagagcc aggtccttgg gaaccctatg gccaatgcca acaaccccat   1140
gaatccaggc ggcaacccca tggcgtcggg catgaccacc agcaacccag gcctcaactc   1200
cccacagttt gcggggcagc agcagcagtt ctcagccaag gctggccccg ctcagcccta   1260
catccagcag agcatgtatg gccggcccaa ctaccccggc agcgggggct ttggggccag   1320
ttaccctggg ggtcctaacg cccccgcagg catgggcatc cctccgcaca ccaggccgcc   1380
tgctgacttc actcagcccg cggcagccgc tgcagcagcg gcagtggcag cagcagcagc   1440
cacagctaca gccacagcca cggccactgt ggcagccctg caggagacac agaacaagga   1500
tataaaccag tatggaccgg tctgttcctc tttccagatg ggtcccaccc aggcgtataa   1560
cagccaattc atgaaccagc ccgggccgcg ggggcctgcc tccatggggg gcagcatgaa   1620
ccccgcgagc atggcggctg gcatgacgcc ctcggggatg agcggccctc ccatgggcat   1680
gaaccagccc cggccgcccg gcatcagccc ctttggcaca cacgggcagc ggatgcccca   1740
gcagacctac ccgggccccc ggccccagtc ccttcctatt cagaacataa agaggccata   1800
ccctggagag cccaactatg gaaaccagca atatggacca aacagccagt tccccaccca   1860
gccaggccag tacccagccc ccaacccccc gaggccactc acctccccca actacccagg   1920
acagaggatg cccagccagc cgagctccgg gcagtacccg ccccccacgg tcaacatggg   1980
gcagtattac aagccagaac agtttaatgg acaaaataac acgttctcgg gaagcagcta   2040
cagtaactac agccaaggga atgtcaacag gcctcccagg ccggttcctg tggcaaatta   2100
cccccactca cctgttccag ggaaccccac accccccatg acccctggga gcagcatccc   2160
tccatacctg tcccccagcc aagacgtcaa accacccttc ccgcctgaca tcaagccaaa   2220
tatgagcgct ctgccaccac ccccagccaa ccacaatgac gagctgcggc tcacattccc   2280
tgtgcgggat ggcgtggtgc tggagccctt ccgcctggag cacaacctgg cggtcagcaa   2340
ccatgtgttc cacctgcggc ccacggtcca ccagacgctg atgtggaggt ctgacctgga   2400
gctgcagttc aagtgctacc accacgagga ccggcagatg aacaccaact ggcccgcctc   2460
ggtgcaggtc agcgtgaacg ccacgcccct caccattgag cgcggcgaca acaagacctc   2520
ccacaagccc ctgcacctga agcacgtgtg ccagccgggc cgcaacacca tccagatcac   2580
cgtcacggcc tgctgctgct cccacctctt cgtgctgcag ctggtacacc ggccctccgt   2640
ccgctctgtg ctgcaaggac tcctcaagaa gcgcctcctg cccgcagagc actgtatcac   2700
gaaaatcaag cggaatttca gcagcgtggc tgcctcctcg ggcaacacga ccctcaacgg   2760
ggaggatggg gtggagcaga cggccatcaa ggtgtctctg aagtgcccca tcacattccg   2820
gcgcatccag ctgcctgctc gaggacacga ttgcaagcat gtgcagtgct ttgatctgga   2880
```

```
gtcatacctg cagctgaatt gcgagagagg gacctggagg tgtcctgtgt gcaataaaac   2940
cgctctgctg gagggcctgg aggtggatca gtacatgtgg ggaatcctga atgccatcca   3000
acactccgag tttgaagagg tcaccatcga tcccacgtgc agctggcggc cggtgcccat   3060
caagtcggac ttacacatca aggacgaccc tgatggcatc cctccaagc ggttcaagac   3120
catgagtccc agccagatga tcatgcccaa tgtcatggag atgatcgcag ccctgggccc   3180
cggcccgtcc ccctatcccc tcccgcctcc cccagggggc accaactcca acgactacag   3240
cagccaaggc aacaactacc aaggccatgg caactttgac ttcccccacg ggaaccctgg   3300
agggacatcc atgaatgact tcatgcacgg gcccccccag ctctcccacc ccccggacat   3360
gcccaacaac atggccgccc tcgagaaacc cctcagccac cccatgcagg aaactatgcc   3420
acacgctggc agctctgacc agccccaccc ctccatacaa caaggtttgc acgtaccaca   3480
ccccagcagc cagtcagggc ctccattaca tcacagtggg gctcctcctc ctcctccttc   3540
ccagcctccc cggcagccgc cacaggccgc tcccagcagc catccacaca gcgacctgac   3600
ctttaacccc tcctcagcct tagagggtca ggccggagcg cagggagcgt ccgacatgcc   3660
ggagccttcg ctggatctcc ttcccgaact cacaaatcct gacgagctcc tgtcttatct   3720
ggaccccccc gacctgccga gcaatagtaa cgatgacctc ctgtctctat ttgagaacaa   3780
ctgagggcca cccggtcggg gccatccctc cacactctgc atcctacccc acctacccaa   3840
cacacttttc cacctgggag cctgtgccct cagaccgccc cgcaccagag ccacgggctg   3900
tggggcgggg agccctcccc cgctgcagcc ctctcagaac agaggggtag ggagggtgca   3960
ccagtgcacc aggaaggctg tgtgggtctg gagcccacgt cccacctcca caccccttggc   4020
ttgggcccat gcccagcgca ggcctgaaga ccaccctccc gagaggaacc agcccggtaa   4080
gagggcacac gctgatgcgg cttcccggtc cctccgcgtg tgccgattcc agatgacctt   4140
ccagtgtccc caaggttctt ccatcttcta gactgtaacc ctgcctccct gcttcctggt   4200
ccagagcctc cctccagtga ctgtggagcc tgagaaggcc cccgggcccc agcatgggcc   4260
ccgagccttg gaggagcact ggcagttggt ggcagtgaga ccagcccacc caccaccacc   4320
caccacagaa aagcacaaac ctctgggaaa gacaacgtct ctcgggggcc aggggtcatc   4380
ggtttgaccc ctgacctata agccaagata ccccataaac acactcagaa agcagagaaa   4440
aaggacaaga gtctgtgttt gagagggggt ctgccattcc tgcttgggga ctggtgggga   4500
agagggccag gacatcttct gagccaggac gtccctgagg ctccacctcc aagctcagac   4560
agggcccagg cttggggaac agagagagca ggtgtacacc caaccaaagt gattgtgccc   4620
ttggttgggg ggcgcgggca tataacctgt cagaagcaaa caggagcggc aacttctaac   4680
tttgctccaa gccactctct ttttaaacag caacaattta aagctatgaa gtcacctgga   4740
gaaaaggaac gttgctcttg gacagcaagc aaaccatttc tctccgtctg ttctgttttt   4800
ctcctagtcc ctctcctgcc acctctccaa gacttccgtg ggacacccac ttccctctgt   4860
cctagttctc tttgtccaat cagatggcaa gggcagtgcg tggaaaggcc ggggaggtgc   4920
agaaaccaga gcccagggca atggtgtctg tccagcccct ccctctgtcc ctgtgctcca   4980
agctgccccc ggctgcagcc caggccatgg acatgtgcac cagtatgtac ctgcaggcat   5040
gggggggagg ggggcgtgtt tctgggcctg ccccagacac tgcccttggc tgccagccta   5100
ccctgcctgc actcctccac catcacaatc tcacccaaac tcctgctcac tcaagcaaaa   5160
gcagcctctg gccttccctc caccgctttg ctccatctgg cttaccactc tccagggcct   5220
cctggggagc ctgtcctgtg ttcactttgt ttcaggctgg tctgtgcccc gtgagccaca   5280
```

```
tggcctaggg tgatgccagg ttgtcccgtc actggggtcc catctgtaaa ttctttgcgc   5340
ccttcccggc tgctgcctgg ggccctttcc tgctctcccg tccgctgtgg gtggtcccca   5400
gctctcctct gtgggtttta ccggaaaggt ggccccagct gttgacttcc agtcactgtc   5460
ccagacggca caaggttttc tgtaggaaag ctgccattgc cccggcccct tttcttcctt   5520
tgtcccgttg tcgaggtttt ttcaaatagc gtgttgttca gtatgcaaat caattatttt   5580
aagaatcgct tttgtaaata tctttgtgaa tattttagta tcgtctttga taatattcaa   5640
cattttcatg acctggttat agcctttgct ggtgttttta aaatacctgg actcaatgac   5700
aaagaccgag tcttcttttt ttttaaacaa aaacaaaaaa agcaaccagg gctatttgta   5760
cagttgaagg ggtgaacaga atgggcggct gtgctgggag ttggaagacc gggcagcccg   5820
ctatttagag ccatccctca gtcagctggc agggacaagc caacgccagg tagcatgtgg   5880
ccacccttgc ccagtgtctg tggcctggca agtggccacg ccctgtgtca gaccatctgg   5940
gaattaagct ccagacagac ttacagatgc cttccttagg agttcttgct tcttgcgttg   6000
atactttgcc ccagaaaggc ctgggattca ttctggttct tatcagggtg tgtccacact   6060
ctgctcacag gtggatccac ggctttccag tgcggagagt cgagatgctc cctgcagccc   6120
aggccccggg cacctcctgc aaccatctct gggctcagca cctgaggcgg gtttcctggg   6180
tcccctctcc agcaagcctc caccagcaag ctcggcccag agcttccctt ccggctggct   6240
ctgaaccgtg cgtggtgcct acagcctgca gtctggagac aagctcttcc ggagtgctct   6300
gggagccagg ccagggtgtg agggaggtgc agaggcatcc ggggcgggag caagccccag   6360
gttgtgacag gtgcaggtag acaacgccca taaacagaga tggtcctgaa ctctggagag   6420
atccttccct gatcctttcg gacgactact tggagccata agtaacctca gcaaaaacga   6480
ggcctctgca agccactttt ccatgccaag catccacccg gcccacaggc atgtttctgc   6540
cgccactccg caagatggac agggagccag caggcaggcg ggaagggcca agtacaggca   6600
atcaccccca tcttcttggt ttgaagcttt atccatgtat catgttccgt gtagccattt   6660
tattttttaa gaaactgcta atactttctc cctaatggaa gccctgatcc cccagagagc   6720
tacaggtctg ctcccgacgg gcctcgggcc tgacccgtcc acacagggcc gtgtcaacag   6780
cagcgactca agggacgtgt gtacatatgt aaatgagaaa tagagacgtg tcaacagatg   6840
cattcatttc tcttggaatg tgtattgttt ttattttgcg aaacaaaaca aaacaaaaaa   6900
aaaagcttgg aactccatca cgtggaaaaa ctagatcctg ttggttatag catttgtgag   6960
ttctccacgt ctgtctctct cgctcatgta atatactctg accctgagtg gaaaggggtt   7020
tttgttctgt ttttatttta cctacatgta ctatttagct tcagtgtact agtcctgcca   7080
cctgtgtatt tttagggtgc tatggaaata atgaaaagaa acggggattt cagaagaaaa   7140
ttgtaaccaa attcatactt tgtataattt ttgatatcat gatcacaggt gattcacacg   7200
tacacacata aacacaccca ccagtgcagc ctgaagtaac tcccacagaa accatcatcg   7260
tctttgtaca tcgtatgtac aatgcaatca tttcatactt taaactggtc aaaaaactaa   7320
ttgtgatttc tagtcttgca aagctgtatg tagttagatg atgtgacaac ctctaatatt   7380
tatctaataa atatgtattc agatgaaacc tgtatattag gtgttcatgt ggttattttg   7440
tatttaaaga tcaaattatt tgactattgc tagacatttc tatactctgt tgtaacactg   7500
aggtatctca tttgcccatg ttaatttttt tctaaataaa ttgacaaaaa caaa         7554
```

<210> SEQ ID NO 14

<211> LENGTH: 1073
<212> TYPE: PRT
<213> ORGANISM: Homo sapiens
<220> FEATURE:
<221> NAME/KEY: MISC_FEATURE
<222> LOCATION: (1)..(1073)
<223> OTHER INFORMATION: ZMIZ1 X4 amino acid sequence

<400> SEQUENCE: 14

```
Met Asn Ser Met Asp Arg His Ile Gln Gln Thr Asn Asp Arg Leu Gln
1               5                   10                  15

Cys Ile Lys Gln His Leu Gln Asn Pro Ala Asn Phe His Asn Ala Ala
            20                  25                  30

Thr Glu Leu Leu Asp Trp Cys Gly Asp Pro Arg Ala Phe Gln Arg Pro
        35                  40                  45

Phe Glu Gln Ser Leu Met Gly Cys Leu Thr Val Val Ser Arg Val Ala
    50                  55                  60

Ala Gln Gln Gly Phe Asp Leu Asp Leu Gly Tyr Arg Leu Leu Ala Val
65                  70                  75                  80

Cys Ala Ala Asn Arg Asp Lys Phe Thr Pro Lys Ser Ala Ala Leu Leu
                85                  90                  95

Ser Ser Trp Cys Glu Glu Leu Gly Arg Leu Leu Leu Leu Arg His Gln
            100                 105                 110

Lys Ser Arg Gln Ser Asp Pro Pro Gly Lys Leu Pro Met Gln Pro Pro
        115                 120                 125

Leu Ser Ser Met Ser Ser Met Lys Pro Thr Leu Ser His Ser Asp Gly
    130                 135                 140

Ser Phe Pro Tyr Asp Ser Val Pro Trp Gln Gln Asn Thr Asn Gln Pro
145                 150                 155                 160

Pro Gly Ser Leu Ser Val Val Thr Thr Val Trp Gly Val Thr Asn Thr
                165                 170                 175

Ser Gln Ser Gln Val Leu Gly Asn Pro Met Ala Asn Ala Asn Asn Pro
            180                 185                 190

Met Asn Pro Gly Gly Asn Pro Met Ala Ser Gly Met Thr Thr Ser Asn
        195                 200                 205

Pro Gly Leu Asn Ser Pro Gln Phe Ala Gly Gln Gln Gln Gln Phe Ser
    210                 215                 220

Ala Lys Ala Gly Pro Ala Gln Pro Tyr Ile Gln Gln Ser Met Tyr Gly
225                 230                 235                 240

Arg Pro Asn Tyr Pro Gly Ser Gly Gly Phe Gly Ala Ser Tyr Pro Gly
                245                 250                 255

Gly Pro Asn Ala Pro Ala Gly Met Gly Ile Pro Pro His Thr Arg Pro
            260                 265                 270

Pro Ala Asp Phe Thr Gln Pro Ala Ala Ala Ala Ala Ala Ala Ala Val
        275                 280                 285

Ala Ala Ala Ala Ala Thr Ala Thr Ala Thr Ala Thr Ala Thr Val Ala
    290                 295                 300

Ala Leu Gln Glu Thr Gln Asn Lys Asp Ile Asn Gln Tyr Gly Pro Val
305                 310                 315                 320

Cys Ser Ser Phe Gln Met Gly Pro Thr Gln Ala Tyr Asn Ser Gln Phe
                325                 330                 335

Met Asn Gln Pro Gly Pro Arg Gly Pro Ala Ser Met Gly Gly Ser Met
            340                 345                 350

Asn Pro Ala Ser Met Ala Ala Gly Met Thr Pro Ser Gly Met Ser Gly
        355                 360                 365
```

```
Pro Pro Met Gly Met Asn Gln Pro Arg Pro Pro Gly Ile Ser Pro Phe
    370                 375                 380

Gly Thr His Gly Gln Arg Met Pro Gln Gln Thr Tyr Pro Gly Pro Arg
385                 390                 395                 400

Pro Gln Ser Leu Pro Ile Gln Asn Ile Lys Arg Pro Tyr Pro Gly Glu
                405                 410                 415

Pro Asn Tyr Gly Asn Gln Gln Tyr Gly Pro Asn Ser Gln Phe Pro Thr
            420                 425                 430

Gln Pro Gly Gln Tyr Pro Ala Pro Asn Pro Pro Arg Pro Leu Thr Ser
        435                 440                 445

Pro Asn Tyr Pro Gly Gln Arg Met Pro Ser Gln Pro Ser Ser Gly Gln
    450                 455                 460

Tyr Pro Pro Pro Thr Val Asn Met Gly Gln Tyr Tyr Lys Pro Glu Gln
465                 470                 475                 480

Phe Asn Gly Gln Asn Asn Thr Phe Ser Gly Ser Ser Tyr Ser Asn Tyr
                485                 490                 495

Ser Gln Gly Asn Val Asn Arg Pro Pro Arg Pro Val Pro Val Ala Asn
            500                 505                 510

Tyr Pro His Ser Pro Val Pro Gly Asn Pro Thr Pro Pro Met Thr Pro
        515                 520                 525

Gly Ser Ser Ile Pro Pro Tyr Leu Ser Pro Ser Gln Asp Val Lys Pro
    530                 535                 540

Pro Phe Pro Pro Asp Ile Lys Pro Asn Met Ser Ala Leu Pro Pro Pro
545                 550                 555                 560

Pro Ala Asn His Asn Asp Glu Leu Arg Leu Thr Phe Pro Val Arg Asp
                565                 570                 575

Gly Val Val Leu Glu Pro Phe Arg Leu Glu His Asn Leu Ala Val Ser
            580                 585                 590

Asn His Val Phe His Leu Arg Pro Thr Val His Gln Thr Leu Met Trp
        595                 600                 605

Arg Ser Asp Leu Glu Leu Gln Phe Lys Cys Tyr His His Glu Asp Arg
    610                 615                 620

Gln Met Asn Thr Asn Trp Pro Ala Ser Val Gln Val Ser Val Asn Ala
625                 630                 635                 640

Thr Pro Leu Thr Ile Glu Arg Gly Asp Asn Lys Thr Ser His Lys Pro
                645                 650                 655

Leu His Leu Lys His Val Cys Gln Pro Gly Arg Asn Thr Ile Gln Ile
            660                 665                 670

Thr Val Thr Ala Cys Cys Cys Ser His Leu Phe Val Leu Gln Leu Val
        675                 680                 685

His Arg Pro Ser Val Arg Ser Val Leu Gln Gly Leu Leu Lys Lys Arg
    690                 695                 700

Leu Leu Pro Ala Glu His Cys Ile Thr Lys Ile Lys Arg Asn Phe Ser
705                 710                 715                 720

Ser Val Ala Ala Ser Ser Gly Asn Thr Thr Leu Asn Gly Glu Asp Gly
                725                 730                 735

Val Glu Gln Thr Ala Ile Lys Val Ser Leu Lys Cys Pro Ile Thr Phe
            740                 745                 750

Arg Arg Ile Gln Leu Pro Ala Arg Gly His Asp Cys Lys His Val Gln
        755                 760                 765

Cys Phe Asp Leu Glu Ser Tyr Leu Gln Leu Asn Cys Glu Arg Gly Thr
    770                 775                 780

Trp Arg Cys Pro Val Cys Asn Lys Thr Ala Leu Leu Glu Gly Leu Glu
```

```
785                 790                 795                 800

Val Asp Gln Tyr Met Trp Gly Ile Leu Asn Ala Ile Gln His Ser Glu
                805                 810                 815

Phe Glu Glu Val Thr Ile Asp Pro Thr Cys Ser Trp Arg Pro Val Pro
            820                 825                 830

Ile Lys Ser Asp Leu His Ile Lys Asp Asp Pro Asp Gly Ile Pro Ser
        835                 840                 845

Lys Arg Phe Lys Thr Met Ser Pro Ser Gln Met Ile Met Pro Asn Val
    850                 855                 860

Met Glu Met Ile Ala Ala Leu Gly Pro Gly Pro Ser Pro Tyr Pro Leu
865                 870                 875                 880

Pro Pro Pro Pro Gly Gly Thr Asn Ser Asn Asp Tyr Ser Ser Gln Gly
                885                 890                 895

Asn Asn Tyr Gln Gly His Gly Asn Phe Asp Phe Pro His Gly Asn Pro
            900                 905                 910

Gly Gly Thr Ser Met Asn Asp Phe Met His Gly Pro Pro Gln Leu Ser
        915                 920                 925

His Pro Pro Asp Met Pro Asn Asn Met Ala Ala Leu Glu Lys Pro Leu
    930                 935                 940

Ser His Pro Met Gln Glu Thr Met Pro His Ala Gly Ser Ser Asp Gln
945                 950                 955                 960

Pro His Pro Ser Ile Gln Gln Gly Leu His Val Pro His Pro Ser Ser
                965                 970                 975

Gln Ser Gly Pro Pro Leu His His Ser Gly Ala Pro Pro Pro Pro Pro
            980                 985                 990

Ser Gln Pro Pro Arg Gln Pro Pro  Gln Ala Ala Pro Ser  Ser His Pro
        995                 1000                1005

His Ser  Asp Leu Thr Phe Asn  Pro Ser Ser Ala Leu  Glu Gly Gln
    1010                1015                1020

Ala Gly  Ala Gln Gly Ala Ser  Asp Met Pro Glu Pro  Ser Leu Asp
    1025                1030                1035

Leu Leu  Pro Glu Leu Thr Asn  Pro Asp Glu Leu Leu  Ser Tyr Leu
    1040                1045                1050

Asp Pro  Pro Asp Leu Pro Ser  Asn Ser Asn Asp Asp  Leu Leu Ser
    1055                1060                1065

Leu Phe  Glu Asn Asn
    1070


<210> SEQ ID NO 15
<211> LENGTH: 7372
<212> TYPE: DNA
<213> ORGANISM: Homo sapiens
<220> FEATURE:
<221> NAME/KEY: misc_feature
<222> LOCATION: (1)..(7372)
<223> OTHER INFORMATION: ZMIZ1 X5 transcript

<400> SEQUENCE: 15

acttactcac cccctaacgc cgagttcctt ttcactgtct gtggacatta aaaaagcgag      60

cggcggcggc gggcgccggg gagagcgggc ggccgggcgg caggcgggcg agcagcgatc     120

gggcggccga gcgagcgagc aacgccggcg cagcgcggtg accccagccc cagccggcgc     180

ggagcaggag ccggagccga gcggatctcg gcgccctcgc tgcgctcctc ccggcccgag     240

cctgccctac ccggcggtgg cggcggcgcg tcctccagcg gcggcagcgg cgctcgcagc     300

gcccggactc acggcagctg tgttctgatt tcgtactact gctggggctg ccacctcctc     360
```

-continued

```
ctccagacgc tctcagcaga cttgagtcct ggtccttctg cagaggcctg agcaggagga    420
agaggaggag gcccgttggc gtcggaccaa tgctgcaagg ggtgtgagga gaggagccgc    480
tgtttttcac tgagctgcca taccccgaaa gcaggatgga gctggagtga ggtggagggg    540
ccgcaagctg ctgaccggcg tgtggaacac tggtggtttg cagatcactg aggctggaca    600
acgttcatgg ctctcgggta gaacctagtg aaacggccag aatgaattct atggacaggc    660
acatccagca gaccaatgac cgactgcagt gcatcaagca gcacttacag aatcctgcca    720
acttccacaa tgccgccacg gagctgctgg actggtgcgg agacccacgg gccttccagc    780
ggcccttcga gcagagcctg atgggctgtt tgacggtggt cagtcgggtg gcagcccagc    840
aaggctttga cctggacctc ggctacagac tgctggctgt gtgtgctgca aaccgagaca    900
agttcacccc gaagtctgcc gccttgttgt cctcctggtg cgaagagctc ggccgcctgc    960
tgctgctccg acatcagaag agccgccaga gcgatccccc tgggaaactc cccatgcagc   1020
cccctctcag ctccatgagc tccatgaaac ccactctgtc gcacagtgat gggtcgttcc   1080
cctatgactc tgtcccttgg cagcagaaca ccaaccagcc tcccggctcc ctttccgtgg   1140
tcaccacggt ttggggagta accaacacat cccagagcca ggtccttggg aaccctatgg   1200
ccaatgccaa caaccccatg aatccaggcg gcaaccccat ggcgtcgggc atgaccacca   1260
gcaacccagg cctcaactcc ccacagtttg cggggcagca gcagcagttc tcagccaagg   1320
ctggccccgc tcagccctac atccagcaga gcatgtatgg ccggcccaac taccccggca   1380
gcgggggctt tggggccagt taccctgggg gtcctaacgc ccccgcaggc atgggcatcc   1440
ctccgcacac caggccgcct gctgacttca ctcagcccgc ggcagccgct gcagcagcgg   1500
cagtggcagc agcagcagcc acagctacag ccacagccac ggccactgtg gcagccctgc   1560
aggagacaca gaacaaggat ataaaccagt atggaccggt ctgttcctct ttccagatgg   1620
gtcccaccca ggcgtataac agccaattca tgaaccagcc cgggccgcgg gggcctgcct   1680
ccatgggggg cagcatgaac cccgcgagca tggcggctgg catgacgccc tcggggatga   1740
gcggccctcc catgggcatg aaccagcccc ggccgcccgg catcagcccc tttggcacac   1800
acgggcagcg gatgccccag cagacctacc cgggcccccg gccccagtcc cttcctattc   1860
agaacataaa gaggccatac cctggagagc ccaactatgg aaaccagcaa tatggaccaa   1920
acagccagtt ccccacccag ccaggccagt acccagcccc caacccccg aggccactca    1980
cctcccccaa ctacccagga cagaggatgc ccagccagcc gagctccggg cagtacccgc   2040
cccccacggt caacatgggg cagtattaca agccagaaca gtttaatgga caaaataaca   2100
cgttctcggg aagcagctac agtaactaca gccaagggaa tgtcaacagg cctcccaggc   2160
cggttcctgt ggcaaattac ccccactcac ctgttccagg gaaccccaca ccccccatga   2220
cccctgggag cagcatccct ccatacctgt cccccagcca agacgtcaaa ccaccccttcc  2280
cgcctgacat caagccaaat atgagcgctc tgccaccacc cccagccaac cacaatgacg   2340
agctgcggct cacattccct gtgcgggatg gcgtggtgct ggagcccttc cgcctggagc   2400
acaacctggc ggtcagcaac catgtgttcc acctgcggcc cacggtccac cagacgctga   2460
tgtggaggtc tgacctggag ctgcagttca agtgctacca ccacgaggac cggcagatga   2520
acaccaactg gcccgcctcg gtgcaggtca gcgtgaacgc cacgcccctc accattgagc   2580
gcggcgacaa caagacctcc cacaagcccc tgcacctgaa gcacgtgtgc cagccgggcc   2640
gcaacaccat ccagatcacc gtcacggcct gctgctgctc ccacctcttc gtgctgcagc   2700
```

```
tggtacaccg gccctccgtc cgctctgtgc tgcaaggact cctcaagaag cgcctcctgc   2760
ccgcagagca ctgtatcacg aaaatcaagc ggaatttcag cagcgtggct gcctcctcgg   2820
gcaacacgac cctcaacggg gaggatgggg tggagcagac ggccatcaag gtgtctctga   2880
agtgccccat cacattccgg cgcatccagc tgcctgctcg aggacacgat tgcaagcatg   2940
tgcagtgctt tgatctggag tcatacctgc agctgaattg cgagagaggg acctggaggt   3000
gtcctgtgtg caataaaacc gctctgctgg agggcctgga ggtggatcag tacatgtggg   3060
gaatcctgaa tgccatccaa cactccgagt ttgaagaggt caccatcgat cccacgtgca   3120
gctggcggcc ggtgcccatc aagtcggact tacacatcaa ggacgaccct gatggcatcc   3180
cctccaagcg gttcaagacc atgagtccca gccagatgat catgcccaat gtcatggaga   3240
tgatcgcagc cctgggcccc ggcccgtccc cctatcccct cccgcctccc ccagggggca   3300
ccaactccaa cgactacagc agccaaggca acaactacca aggccatggc aactttgact   3360
tcccccacgg gaaccctgga gggacatcca tgaatgactt catgcacggg cccccccagc   3420
tctcccaccc ccggacatg cccaacaaca tggccgccct cgagaaaccc ctcagccacc   3480
ccatgcagga aactctcctt cccgaactca caaatcctga cgagctcctg tcttatctgg   3540
acccccccga cctgccgagc aatagtaacg atgacctcct gtctctattt gagaacaact   3600
gagggccacc cggtcggggc catccctcca cactctgcat cctaccccac ctacccaaca   3660
cacttttcca cctgggagcc tgtgccctca gaccgccccg caccagagcc acgggctgtg   3720
gggcggggag ccctcccccg ctgcagccct ctcagaacag aggggtaggg agggtgcacc   3780
agtgcaccag gaaggctgtg tgggtctgga gcccacgtcc cacctccaca cccttggctt   3840
gggcccatgc ccagcgcagg cctgaagacc accctcccga gaggaaccag cccggtaaga   3900
gggcacacgc tgatgcggct tcccggtccc tccgcgtgtg ccgattccag atgaccttcc   3960
agtgtcccca aggttcttcc atcttctaga ctgtaaccct gcctccctgc ttcctggtcc   4020
agagcctccc tccagtgact gtggagcctg agaaggcccc cgggccccag catgggcccc   4080
gagccttgga ggagcactgg cagttggtgg cagtgagacc agcccaccca ccaccaccca   4140
ccacagaaaa gcacaaacct ctgggaaaga caacgtctct cgggggccag gggtcatcgg   4200
tttgacccct gacctataag ccaagatacc ccataaacac actcagaaag cagagaaaaa   4260
ggacaagagt ctgtgtttga gagggggtct gccattcctg cttggggact ggtggggaag   4320
agggccagga catcttctga gccaggacgt ccctgaggct ccacctccaa gctcagacag   4380
ggcccaggct tggggaacag agagagcagg tgtacaccca accaaagtga ttgtgccctt   4440
ggttgggggg cgcgggcata taacctgtca gaagcaaaca ggagcggcaa cttctaactt   4500
tgctccaagc cactctcttt ttaaacagca acaatttaaa gctatgaagt cacctggaga   4560
aaaggaacgt tgctcttgga cagcaagcaa accatttctc tccgtctgtt ctgtttttct   4620
cctagtccct ctcctgccac ctctccaaga cttccgtggg acacccactt ccctctgtcc   4680
tagttctctt tgtccaatca gatggcaagg gcagtgcgtg gaaaggccgg ggaggtgcag   4740
aaaccagagc ccagggcaat ggtgtctgtc cagcccctcc ctctgtccct gtgctccaag   4800
ctgcccccgg ctgcagccca ggccatggac atgtgcacca gtatgtacct gcaggcatgg   4860
gggggagggg ggcgtgtttc tgggcctgcc ccagacactg cccttggctg ccagcctacc   4920
ctgcctgcac tcctccacca tcacaatctc acccaaactc ctgctcactc aagcaaaagc   4980
agcctctggc cttccctcca ccgctttgct ccatctggct taccactctc cagggcctcc   5040
tggggagcct gtcctgtgtt cactttgttt caggctggtc tgtgccccgt gagccacatg   5100
```

```
gcctagggtg atgccaggtt gtcccgtcac tggggtccca tctgtaaatt ctttgcgccc   5160
ttcccggctg ctgcctgggg ccctttcctg ctctcccgtc cgctgtgggt ggtccccagc   5220
tctcctctgt gggttttacc ggaaaggtgg ccccagctgt tgacttccag tcactgtccc   5280
agacggcaca aggttttctg taggaaagct gccattgccc cggccccttt tcttcctttg   5340
tcccgttgtc gaggtttttt caaatagcgt gttgttcagt atgcaaatca attattttaa   5400
gaatcgcttt tgtaaatatc tttgtgaata ttttagtatc gtctttgata atattcaaca   5460
ttttcatgac ctggttatag cctttgctgg tgtttttaaa atacctggac tcaatgacaa   5520
agaccgagtc ttcttttttt ttaaacaaaa acaaaaaaag caaccagggc tatttgtaca   5580
gttgaagggg tgaacagaat gggcggctgt gctgggagtt ggaagaccgg gcagcccgct   5640
atttagagcc atccctcagt cagctggcag ggacaagcca acgccaggta gcatgtggcc   5700
acccttgccc agtgtctgtg gcctggcaag tggccacgcc ctgtgtcaga ccatctggga   5760
attaagctcc agacagactt acagatgcct tccttaggag ttcttgcttc ttgcgttgat   5820
actttgcccc agaaaggcct gggattcatt ctggttctta tcagggtgtg tccacactct   5880
gctcacaggt ggatccacgg ctttccagtg cggagagtcg agatgctccc tgcagcccag   5940
gccccgggca cctcctgcaa ccatctctgg gctcagcacc tgaggcgggt ttcctgggtc   6000
ccctctccag caagcctcca ccagcaagct cggcccagag cttcccttcc ggctggctct   6060
gaaccgtgcg tggtgcctac agcctgcagt ctggagacaa gctcttccgg agtgctctgg   6120
gagccaggcc agggtgtgag ggaggtgcag aggcatccgg ggcgggagca agccccaggt   6180
tgtgacaggt gcaggtagac aacgcccata aacagagatg gtcctgaact ctggagagat   6240
ccttccctga tcctttcgga cgactacttg gagccataag taacctcagc aaaaacgagg   6300
cctctgcaag ccacttttcc atgccaagca tccacccggc ccacaggcat gtttctgccg   6360
ccactccgca agatggacag ggagccagca ggcaggcggg aagggccaag tacaggcaat   6420
cacccccatc ttcttggttt gaagctttat ccatgtatca tgttccgtgt agccatttta   6480
ttttttaaga aactgctaat actttctccc taatggaagc cctgatcccc cagagagcta   6540
caggtctgct cccgacgggc ctcgggcctg acccgtccac acagggccgt gtcaacagca   6600
gcgactcaag ggacgtgtgt acatatgtaa atgagaaata gagacgtgtc aacagatgca   6660
ttcatttctc ttggaatgtg tattgttttt attttgcgaa acaaaacaaa acaaaaaaaa   6720
aagcttggaa ctccatcacg tggaaaaact agatcctgtt ggttatagca tttgtgagtt   6780
ctccacgtct gtctctctcg ctcatgtaat atactctgac cctgagtgga aaggggtttt   6840
tgttctgttt ttattttacc tacatgtact atttagcttc agtgtactag tcctgccacc   6900
tgtgtatttt tagggtgcta tggaaataat gaaaagaaac ggggatttca gaagaaaatt   6960
gtaaccaaat tcatactttg tataattttt gatatcatga tcacaggtga ttcacacgta   7020
cacacataaa cacacccacc agtgcagcct gaagtaactc ccacagaaac catcatcgtc   7080
tttgtacatc gtatgtacaa tgcaatcatt tcatacttta aactggtcaa aaaactaatt   7140
gtgatttcta gtcttgcaaa gctgtatgta gttagatgat gtgacaacct ctaatattta   7200
tctaataaat atgtattcag atgaaacctg tatattaggt gttcatgtgg ttattttgta   7260
tttaaagatc aaattatttg actattgcta gacatttcta tactctgttg taacactgag   7320
gtatctcatt tgcccatgtt aattttttttc taaataaatt gacaaaaaca aa          7372
```

<210> SEQ ID NO 16

```
<211> LENGTH: 986
<212> TYPE: PRT
<213> ORGANISM: Homo sapiens
<220> FEATURE:
<221> NAME/KEY: MISC_FEATURE
<222> LOCATION: (1)..(986)
<223> OTHER INFORMATION: ZMIZ1 X5 amino acid sequence

<400> SEQUENCE: 16

Met Asn Ser Met Asp Arg His Ile Gln Gln Thr Asn Asp Arg Leu Gln
1               5                   10                  15

Cys Ile Lys Gln His Leu Gln Asn Pro Ala Asn Phe His Asn Ala Ala
            20                  25                  30

Thr Glu Leu Leu Asp Trp Cys Gly Asp Pro Arg Ala Phe Gln Arg Pro
        35                  40                  45

Phe Glu Gln Ser Leu Met Gly Cys Leu Thr Val Val Ser Arg Val Ala
    50                  55                  60

Ala Gln Gln Gly Phe Asp Leu Asp Leu Gly Tyr Arg Leu Leu Ala Val
65                  70                  75                  80

Cys Ala Ala Asn Arg Asp Lys Phe Thr Pro Lys Ser Ala Ala Leu Leu
                85                  90                  95

Ser Ser Trp Cys Glu Glu Leu Gly Arg Leu Leu Leu Leu Arg His Gln
            100                 105                 110

Lys Ser Arg Gln Ser Asp Pro Pro Gly Lys Leu Pro Met Gln Pro Pro
        115                 120                 125

Leu Ser Ser Met Ser Ser Met Lys Pro Thr Leu Ser His Ser Asp Gly
    130                 135                 140

Ser Phe Pro Tyr Asp Ser Val Pro Trp Gln Gln Asn Thr Asn Gln Pro
145                 150                 155                 160

Pro Gly Ser Leu Ser Val Val Thr Thr Val Trp Gly Val Thr Asn Thr
                165                 170                 175

Ser Gln Ser Gln Val Leu Gly Asn Pro Met Ala Asn Ala Asn Asn Pro
            180                 185                 190

Met Asn Pro Gly Gly Asn Pro Met Ala Ser Gly Met Thr Thr Ser Asn
        195                 200                 205

Pro Gly Leu Asn Ser Pro Gln Phe Ala Gly Gln Gln Gln Gln Phe Ser
    210                 215                 220

Ala Lys Ala Gly Pro Ala Gln Pro Tyr Ile Gln Gln Ser Met Tyr Gly
225                 230                 235                 240

Arg Pro Asn Tyr Pro Gly Ser Gly Gly Phe Gly Ala Ser Tyr Pro Gly
                245                 250                 255

Gly Pro Asn Ala Pro Ala Gly Met Gly Ile Pro Pro His Thr Arg Pro
            260                 265                 270

Pro Ala Asp Phe Thr Gln Pro Ala Ala Ala Ala Ala Ala Ala Ala Val
        275                 280                 285

Ala Ala Ala Ala Ala Thr Ala Thr Ala Thr Ala Thr Ala Thr Val Ala
    290                 295                 300

Ala Leu Gln Glu Thr Gln Asn Lys Asp Ile Asn Gln Tyr Gly Pro Val
305                 310                 315                 320

Cys Ser Ser Phe Gln Met Gly Pro Thr Gln Ala Tyr Asn Ser Gln Phe
                325                 330                 335

Met Asn Gln Pro Gly Pro Arg Gly Pro Ala Ser Met Gly Gly Ser Met
            340                 345                 350

Asn Pro Ala Ser Met Ala Ala Gly Met Thr Pro Ser Gly Met Ser Gly
        355                 360                 365
```

```
Pro Pro Met Gly Met Asn Gln Pro Arg Pro Pro Gly Ile Ser Pro Phe
    370                 375                 380

Gly Thr His Gly Gln Arg Met Pro Gln Gln Thr Tyr Pro Gly Pro Arg
385                 390                 395                 400

Pro Gln Ser Leu Pro Ile Gln Asn Ile Lys Arg Pro Tyr Pro Gly Glu
                405                 410                 415

Pro Asn Tyr Gly Asn Gln Gln Tyr Gly Pro Asn Ser Gln Phe Pro Thr
            420                 425                 430

Gln Pro Gly Gln Tyr Pro Ala Pro Asn Pro Pro Arg Pro Leu Thr Ser
        435                 440                 445

Pro Asn Tyr Pro Gly Gln Arg Met Pro Ser Gln Pro Ser Ser Gly Gln
    450                 455                 460

Tyr Pro Pro Pro Thr Val Asn Met Gly Gln Tyr Tyr Lys Pro Glu Gln
465                 470                 475                 480

Phe Asn Gly Gln Asn Asn Thr Phe Ser Gly Ser Ser Tyr Ser Asn Tyr
                485                 490                 495

Ser Gln Gly Asn Val Asn Arg Pro Pro Arg Pro Val Pro Val Ala Asn
            500                 505                 510

Tyr Pro His Ser Pro Val Pro Gly Asn Pro Thr Pro Pro Met Thr Pro
        515                 520                 525

Gly Ser Ser Ile Pro Pro Tyr Leu Ser Pro Ser Gln Asp Val Lys Pro
    530                 535                 540

Pro Phe Pro Pro Asp Ile Lys Pro Asn Met Ser Ala Leu Pro Pro Pro
545                 550                 555                 560

Pro Ala Asn His Asn Asp Glu Leu Arg Leu Thr Phe Pro Val Arg Asp
                565                 570                 575

Gly Val Val Leu Glu Pro Phe Arg Leu Glu His Asn Leu Ala Val Ser
            580                 585                 590

Asn His Val Phe His Leu Arg Pro Thr Val His Gln Thr Leu Met Trp
        595                 600                 605

Arg Ser Asp Leu Glu Leu Gln Phe Lys Cys Tyr His His Glu Asp Arg
    610                 615                 620

Gln Met Asn Thr Asn Trp Pro Ala Ser Val Gln Val Ser Val Asn Ala
625                 630                 635                 640

Thr Pro Leu Thr Ile Glu Arg Gly Asp Asn Lys Thr Ser His Lys Pro
                645                 650                 655

Leu His Leu Lys His Val Cys Gln Pro Gly Arg Asn Thr Ile Gln Ile
            660                 665                 670

Thr Val Thr Ala Cys Cys Cys Ser His Leu Phe Val Leu Gln Leu Val
        675                 680                 685

His Arg Pro Ser Val Arg Ser Val Leu Gln Gly Leu Leu Lys Lys Arg
    690                 695                 700

Leu Leu Pro Ala Glu His Cys Ile Thr Lys Ile Lys Arg Asn Phe Ser
705                 710                 715                 720

Ser Val Ala Ala Ser Ser Gly Asn Thr Thr Leu Asn Gly Glu Asp Gly
                725                 730                 735

Val Glu Gln Thr Ala Ile Lys Val Ser Leu Lys Cys Pro Ile Thr Phe
            740                 745                 750

Arg Arg Ile Gln Leu Pro Ala Arg Gly His Asp Cys Lys His Val Gln
        755                 760                 765

Cys Phe Asp Leu Glu Ser Tyr Leu Gln Leu Asn Cys Glu Arg Gly Thr
    770                 775                 780

Trp Arg Cys Pro Val Cys Asn Lys Thr Ala Leu Leu Glu Gly Leu Glu
```

```
785                 790                 795                 800

Val Asp Gln Tyr Met Trp Gly Ile Leu Asn Ala Ile Gln His Ser Glu
                805                 810                 815

Phe Glu Glu Val Thr Ile Asp Pro Thr Cys Ser Trp Arg Pro Val Pro
            820                 825                 830

Ile Lys Ser Asp Leu His Ile Lys Asp Asp Pro Asp Gly Ile Pro Ser
        835                 840                 845

Lys Arg Phe Lys Thr Met Ser Pro Ser Gln Met Ile Met Pro Asn Val
    850                 855                 860

Met Glu Met Ile Ala Ala Leu Gly Pro Gly Pro Ser Pro Tyr Pro Leu
865                 870                 875                 880

Pro Pro Pro Pro Gly Gly Thr Asn Ser Asn Asp Tyr Ser Ser Gln Gly
                885                 890                 895

Asn Asn Tyr Gln Gly His Gly Asn Phe Asp Phe Pro His Gly Asn Pro
            900                 905                 910

Gly Gly Thr Ser Met Asn Asp Phe Met His Gly Pro Pro Gln Leu Ser
        915                 920                 925

His Pro Pro Asp Met Pro Asn Asn Met Ala Ala Leu Glu Lys Pro Leu
    930                 935                 940

Ser His Pro Met Gln Glu Thr Leu Leu Pro Glu Leu Thr Asn Pro Asp
945                 950                 955                 960

Glu Leu Leu Ser Tyr Leu Asp Pro Pro Asp Leu Pro Ser Asn Ser Asn
                965                 970                 975

Asp Asp Leu Leu Ser Leu Phe Glu Asn Asn
            980                 985


<210> SEQ ID NO 17
<211> LENGTH: 6892
<212> TYPE: DNA
<213> ORGANISM: Homo sapiens
<220> FEATURE:
<221> NAME/KEY: misc_feature
<222> LOCATION: (1)..(6892)
<223> OTHER INFORMATION: ZMIZ1 X6 transcript

<400> SEQUENCE: 17

cccgcgccgc cgccgccgcc ggggcgcgga gcggggatgc aggcggcgcc cgctgcctgc      60

gcgcagcctt tgttcggcgc tggctgaatc ctacccggag tcgctcgccg cggccgccgc     120

cggccgggcc ccaagccccc gagggcgcca gggcgggatc gcgaccggtg caacttctag     180

ccttgttgtc ctcctggtgc gaagagctcg gccgcctgct gctgctccga catcagaaga     240

gccgccagag cgatccccct gggaaactcc ccatgcagcc ccctctcagc tccatgagct     300

ccatgaaacc cactctgtcg cacagtgatg ggtcgttccc ctatgactct gtcccttggc     360

agcagaacac caaccagcct cccggctccc tttccgtggt caccacggtt tggggagtaa     420

ccaacacatc ccagagccag gtccttggga accctatggc caatgccaac aaccccatga     480

atccaggcgg caaccccatg gcgtcgggca tgaccaccag caacccaggc ctcaactccc     540

cacagtttgc ggggcagcag cagcagttct cagccaaggc tggccccgct cagccctaca     600

tccagcagag catgtatggc cggcccaact accccggcag cgggggcttt ggggccagtt     660

accctggggg tcctaacgcc cccgcaggca tgggcatccc tccgcacacc aggccgcctg     720

ctgacttcac tcagcccgcg gcagccgctg cagcagcggc agtggcagca gcagcagcca     780

cagctacagc cacagccacg gccactgtgg cagccctgca ggagacacag aacaaggata     840

taaaccagta tggaccggtc tgttcctctt tccagatggg tcccacccag gcgtataaca     900
```

```
gccaattcat gaaccagccc gggccgcggg ggcctgcctc catggggggc agcatgaacc    960
ccgcgagcat ggcggctggc atgacgccct cggggatgag cggccctccc atgggcatga   1020
accagccccg gccgcccggc atcagcccct ttggcacaca cgggcagcgg atgccccagc   1080
agacctaccc gggcccccgg ccccagtccc ttcctattca gaacataaag aggccatacc   1140
ctggagagcc caactatgga aaccagcaat atggaccaaa cagccagttc cccacccagc   1200
caggccagta cccagccccc aaccccccga ggccactcac ctcccccaac tacccaggac   1260
agaggatgcc cagccagccg agctccgggc agtacccgcc ccccacggtc aacatggggc   1320
agtattacaa gccagaacag tttaatggac aaaataacac gttctcggga agcagctaca   1380
gtaactacag ccaagggaat gtcaacaggc ctcccaggcc ggttcctgtg gcaaattacc   1440
cccactcacc tgttccaggg aaccccacac cccccatgac ccctgggagc agcatccctc   1500
catacctgtc cccccagccaa gacgtcaaac cacccttccc gcctgacatc aagccaaata   1560
tgagcgctct gccaccaccc ccagccaacc acaatgacga gctgcggctc acattccctg   1620
tgcgggatgg cgtggtgctg gagcccttcc gcctggagca caacctggcg gtcagcaacc   1680
atgtgttcca cctgcggccc acggtccacc agacgctgat gtggaggtct gacctggagc   1740
tgcagttcaa gtgctaccac cacgaggacc ggcagatgaa caccaactgg cccgcctcgg   1800
tgcaggtcag cgtgaacgcc acgcccctca ccattgagcg cggcgacaac aagacctccc   1860
acaagcccct gcacctgaag cacgtgtgcc agccgggccg caacaccatc cagatcaccg   1920
tcacggcctg ctgctgctcc cacctcttcg tgctgcagct ggtacaccgg ccctccgtcc   1980
gctctgtgct gcaaggactc ctcaagaagc gcctcctgcc cgcagagcac tgtatcacga   2040
aaatcaagcg gaatttcagc agcgtggctg cctcctcggg caacacgacc ctcaacgggg   2100
aggatggggt ggagcagacg gccatcaagg tgtctctgaa gtgccccatc acattccggc   2160
gcatccagct gcctgctcga ggacacgatt gcaagcatgt gcagtgcttt gatctggagt   2220
catacctgca gctgaattgc gagagaggga cctggaggtg tcctgtgtgc aataaaaccg   2280
ctctgctgga gggcctggag gtggatcagt acatgtgggg aatcctgaat gccatccaac   2340
actccgagtt tgaagaggtc accatcgatc ccacgtgcag ctggcggccg gtgcccatca   2400
agtcggactt acacatcaag gacgaccctg atggcatccc ctccaagcgg ttcaagacca   2460
tgagtcccag ccagatgatc atgcccaatg tcatggagat gatcgcagcc ctgggccccg   2520
gcccgtcccc ctatcccctc ccgcctcccc caggggggcac caactccaac gactacagca   2580
gccaaggcaa caactaccaa ggccatggca actttgactt cccccacggg aaccctggag   2640
ggacatccat gaatgacttc atgcacgggc ccccccagct ctcccacccc ccggacatgc   2700
ccaacaacat ggccgccctc gagaaacccc tcagccaccc catgcaggaa actatgccac   2760
acgctggcag ctctgaccag ccccacccct ccatacaaca aggtttgcac gtaccacacc   2820
ccagcagcca gtcagggcct ccattacatc acagtggggc tcctcctcct cctccttccc   2880
agcctccccg gcagccgcca caggccgctc ccagcagcca tccacacagc gacctgacct   2940
ttaacccctc ctcagcctta gagggtcagg ccggagcgca gggagcgtcc gacatgccgg   3000
agccttcgct ggatctcctt cccgaactca caaatcctga cgagctcctg tcttatctgg   3060
accccccccga cctgccgagc aatagtaacg atgacctcct gtctctattt gagaacaact   3120
gagggccacc cggtcggggc catccctcca cactctgcat cctaccccac ctacccaaca   3180
cacttttcca cctgggagcc tgtgccctca gaccgccccg caccagagcc acgggctgtg   3240
```

```
gggcggggag ccctccccg ctgcagccct ctcagaacag aggggtaggg agggtgcacc   3300
agtgcaccag gaaggctgtg tgggtctgga gcccacgtcc cacctccaca cccttggctt   3360
gggcccatgc ccagcgcagg cctgaagacc accctcccga gaggaaccag cccggtaaga   3420
gggcacacgc tgatgcggct tcccggtccc tccgcgtgtg ccgattccag atgaccttcc   3480
agtgtcccca aggttcttcc atcttctaga ctgtaaccct gcctccctgc ttcctggtcc   3540
agagcctccc tccagtgact gtggagcctg agaaggcccc cgggccccag catgggcccc   3600
gagccttgga ggagcactgg cagttggtgg cagtgagacc agcccaccca ccaccaccca   3660
ccacagaaaa gcacaaacct ctgggaaaga caacgtctct cgggggccag ggtcatcgg   3720
tttgacccct gacctataag ccaagatacc ccataaacac actcagaaag cagagaaaaa   3780
ggacaagagt ctgtgtttga gagggggtct gccattcctg cttggggact ggtggggaag   3840
agggccagga catcttctga gccaggacgt ccctgaggct ccacctccaa gctcagacag   3900
ggcccaggct tggggaacag agagagcagg tgtacaccca accaaagtga ttgtgccctt   3960
ggttgggggg cgcgggcata taacctgtca gaagcaaaca ggagcggcaa cttctaactt   4020
tgctccaagc cactctcttt ttaaacagca acaatttaaa gctatgaagt cacctggaga   4080
aaaggaacgt tgctcttgga cagcaagcaa accatttctc tccgtctgtt ctgtttttct   4140
cctagtccct ctcctgccac ctctccaaga cttccgtggg acacccactt ccctctgtcc   4200
tagttctctt tgtccaatca gatggcaagg gcagtgcgtg gaaaggccgg ggaggtgcag   4260
aaaccagagc ccagggcaat ggtgtctgtc cagcccctcc ctctgtccct gtgctccaag   4320
ctgcccccgg ctgcagccca ggccatggac atgtgcacca gtatgtacct gcaggcatgg   4380
gggggagggg ggcgtgtttc tgggcctgcc ccagacactg cccttggctg ccagcctacc   4440
ctgcctgcac tcctccacca tcacaatctc acccaaactc ctgctcactc aagcaaaagc   4500
agcctctggc cttccctcca ccgctttgct ccatctggct taccactctc cagggcctcc   4560
tggggagcct gtcctgtgtt cactttgttt caggctggtc tgtgccccgt gagccacatg   4620
gcctagggtg atgccaggtt gtcccgtcac tggggtccca tctgtaaatt ctttgcgccc   4680
ttcccggctg ctgcctgggg ccctttcctg ctctcccgtc cgctgtgggt ggtccccagc   4740
tctcctctgt gggttttacc ggaaaggtgg ccccagctgt tgacttccag tcactgtccc   4800
agacggcaca aggttttctg taggaaagct gccattgccc cggccccttt tcttcctttg   4860
tcccgttgtc gaggtttttt caaatagcgt gttgttcagt atgcaaatca attattttaa   4920
gaatcgcttt tgtaaatatc tttgtgaata ttttagtatc gtctttgata atattcaaca   4980
ttttcatgac ctggttatag cctttgctgg tgtttttaaa atacctggac tcaatgacaa   5040
agaccgagtc ttcttttttt ttaaacaaaa acaaaaaaag caaccagggc tatttgtaca   5100
gttgaagggg tgaacagaat gggcggctgt gctgggagtt ggaagaccgg gcagcccgct   5160
atttagagcc atccctcagt cagctggcag ggacaagcca acgccaggta gcatgtggcc   5220
acccttgccc agtgtctgtg gcctggcaag tggccacgcc ctgtgtcaga ccatctggga   5280
attaagctcc agacagactt acagatgcct tccttaggag ttcttgcttc ttgcgttgat   5340
actttgcccc agaaaggcct gggattcatt ctggttctta tcagggtgtg tccacactct   5400
gctcacaggt ggatccacgg ctttccagtg cggagagtcg agatgctccc tgcagcccag   5460
gccccgggca cctcctgcaa ccatctctgg gctcagcacc tgaggcgggt ttcctgggtc   5520
ccctctccag caagcctcca ccagcaagct cggcccagag cttcccttcc ggctggctct   5580
gaaccgtgcg tggtgcctac agcctgcagt ctggagacaa gctcttccgg agtgctctgg   5640
```

```
gagccaggcc agggtgtgag ggaggtgcag aggcatccgg ggcgggagca agccccaggt   5700

tgtgacaggt gcaggtagac aacgcccata aacagagatg gtcctgaact ctggagagat   5760

ccttccctga tcctttcgga cgactacttg gagccataag taacctcagc aaaaacgagg   5820

cctctgcaag ccacttttcc atgccaagca tccacccggc ccacaggcat gtttctgccg   5880

ccactccgca agatggacag ggagccagca ggcaggcggg aagggccaag tacaggcaat   5940

cacccccatc ttcttggttt gaagctttat ccatgtatca tgttccgtgt agccatttta   6000

ttttttaaga aactgctaat actttctccc taatggaagc cctgatcccc cagagagcta   6060

caggtctgct cccgacgggc ctcgggcctg acccgtccac acagggccgt gtcaacagca   6120

gcgactcaag ggacgtgtgt acatatgtaa atgagaaata gagacgtgtc aacagatgca   6180

ttcatttctc ttggaatgtg tattgttttt attttgcgaa acaaaacaaa acaaaaaaaa   6240

aagcttggaa ctccatcacg tggaaaaact agatcctgtt ggttatagca tttgtgagtt   6300

ctccacgtct gtctctctcg ctcatgtaat atactctgac cctgagtgga aaggggtttt   6360

tgttctgttt ttattttacc tacatgtact atttagcttc agtgtactag tcctgccacc   6420

tgtgtatttt tagggtgcta tggaaataat gaaaagaaac ggggatttca gaagaaaatt   6480

gtaaccaaat tcatactttg tataattttt gatatcatga tcacaggtga ttcacacgta   6540

cacacataaa cacacccacc agtgcagcct gaagtaactc ccacagaaac catcatcgtc   6600

tttgtacatc gtatgtacaa tgcaatcatt tcatacttta aactggtcaa aaaactaatt   6660

gtgatttcta gtcttgcaaa gctgtatgta gttagatgat gtgacaacct ctaatattta   6720

tctaataaat atgtattcag atgaaacctg tatattaggt gttcatgtgg ttattttgta   6780

tttaaagatc aaattatttg actattgcta gacatttcta tactctgttg taacactgag   6840

gtatctcatt tgcccatgtt aattttttttc taaataaatt gacaaaaaca aa           6892
```

```
<210> SEQ ID NO 18
<211> LENGTH: 949
<212> TYPE: PRT
<213> ORGANISM: Homo sapiens
<220> FEATURE:
<221> NAME/KEY: MISC_FEATURE
<222> LOCATION: (1)..(949)
<223> OTHER INFORMATION: ZMIZ1 X6 amino acid sequence

<400> SEQUENCE: 18

Met Gln Pro Pro Leu Ser Ser Met Ser Ser Met Lys Pro Thr Leu Ser
1               5                   10                  15

His Ser Asp Gly Ser Phe Pro Tyr Asp Ser Val Pro Trp Gln Gln Asn
            20                  25                  30

Thr Asn Gln Pro Pro Gly Ser Leu Ser Val Val Thr Thr Val Trp Gly
        35                  40                  45

Val Thr Asn Thr Ser Gln Ser Gln Val Leu Gly Asn Pro Met Ala Asn
    50                  55                  60

Ala Asn Asn Pro Met Asn Pro Gly Gly Asn Pro Met Ala Ser Gly Met
65                  70                  75                  80

Thr Thr Ser Asn Pro Gly Leu Asn Ser Pro Gln Phe Ala Gly Gln Gln
                85                  90                  95

Gln Gln Phe Ser Ala Lys Ala Gly Pro Ala Gln Pro Tyr Ile Gln Gln
            100                 105                 110

Ser Met Tyr Gly Arg Pro Asn Tyr Pro Gly Ser Gly Gly Phe Gly Ala
        115                 120                 125
```

```
Ser Tyr Pro Gly Gly Pro Asn Ala Pro Ala Gly Met Gly Ile Pro Pro
    130                 135                 140

His Thr Arg Pro Pro Ala Asp Phe Thr Gln Pro Ala Ala Ala Ala Ala
145                 150                 155                 160

Ala Ala Ala Val Ala Ala Ala Ala Ala Thr Ala Thr Ala Thr Ala Thr
                165                 170                 175

Ala Thr Val Ala Ala Leu Gln Glu Thr Gln Asn Lys Asp Ile Asn Gln
            180                 185                 190

Tyr Gly Pro Val Cys Ser Ser Phe Gln Met Gly Pro Thr Gln Ala Tyr
        195                 200                 205

Asn Ser Gln Phe Met Asn Gln Pro Gly Pro Arg Gly Pro Ala Ser Met
    210                 215                 220

Gly Gly Ser Met Asn Pro Ala Ser Met Ala Ala Gly Met Thr Pro Ser
225                 230                 235                 240

Gly Met Ser Gly Pro Pro Met Gly Met Asn Gln Pro Arg Pro Pro Gly
                245                 250                 255

Ile Ser Pro Phe Gly Thr His Gly Gln Arg Met Pro Gln Gln Thr Tyr
            260                 265                 270

Pro Gly Pro Arg Pro Gln Ser Leu Pro Ile Gln Asn Ile Lys Arg Pro
        275                 280                 285

Tyr Pro Gly Glu Pro Asn Tyr Gly Asn Gln Gln Tyr Gly Pro Asn Ser
    290                 295                 300

Gln Phe Pro Thr Gln Pro Gly Gln Tyr Pro Ala Pro Asn Pro Pro Arg
305                 310                 315                 320

Pro Leu Thr Ser Pro Asn Tyr Pro Gly Gln Arg Met Pro Ser Gln Pro
                325                 330                 335

Ser Ser Gly Gln Tyr Pro Pro Pro Thr Val Asn Met Gly Gln Tyr Tyr
            340                 345                 350

Lys Pro Glu Gln Phe Asn Gly Gln Asn Asn Thr Phe Ser Gly Ser Ser
        355                 360                 365

Tyr Ser Asn Tyr Ser Gln Gly Asn Val Asn Arg Pro Pro Arg Pro Val
    370                 375                 380

Pro Val Ala Asn Tyr Pro His Ser Pro Val Pro Gly Asn Pro Thr Pro
385                 390                 395                 400

Pro Met Thr Pro Gly Ser Ser Ile Pro Pro Tyr Leu Ser Pro Ser Gln
                405                 410                 415

Asp Val Lys Pro Pro Phe Pro Pro Asp Ile Lys Pro Asn Met Ser Ala
            420                 425                 430

Leu Pro Pro Pro Pro Ala Asn His Asn Asp Glu Leu Arg Leu Thr Phe
        435                 440                 445

Pro Val Arg Asp Gly Val Val Leu Glu Pro Phe Arg Leu Glu His Asn
    450                 455                 460

Leu Ala Val Ser Asn His Val Phe His Leu Arg Pro Thr Val His Gln
465                 470                 475                 480

Thr Leu Met Trp Arg Ser Asp Leu Glu Leu Gln Phe Lys Cys Tyr His
                485                 490                 495

His Glu Asp Arg Gln Met Asn Thr Asn Trp Pro Ala Ser Val Gln Val
            500                 505                 510

Ser Val Asn Ala Thr Pro Leu Thr Ile Glu Arg Gly Asp Asn Lys Thr
        515                 520                 525

Ser His Lys Pro Leu His Leu Lys His Val Cys Gln Pro Gly Arg Asn
    530                 535                 540

Thr Ile Gln Ile Thr Val Thr Ala Cys Cys Cys Ser His Leu Phe Val
```

```
545                 550                 555                 560

Leu Gln Leu Val His Arg Pro Ser Val Arg Ser Val Leu Gln Gly Leu
                565                 570                 575

Leu Lys Lys Arg Leu Leu Pro Ala Glu His Cys Ile Thr Lys Ile Lys
            580                 585                 590

Arg Asn Phe Ser Ser Val Ala Ala Ser Ser Gly Asn Thr Thr Leu Asn
        595                 600                 605

Gly Glu Asp Gly Val Glu Gln Thr Ala Ile Lys Val Ser Leu Lys Cys
    610                 615                 620

Pro Ile Thr Phe Arg Arg Ile Gln Leu Pro Ala Arg Gly His Asp Cys
625                 630                 635                 640

Lys His Val Gln Cys Phe Asp Leu Glu Ser Tyr Leu Gln Leu Asn Cys
                645                 650                 655

Glu Arg Gly Thr Trp Arg Cys Pro Val Cys Asn Lys Thr Ala Leu Leu
            660                 665                 670

Glu Gly Leu Glu Val Asp Gln Tyr Met Trp Gly Ile Leu Asn Ala Ile
        675                 680                 685

Gln His Ser Glu Phe Glu Glu Val Thr Ile Asp Pro Thr Cys Ser Trp
    690                 695                 700

Arg Pro Val Pro Ile Lys Ser Asp Leu His Ile Lys Asp Asp Pro Asp
705                 710                 715                 720

Gly Ile Pro Ser Lys Arg Phe Lys Thr Met Ser Pro Ser Gln Met Ile
                725                 730                 735

Met Pro Asn Val Met Glu Met Ile Ala Ala Leu Gly Pro Gly Pro Ser
            740                 745                 750

Pro Tyr Pro Leu Pro Pro Pro Pro Gly Gly Thr Asn Ser Asn Asp Tyr
        755                 760                 765

Ser Ser Gln Gly Asn Asn Tyr Gln Gly His Gly Asn Phe Asp Phe Pro
    770                 775                 780

His Gly Asn Pro Gly Gly Thr Ser Met Asn Asp Phe Met His Gly Pro
785                 790                 795                 800

Pro Gln Leu Ser His Pro Pro Asp Met Pro Asn Asn Met Ala Ala Leu
                805                 810                 815

Glu Lys Pro Leu Ser His Pro Met Gln Glu Thr Met Pro His Ala Gly
            820                 825                 830

Ser Ser Asp Gln Pro His Pro Ser Ile Gln Gln Gly Leu His Val Pro
        835                 840                 845

His Pro Ser Ser Gln Ser Gly Pro Pro Leu His His Ser Gly Ala Pro
    850                 855                 860

Pro Pro Pro Pro Ser Gln Pro Pro Arg Gln Pro Pro Gln Ala Ala Pro
865                 870                 875                 880

Ser Ser His Pro His Ser Asp Leu Thr Phe Asn Pro Ser Ser Ala Leu
                885                 890                 895

Glu Gly Gln Ala Gly Ala Gln Gly Ala Ser Asp Met Pro Glu Pro Ser
            900                 905                 910

Leu Asp Leu Leu Pro Glu Leu Thr Asn Pro Asp Glu Leu Leu Ser Tyr
        915                 920                 925

Leu Asp Pro Pro Asp Leu Pro Ser Asn Ser Asn Asp Asp Leu Leu Ser
    930                 935                 940

Leu Phe Glu Asn Asn
945
```

<210> SEQ ID NO 19

<211> LENGTH: 7004
<212> TYPE: DNA
<213> ORGANISM: Homo sapiens
<220> FEATURE:
<221> NAME/KEY: misc_feature
<222> LOCATION: (1)..(7004)
<223> OTHER INFORMATION: ZMIZ1 X7 transcript

<400> SEQUENCE: 19

```
gtcatccacc gccagcgcct tcccggcggc ctcctcgggc gacagcgctc cgggagcccc     60

actcgcacaa gtgttgcttc caattaattg cctgggcggg ggaaggaaag gggcctcgtc    120

gccgcccccg cccggaggct ggagtgctgc tcgtcgggtc gtgcgttcgc tcggcagcgg    180

cgtgcaccag caccacccct gcgtgcaagt ttgaaatgtg agctgcctcc gattcatact    240

cgctcgcgct ccctcgcagc gaagtggctg ggctgacggt ctgcgcgcgc gaccttgttg    300

tcctcctggt gcgaagagct cggccgcctg ctgctgctcc gacatcagaa gagccgccag    360

agcgatcccc ctgggaaact ccccatgcag ccccctctca gctccatgag ctccatgaaa    420

cccactctgt cgcacagtga tgggtcgttc ccctatgact ctgtcccttg gcagcagaac    480

accaaccagc ctcccggctc cctttccgtg gtcaccacgg tttggggagt aaccaacaca    540

tcccagagcc aggtccttgg gaaccctatg gccaatgcca acaaccccat gaatccaggc    600

ggcaacccca tggcgtcggg catgaccacc agcaacccag gcctcaactc cccacagttt    660

gcggggcagc agcagcagtt ctcagccaag gctggccccg ctcagcccta catccagcag    720

agcatgtatg gccggcccaa ctaccccggc agcgggggct ttggggccag ttaccctggg    780

ggtcctaacg cccccgcagg catgggcatc cctccgcaca ccaggccgcc tgctgacttc    840

actcagcccg cggcagccgc tgcagcagcg gcagtggcag cagcagcagc cacagctaca    900

gccacagcca cggccactgt ggcagccctg caggagacac agaacaagga tataaaccag    960

tatggaccgg tctgttcctc tttccagatg ggtcccaccc aggcgtataa cagccaattc   1020

atgaaccagc ccgggccgcg gggggcctgcc tccatggggg gcagcatgaa ccccgcgagc   1080

atggcggctg gcatgacgcc ctcggggatg agcggccctc ccatgggcat gaaccagccc   1140

cggccgcccg gcatcagccc ctttggcaca cacgggcagc ggatgcccca gcagacctac   1200

ccgggccccc ggccccagtc ccttcctatt cagaacataa agaggcccta ccctggagag   1260

cccaactatg gaaaccagca atatggacca aacagccagt tccccaccca gccaggccag   1320

tacccagccc ccaacccccc gaggccactc acctccccca actacccagg acagaggatg   1380

cccagccagc cgagctccgg gcagtacccg ccccccacgg tcaacatggg gcagtattac   1440

aagccagaac agtttaatgg acaaaataac acgttctcgg gaagcagcta cagtaactac   1500

agccaaggga atgtcaacag gcctcccagg ccggttcctg tggcaaatta cccccactca   1560

cctgttccag ggaaccccac accccccatg acccctggga gcagcatccc tccatacctg   1620

tcccccagcc aagacgtcaa accacccttc ccgcctgaca tcaagccaaa tatgagcgct   1680

ctgccaccac ccccagccaa ccacaatgac gagctgcggc tcacattccc tgtgcgggat   1740

ggcgtggtgc tggagccctt ccgcctggag cacaacctgg cggtcagcaa ccatgtgttc   1800

cacctgcggc ccacggtcca ccagacgctg atgtggaggt ctgacctgga gctgcagttc   1860

aagtgctacc accacgagga ccggcagatg aacaccaact ggcccgcctc ggtgcaggtc   1920

agcgtgaacg ccacgcccct caccattgag cgcggcgaca acaagacctc ccacaagccc   1980

ctgcacctga agcacgtgtg ccagccgggc cgcaacacca tccagatcac cgtcacggcc   2040

tgctgctgct cccacctctt cgtgctgcag ctggtacacc ggccctccgt ccgctctgtg   2100
```

```
ctgcaaggac tcctcaagaa gcgcctcctg cccgcagagc actgtatcac gaaaatcaag   2160
cggaatttca gcagcgtggc tgcctcctcg ggcaacacga ccctcaacgg ggaggatggg   2220
gtggagcaga cggccatcaa ggtgtctctg aagtgcccca tcacattccg gcgcatccag   2280
ctgcctgctc gaggacacga ttgcaagcat gtgcagtgct ttgatctgga gtcatacctg   2340
cagctgaatt gcgagagagg gacctggagg tgtcctgtgt gcaataaaac cgctctgctg   2400
gagggcctgg aggtggatca gtacatgtgg ggaatcctga atgccatcca acactccgag   2460
tttgaagagg tcaccatcga tcccacgtgc agctggcggc cggtgcccat caagtcggac   2520
ttacacatca aggacgaccc tgatggcatc ccctccaagc ggttcaagac catgagtccc   2580
agccagatga tcatgcccaa tgtcatggag atgatcgcag ccctgggccc cggcccgtcc   2640
ccctatcccc tcccgcctcc cccagggggc accaactcca acgactacag cagccaaggc   2700
aacaactacc aaggccatgg caactttgac ttcccccacg ggaaccctgg agggacatcc   2760
atgaatgact tcatgcacgg gccccccccag ctctcccacc ccccggacat gcccaacaac   2820
atggccgccc tcgagaaacc cctcagccac cccatgcagg aaactatgcc acacgctggc   2880
agctctgacc agccccaccc ctccatacaa caaggtttgc acgtaccaca ccccagcagc   2940
cagtcagggc ctccattaca tcacagtggg gctcctcctc ctcctccttc ccagcctccc   3000
cggcagccgc cacaggccgc tcccagcagc catccacaca gcgacctgac ctttaacccc   3060
tcctcagcct tagagggtca ggccggagcg cagggagcgt ccgacatgcc ggagccttcg   3120
ctggatctcc ttcccgaact cacaaatcct gacgagctcc tgtcttatct ggaccccccc   3180
gacctgccga gcaatagtaa cgatgacctc ctgtctctat ttgagaacaa ctgagggcca   3240
cccggtcggg gccatccctc cacactctgc atcctacccc acctacccaa cacacttttc   3300
cacctgggag cctgtgccct cagaccgccc cgcaccagag ccacgggctg tggggcgggg   3360
agccctcccc cgctgcagcc ctctcagaac agaggggtag ggagggtgca ccagtgcacc   3420
aggaaggctg tgtgggtctg gagcccacgt cccacctcca caccccttggc ttgggcccat   3480
gcccagcgca ggcctgaaga ccaccctccc gagaggaacc agcccggtaa gagggcacac   3540
gctgatgcgg cttcccggtc cctccgcgtg tgccgattcc agatgacctt ccagtgtccc   3600
caaggttctt ccatcttcta gactgtaacc ctgcctccct gcttcctggt ccagagcctc   3660
cctccagtga ctgtggagcc tgagaaggcc cccgggcccc agcatgggcc ccgagccttg   3720
gaggagcact ggcagttggt ggcagtgaga ccagcccacc caccaccacc caccacagaa   3780
aagcacaaac ctctgggaaa gacaacgtct ctcgggggcc aggggtcatc ggtttgaccc   3840
ctgacctata agccaagata ccccataaac acactcagaa agcagagaaa aaggacaaga   3900
gtctgtgttt gagaggggggt ctgccattcc tgcttgggga ctggtgggga agagggccag   3960
gacatcttct gagccaggac gtccctgagg ctccacctcc aagctcagac agggcccagg   4020
cttggggaac agagagagca ggtgtacacc caaccaaagt gattgtgccc ttggttgggg   4080
ggcgcgggca tataacctgt cagaagcaaa caggagcggc aacttctaac tttgctccaa   4140
gccactctct ttttaaacag caacaattta aagctatgaa gtcacctgga gaaaaggaac   4200
gttgctcttg gacagcaagc aaaccatttc tctccgtctg ttctgttttt ctcctagtcc   4260
ctctcctgcc acctctccaa gacttccgtg ggacacccac ttccctctgt cctagttctc   4320
tttgtccaat cagatggcaa gggcagtgcg tggaaaggcc ggggaggtgc agaaaccaga   4380
gcccagggca atggtgtctg tccagcccct ccctctgtcc ctgtgctcca agctgccccc   4440
```

```
ggctgcagcc caggccatgg acatgtgcac cagtatgtac ctgcaggcat ggggggggagg   4500
ggggcgtgtt tctgggcctg ccccagacac tgcccttggc tgccagccta ccctgcctgc   4560
actcctccac catcacaatc tcacccaaac tcctgctcac tcaagcaaaa gcagcctctg   4620
gccttccctc caccgctttg ctccatctgg cttaccactc tccagggcct cctggggagc   4680
ctgtcctgtg ttcactttgt ttcaggctgg tctgtgcccc gtgagccaca tggcctaggg   4740
tgatgccagg ttgtcccgtc actggggtcc catctgtaaa ttctttgcgc ccttcccggc   4800
tgctgcctgg ggccctttcc tgctctcccg tccgctgtgg gtggtcccca gctctcctct   4860
gtgggtttta ccggaaaggt ggccccagct gttgacttcc agtcactgtc ccagacggca   4920
caaggttttc tgtaggaaag ctgccattgc cccggcccct tttcttcctt tgtcccgttg   4980
tcgaggtttt ttcaaatagc gtgttgttca gtatgcaaat caattatttt aagaatcgct   5040
tttgtaaata tctttgtgaa tattttagta tcgtctttga taatattcaa cattttcatg   5100
acctggttat agcctttgct ggtgttttta aaatacctgg actcaatgac aaagaccgag   5160
tcttcttttt ttttaaacaa aaacaaaaaa agcaaccagg gctatttgta cagttgaagg   5220
ggtgaacaga atgggcggct gtgctgggag ttggaagacc gggcagcccg ctatttagag   5280
ccatccctca gtcagctggc agggacaagc caacgccagg tagcatgtgg ccacccttgc   5340
ccagtgtctg tggcctggca agtggccacg ccctgtgtca gaccatctgg gaattaagct   5400
ccagacagac ttacagatgc cttccttagg agttcttgct tcttgcgttg atactttgcc   5460
ccagaaaggc ctgggattca ttctggttct tatcagggtg tgtccacact ctgctcacag   5520
gtggatccac ggctttccag tgcggagagt cgagatgctc cctgcagccc aggccccggg   5580
cacctcctgc aaccatctct gggctcagca cctgaggcgg gtttcctggg tcccctctcc   5640
agcaagcctc caccagcaag ctcggcccag agcttccctt ccggctggct ctgaaccgtg   5700
cgtggtgcct acagcctgca gtctggagac aagctcttcc ggagtgctct gggagccagg   5760
ccagggtgtg agggaggtgc agaggcatcc ggggcgggag caagccccag gttgtgacag   5820
gtgcaggtag acaacgccca taaacagaga tggtcctgaa ctctggagag atccttccct   5880
gatcctttcg gacgactact tggagccata agtaacctca gcaaaaacga ggcctctgca   5940
agccactttt ccatgccaag catccacccg gcccacaggc atgtttctgc cgccactccg   6000
caagatggac agggagccag caggcaggcg ggaagggcca agtacaggca atcaccccca   6060
tcttcttggt ttgaagcttt atccatgtat catgttccgt gtagccattt tatttttttaa   6120
gaaactgcta atactttctc cctaatggaa gccctgatcc cccagagagc tacaggtctg   6180
ctcccgacgg gcctcgggcc tgacccgtcc acacagggcc gtgtcaacag cagcgactca   6240
agggacgtgt gtacatatgt aaatgagaaa tagagacgtg tcaacagatg cattcatttc   6300
tcttggaatg tgtattgttt ttattttgcg aaacaaaaca aaacaaaaaa aaaagcttgg   6360
aactccatca cgtggaaaaa ctagatcctg ttggttatag catttgtgag ttctccacgt   6420
ctgtctctct cgctcatgta atatactctg accctgagtg gaaaggggtt tttgttctgt   6480
ttttatttta cctacatgta ctatttagct tcagtgtact agtcctgcca cctgtgtatt   6540
tttagggtgc tatggaaata atgaaaagaa acggggattt cagaagaaaa ttgtaaccaa   6600
attcatactt tgtataattt ttgatatcat gatcacaggt gattcacacg tacacacata   6660
aacacaccca ccagtgcagc ctgaagtaac tcccacagaa accatcatcg tctttgtaca   6720
tcgtatgtac aatgcaatca tttcatactt taaactggtc aaaaaactaa ttgtgatttc   6780
tagtcttgca aagctgtatg tagttagatg atgtgacaac ctctaatatt tatctaataa   6840
```

```
atatgtattc agatgaaacc tgtatattag gtgttcatgt ggttattttg tatttaaaga   6900

tcaaattatt tgactattgc tagacatttc tatactctgt tgtaacactg aggtatctca   6960

tttgcccatg ttaatttttt tctaaataaa ttgacaaaaa caaa                     7004


<210> SEQ ID NO 20
<211> LENGTH: 949
<212> TYPE: PRT
<213> ORGANISM: Homo sapiens
<220> FEATURE:
<221> NAME/KEY: MISC_FEATURE
<222> LOCATION: (1)..(949)
<223> OTHER INFORMATION: ZMIZ1 X7 amino acid sequence

<400> SEQUENCE: 20

Met Gln Pro Pro Leu Ser Ser Met Ser Ser Met Lys Pro Thr Leu Ser
1               5                   10                  15

His Ser Asp Gly Ser Phe Pro Tyr Asp Ser Val Pro Trp Gln Gln Asn
            20                  25                  30

Thr Asn Gln Pro Pro Gly Ser Leu Ser Val Val Thr Thr Val Trp Gly
        35                  40                  45

Val Thr Asn Thr Ser Gln Ser Gln Val Leu Gly Asn Pro Met Ala Asn
    50                  55                  60

Ala Asn Asn Pro Met Asn Pro Gly Gly Asn Pro Met Ala Ser Gly Met
65                  70                  75                  80

Thr Thr Ser Asn Pro Gly Leu Asn Ser Pro Gln Phe Ala Gly Gln Gln
                85                  90                  95

Gln Gln Phe Ser Ala Lys Ala Gly Pro Ala Gln Pro Tyr Ile Gln Gln
            100                 105                 110

Ser Met Tyr Gly Arg Pro Asn Tyr Pro Gly Ser Gly Gly Phe Gly Ala
        115                 120                 125

Ser Tyr Pro Gly Gly Pro Asn Ala Pro Ala Gly Met Gly Ile Pro Pro
    130                 135                 140

His Thr Arg Pro Pro Ala Asp Phe Thr Gln Pro Ala Ala Ala Ala Ala
145                 150                 155                 160

Ala Ala Ala Val Ala Ala Ala Ala Ala Thr Ala Thr Ala Thr Ala Thr
                165                 170                 175

Ala Thr Val Ala Ala Leu Gln Glu Thr Gln Asn Lys Asp Ile Asn Gln
            180                 185                 190

Tyr Gly Pro Val Cys Ser Ser Phe Gln Met Gly Pro Thr Gln Ala Tyr
        195                 200                 205

Asn Ser Gln Phe Met Asn Gln Pro Gly Pro Arg Gly Pro Ala Ser Met
    210                 215                 220

Gly Gly Ser Met Asn Pro Ala Ser Met Ala Ala Gly Met Thr Pro Ser
225                 230                 235                 240

Gly Met Ser Gly Pro Pro Met Gly Met Asn Gln Pro Arg Pro Pro Gly
                245                 250                 255

Ile Ser Pro Phe Gly Thr His Gly Gln Arg Met Pro Gln Gln Thr Tyr
            260                 265                 270

Pro Gly Pro Arg Pro Gln Ser Leu Pro Ile Gln Asn Ile Lys Arg Pro
        275                 280                 285

Tyr Pro Gly Glu Pro Asn Tyr Gly Asn Gln Gln Tyr Gly Pro Asn Ser
    290                 295                 300

Gln Phe Pro Thr Gln Pro Gly Gln Tyr Pro Ala Pro Asn Pro Pro Arg
305                 310                 315                 320
```

```
Pro Leu Thr Ser Pro Asn Tyr Pro Gly Gln Arg Met Pro Ser Gln Pro
                325                 330                 335

Ser Ser Gly Gln Tyr Pro Pro Pro Thr Val Asn Met Gly Gln Tyr Tyr
            340                 345                 350

Lys Pro Glu Gln Phe Asn Gly Gln Asn Asn Thr Phe Ser Gly Ser Ser
        355                 360                 365

Tyr Ser Asn Tyr Ser Gln Gly Asn Val Asn Arg Pro Pro Arg Pro Val
    370                 375                 380

Pro Val Ala Asn Tyr Pro His Ser Pro Val Pro Gly Asn Pro Thr Pro
385                 390                 395                 400

Pro Met Thr Pro Gly Ser Ser Ile Pro Pro Tyr Leu Ser Pro Ser Gln
                405                 410                 415

Asp Val Lys Pro Pro Phe Pro Pro Asp Ile Lys Pro Asn Met Ser Ala
            420                 425                 430

Leu Pro Pro Pro Pro Ala Asn His Asn Asp Glu Leu Arg Leu Thr Phe
        435                 440                 445

Pro Val Arg Asp Gly Val Val Leu Glu Pro Phe Arg Leu Glu His Asn
    450                 455                 460

Leu Ala Val Ser Asn His Val Phe His Leu Arg Pro Thr Val His Gln
465                 470                 475                 480

Thr Leu Met Trp Arg Ser Asp Leu Glu Leu Gln Phe Lys Cys Tyr His
                485                 490                 495

His Glu Asp Arg Gln Met Asn Thr Asn Trp Pro Ala Ser Val Gln Val
            500                 505                 510

Ser Val Asn Ala Thr Pro Leu Thr Ile Glu Arg Gly Asp Asn Lys Thr
        515                 520                 525

Ser His Lys Pro Leu His Leu Lys His Val Cys Gln Pro Gly Arg Asn
    530                 535                 540

Thr Ile Gln Ile Thr Val Thr Ala Cys Cys Cys Ser His Leu Phe Val
545                 550                 555                 560

Leu Gln Leu Val His Arg Pro Ser Val Arg Ser Val Leu Gln Gly Leu
                565                 570                 575

Leu Lys Lys Arg Leu Leu Pro Ala Glu His Cys Ile Thr Lys Ile Lys
            580                 585                 590

Arg Asn Phe Ser Ser Val Ala Ala Ser Ser Gly Asn Thr Thr Leu Asn
        595                 600                 605

Gly Glu Asp Gly Val Glu Gln Thr Ala Ile Lys Val Ser Leu Lys Cys
    610                 615                 620

Pro Ile Thr Phe Arg Arg Ile Gln Leu Pro Ala Arg Gly His Asp Cys
625                 630                 635                 640

Lys His Val Gln Cys Phe Asp Leu Glu Ser Tyr Leu Gln Leu Asn Cys
                645                 650                 655

Glu Arg Gly Thr Trp Arg Cys Pro Val Cys Asn Lys Thr Ala Leu Leu
            660                 665                 670

Glu Gly Leu Glu Val Asp Gln Tyr Met Trp Gly Ile Leu Asn Ala Ile
        675                 680                 685

Gln His Ser Glu Phe Glu Glu Val Thr Ile Asp Pro Thr Cys Ser Trp
    690                 695                 700

Arg Pro Val Pro Ile Lys Ser Asp Leu His Ile Lys Asp Asp Pro Asp
705                 710                 715                 720

Gly Ile Pro Ser Lys Arg Phe Lys Thr Met Ser Pro Ser Gln Met Ile
                725                 730                 735

Met Pro Asn Val Met Glu Met Ile Ala Ala Leu Gly Pro Gly Pro Ser
```

```
            740                 745                 750

Pro Tyr Pro Leu Pro Pro Pro Pro Gly Gly Thr Asn Ser Asn Asp Tyr
        755                 760                 765

Ser Ser Gln Gly Asn Asn Tyr Gln Gly His Gly Asn Phe Asp Phe Pro
    770                 775                 780

His Gly Asn Pro Gly Gly Thr Ser Met Asn Asp Phe Met His Gly Pro
785                 790                 795                 800

Pro Gln Leu Ser His Pro Pro Asp Met Pro Asn Asn Met Ala Ala Leu
                805                 810                 815

Glu Lys Pro Leu Ser His Pro Met Gln Glu Thr Met Pro His Ala Gly
            820                 825                 830

Ser Ser Asp Gln Pro His Pro Ser Ile Gln Gln Gly Leu His Val Pro
        835                 840                 845

His Pro Ser Ser Gln Ser Gly Pro Pro Leu His His Ser Gly Ala Pro
    850                 855                 860

Pro Pro Pro Pro Ser Gln Pro Pro Arg Gln Pro Pro Gln Ala Ala Pro
865                 870                 875                 880

Ser Ser His Pro His Ser Asp Leu Thr Phe Asn Pro Ser Ser Ala Leu
                885                 890                 895

Glu Gly Gln Ala Gly Ala Gln Gly Ala Ser Asp Met Pro Glu Pro Ser
            900                 905                 910

Leu Asp Leu Leu Pro Glu Leu Thr Asn Pro Asp Glu Leu Leu Ser Tyr
        915                 920                 925

Leu Asp Pro Pro Asp Leu Pro Ser Asn Ser Asn Asp Asp Leu Leu Ser
    930                 935                 940

Leu Phe Glu Asn Asn
945
```

<210> SEQ ID NO 21
<211> LENGTH: 26
<212> TYPE: DNA
<213> ORGANISM: Artificial Sequence
<220> FEATURE:
<223> OTHER INFORMATION: ZMIZ1 alternative promoter primer

<400> SEQUENCE: 21
tatttagggt tagggaagta agatgt 26

<210> SEQ ID NO 22
<211> LENGTH: 25
<212> TYPE: DNA
<213> ORGANISM: Artificial Sequence
<220> FEATURE:
<223> OTHER INFORMATION: ZMIZ1 alternative promoter primer

<400> SEQUENCE: 22
aaactaaaca tccaaattaa atctc 25

<210> SEQ ID NO 23
<211> LENGTH: 25
<212> TYPE: RNA
<213> ORGANISM: Artificial Sequence
<220> FEATURE:
<223> OTHER INFORMATION: stealth_56 sense

<400> SEQUENCE: 23
ccggugcaac uucuagccuu guugu 25

<210> SEQ ID NO 24

```
<211> LENGTH: 25
<212> TYPE: RNA
<213> ORGANISM: Artificial Sequence
<220> FEATURE:
<223> OTHER INFORMATION: stealth_56 anti-sense

<400> SEQUENCE: 24

acaacaaggc uagaaguugc accgg                                          25


<210> SEQ ID NO 25
<211> LENGTH: 25
<212> TYPE: RNA
<213> ORGANISM: Artificial Sequence
<220> FEATURE:
<223> OTHER INFORMATION: stealth_62 sense

<400> SEQUENCE: 25

caacuucuag ccuuguuguc cuccu                                          25


<210> SEQ ID NO 26
<211> LENGTH: 25
<212> TYPE: RNA
<213> ORGANISM: Artificial Sequence
<220> FEATURE:
<223> OTHER INFORMATION: stealth_62 anti-sense

<400> SEQUENCE: 26

aggaggacaa caaggcuaga aguug                                          25
```